(12) United States Patent
Acton et al.

(10) Patent No.: US 6,228,581 B1
(45) Date of Patent: May 8, 2001

(54) HUMAN INTRONIC AND POLYMORPHIC SR-BI NUCLEIC ACIDS AND USES THEREFOR

(75) Inventors: Susan L. Acton, Lexington; Jose M. Ordovas, Framingham, both of MA (US)

(73) Assignees: Millennium Pharmaceuticals, Inc., Cambridge; Trustees of Tufts College, Boston, both of MA (US)

(*) Notice: Subject to any disclaimer, the term of this patent is extended or adjusted under 35 U.S.C. 154(b) by 0 days.

(21) Appl. No.: 09/031,626

(22) Filed: Feb. 27, 1998

Related U.S. Application Data

(63) Continuation-in-part of application No. 08/890,979, filed on Jul. 10, 1997, now Pat. No. 6,030,778.

(51) Int. Cl.[7] .............. C12Q 1/68; C02F 1/40; C07H 21/04
(52) U.S. Cl. ............... 435/6; 204/606; 536/24.3
(58) Field of Search .................. 435/6; 204/606; 536/24.3

(56) References Cited

U.S. PATENT DOCUMENTS 5,925,229 * 7/1999 Krauss ..................... 204/606

FOREIGN PATENT DOCUMENTS

| WO 96/00288 | 1/1996 | (WO) . |
| WO 97/02048 | 1/1997 | (WO) . |
| WO 97/18304 | 5/1997 | (WO) . |
| WO 98/39431 | 9/1998 | (WO) . |

OTHER PUBLICATIONS

Calvo et al., "Identification, Primary Structure, and Distribution of CLA–1, a Novel Member of the CD36/LIMPII Gene Family", Journal of Biological Chemistry, vol. 268 (25), pp. 18929–18935, Sep. 5, 1993.*

Stratagene Catalog, p. 39, 1988.*

Acton, S.L. et al. "Expression Cloning of SR–BI, a CD36–related Class B Scavenger Receptor" *J. Biol. Chem.* 269 (33):21003–21009, 1994.

Acton, S. et al. "Identification of Scavenger Receptor SR–BI as a High Density Lipoprotein Receptor" *Science* 271:518–520, 1996.

Calvo, D. and Vega, M.A. "Identification, primary structure, and distribution of CLA–1, a novel member of the CD36/LIMPH gene family" *J. Biol. Chem.* 268 (25):18929–18935, 1993.

(List continued on next page.)

*Primary Examiner*—Jeffrey Fredman
*Assistant Examiner*—Arun K. Chakrabarti
(74) *Attorney, Agent, or Firm*—Lahive & Cockfield, LLP

(57) ABSTRACT

The present invention is based at least in part on the discovery of the genomic structure of the human SR-BI gene and on the identification of polymorphic regions within the gene. Accordingly, the invention provides nucleic acids having a nucleotide sequence of an allelic variant of an SR-BI gene and nucleic acids having an SR-BI intronic sequence. The invention also provides methods for identifying specific alleles of polymorphic regions of an SR-BI gene, methods for determining whether a subject has or is at risk of developing a disease which is associated with a specific allele of a polymorphic region of an SR-BI gene, and kits for performing such methods.

51 Claims, 18 Drawing Sheets

OTHER PUBLICATIONS

Calvo, D. et al. "The CD36, CLA–1 (CD36L1), and LIMPII (CD36L2) Gene Family: Cellular Distribution, Chromosomal Location, and Genetic Evolution" *Genomics* 25:100–106, 1995.

Fukasawa, M. et al. "SRB1, a Class B scavenger receptor, recognizes both negatively charged liposomes and apoptotic cells" *Exper. Cell Research* 222:246–250, 1996.

Landschulz, K. et al. "Regulation of Scavenger Receptor, Class B, Type I, a High Density Lipoprotein Receptor in Liver and Steroidogenic Tissues of the Rat" *The American Cancer Society for Clinical Investigation, Inc.* vol. 98, No. 4, Aug. 1996 pp. 984–995.

Rigotti, A. et al. "The Class B Scavenger Receptors SR–BI and CD36 are Receptors for Anionic Phospholipids" *J. Biol. Chem.* 270 (27):16221–16224, 1995.

Riggoti, A. et al. "Regulation by Adrenocorticotropic Hormone of the in Vivo Expression of Scavenger Receptor Class B Type I (SR–BI), a High Density Lipoprotein Receptor, in Steroidogenic Cells of the Murine Adrenal Gland" *The Journal of Biological Chemistry*, vol. 271, No. 52 Dec. 27, pp. 33545–33549, 1996.

Tang, Y. et al. "Identification of a Human CD36 Isoform Produced by Exon Skipping" *J. Biol. Chem* 269 (8):6011–6015, 1994.

Wang, N. et al. "Scavenger Receptor BI (SR–BI) is up–regulated in adrenal gland in apolipoprotein A–I and hepatic lipase knock–out mice as a response to depletion of cholesterol stores" *J. Biol. Chem* 271 (35):21001–21004, 1996.

Orita, M. et al. "Detection of Polymorphisms of Human DNA by Gel Electrophoresis as Single–Strand Conformation Polymorphisms" *PNAS* 86(8):2766–2770, Apr. 1989, XP000310584.

Saiki, R.K. et al. "Genetic Analysis of Amplified DNA with Immobilized Sequence–Specific Oligonucleotide Probes" *PNAS* 86(16):6230–6234, Aug. 1989, XP000268602.

Frossard, P.M. et al. "ApaI RFLP 5.4 kn 5' to the human apolipoprotein AI (APO A1) gene" *Nuc. Acids Res.* 14(4), 1986, XP002090828.

Varban, M. et al. "Targeted mutation reveals a central role for SR–B1 in hepatic selective uptake of *high density lipoprotein* cholesterol" *PNAS* 95:4619–4624, Apr. 1998, XP002090830.

Rigotti, A. et al. "Targeted mutation of the gene encoding SR–B1 establishes that it *plays a key rol in* HDL metabolism" *FASEB Journal* 11(9):A1292, 1997, XP002090831.

International Search Report for PCT/US98/14354 dated Feb. 4, 1999.

Hillier, L. et al. "The WashU–Merck EST project (AC H22816)" EMEST13, 1995, XP002095407, Heidelberg.

Hillier, L. et al. "The WashU–Merck EST project (AC T39475)" EMEST13, 1995, XP002095408, Heidelberg.

Hillier, L. et al. "The WashU–Merck EST project (AC R59536)" EMEST13, 1995, XP002095409, Heidelberg.

Sanger, F. et al. "DNA Sequencing with Chain–Terminating Inhibitors" *PNAS*, 74(12): 5463–5467, Dec. 1977, XP000604551.

Botstein, D. et al. "Construction of a Genetic Linkage Map in Man Using Restriction Fragment Length Polymorphisms" *Am. J. Hum. Gen.* 32(3):314–331, May 1980, XP000610566.

Nickerson, D. et al. "Automated DNA Diagnostics Using an ELISA–Based Oligonucleotide Ligation Assay" *PNAS* 87(22):8923–8927, Nov. 1990, XP000209335.

Ganguly, A. et al. "Detection of Single–Based Mutations by Reaction of DNA Heteroduplexes with a Water–Soluble Carbodiimide Followed by Primer Extension: Application to Products from the Polymerase Chain Reaction" *Nuc. Acids Res.* 18(13):3933–3939, 1990, XP002033171.

\* cited by examiner promoter and exon 1

ACTGCGGAGATGAGGGTCTAGAAGGTGGTGGCGGGGCAT
GTGGACCGTTGTAAGGGCTCTGGGGTTCCTGGGTGGGCT
GGCGAAGTCCTACTCACAGTGACCAACCATGATGATGGT
CCCGATAGAGGAGGAGAGGGAGGAGGAGGGAAAAGGAAG
GGTGAGGGGCTCAGAGGGGAGAGCTGGGAGGAGGGGAGA
CATAGGTGGGGAAGGGGTAGGAGAAAGGGGAAGGGAGC
AAGAGGGTGAGGGGCACCAGGCCCCATAGACGTTTTGGC
TCAGCGGCCACGAGGCTTCATCAGCTCCCGCCCGAAAAC
GGAAGCGAGGCCGTGGGGGCAGCGGCAGCATGGCGGGGC
TTGTCTTGGCGGCCATGGCCCCGCCCCTGCCCGTCCGA
TCAGCGCCCGCCCCGTCCCGCCCCGACCCCGCCCCGG
GCCCGCTCAGGCCCCGCCCCTGCCGCCGGAATCCTGAAG
CCCAAGGCTGCCCGGGGGCGGTCCGGCGGCGCCGGCGAT
GGGGC*ATAAAA*CCACTGGCCACCTGCCGGGCTGCTCC

*TGCGTGCGCTGCCGTCCCGGATCC*ACCGTGCCTCTGCGG
CCTGCGTGCCCGGAGTCCCCGCCTGTGTCGTCTCTGTCG
CCGTCCCCGTCTCCTGCCAGGCGCGGAGCCCTGCGAGCC
GCGGGTGGGCCCCAGGCGCGCAGACATGGCTGCTCCGC     A
CAAAGCGCGCTGGGCTGCCGGGGCGCTGGCGTCGCGGG
GCTACTGTGCGCTGTGCTGGGCGCTGTCATGATCGTGAT
GGTGCCGTCGCTCATCAAGCAGCAGGTCCTTAAG

GTGGGTGAGGGAGACCCCAGGGGGTCCGCGCACGGACCC
GGCTGTTGGGCGCTGGGCGCCGGGAGGACCCGCGCGTT
GCGGTGGGTGGGCGACCGCAGCGGAATCGGCGCCCGGGC
CTGGCGCCGCAGAACACGAGGGAGGCCAGGCGCTTCGGG
AGGGGCTGCTGCCCGCCTCCCCACCACCCTCACC

Fig. 2A exon 2

AGCCTCATGTGCGAAGGGCTTTCCCACCACCTCCTATCC
CAAGCTCCCGCCGAGGAGCCCCTTCCCTGGCCGGGCTCG
GGCAGCTGTTCCGGAGCCTTGTGGTGGGGCG**TGGGGCC
CTCATCACTCTCCTCA**CAAGCGTACTTGTCCCTTCCC
CTGCAG

<u>AACGTGCGCATCGACCCCAGTAGCCTGTCCTTCAACATG
TGGAAGGAGATCCCTATCCCCTTCTATCTCTCCGTCTAC
TTCTTTGACGTCATGAACCCCAGCGAGATCCTGAAGGGC
GAGAAGCCGCAGGTGCGGGAGCGCGGGCCCTACGTGTAC
AG</u>

GTGAGGCTGTGTCCACGTGATGGTGGACGGGCCGGCTGA
CGCTGGGCATGGGACGGGTCTCAN**AGTGGACGGGATG
GGGAGGCTGC**TGACTGACCCCCAAACATTGTTCCGGAA
GCACGCAACTCATAGTCGGGGTAAGTGCTACTCCCAAAA
AAGTTTGCGT exon 3

CATGTCCTGCAGTGGGCAGGCAGCGGGAGGGACAGACTT
GGCGAAGGGGCCGAGCTCAGCTTTGGCTGTGGGGCCGGA
GGTGTGCACAGACGTCCAGGGCCCCTGGTTCCCAGGCAG
GCATTGCAGGCGAGTAGAAGGGAAACGTCCCATGCAG
CGGGGCGGGGCGTCTGACCCACTGGCTTCCCCCACAG

<u>GGAGTTCAGGCACAAAAGCAACATCACCTTCAACAACAA
CGACACCGTGTCCTTCCTcGAGTACCGCACCTTCCAGTT
CCAGCCCTCCAAGTCCCACGGCTCGGAGAGCGACTACAT
CC</u>GTCATGCCCAACATCCTGGTCTTG
  A

GTGAGGCTGCCCTGTGGCCCACGCCGCCTCGCACCCTGA
CCTCGTCCCCTGTCTCTCCTCCCGCCTGCCCCTTGTG
CAGAGAGCAGTCCCTGAGGTGGTCGGAGCGTGGGGACTC
ACGCCTGGTGGGTGGCTTTCGGCCCTGTGCTGTCTCCAC
CACCCCCA

Fig. 2B exon 4

GGTGGTTCTGGTGTCCCAGATGCCCCACGTGGCCACTCC
AGGGGCCTCCTGCACCCCAGCATTTCCCTTCA**TGGGCT
CTTTGCTGTGAGGC**CCAGCTGGGGCCAAGGGAGGATG
GGCCAGCCACGTCCAGCCTCTGACACTAGTGTCCCTTCG
CCTTGCAG

<u>GGTGCGGCGGTGATGATGGAGAATAAGCCCATGACCCTG
AAGCTCATCATGACCTTGGCATTCACCACCCTCGGCGAA
CGTGCCTTCATGAACCGCACTGTGGGTGAGATCATGTGG
GGCTACAAGGACCCCTTGTGAATCTCATCAACAAGTACT
TTCCAGGCATGTTCCCCTTCAAGGACAAGTTCGGATTAT
TTGCTGAG</u>

GTACGTGTGGCCTGGTGAGAAGCCAAAGATTCAGGCCTG
TGTCCTGTCTTCCCCTCACACAGCCTGGACACTGGTC
ACCAGCTTGCTTTGTAGCTGGCTGGGGATCTAGTGGCTG
TGGGTTGTAAGTGACTGAGAACCTGACTCAAACCGGCTT
GAGTGAAA exon 5

CCTCTCGGTCCCCAGACACTGGGCATTTGGCAGTGAACC
AGATGCTGGGGGCCCTGTCCTTCTGGTGGAGGGGGAGGA
GGGCTCAGCCCAGAATGTTCAGACCAGGCCGGCTCAA
TGGCAGGCCTAAGCCTTACGATGCTGTTCCCTGCTGTGT
CTGTAG

<u>CTCAACAACTCCGACTCTGGGCTCTTCACGGTGTTCACG
GGGGTCCAGAACATCAGCAGGATCCACCTCGTGGACAAG
TGGAACGGGCTGAGCAAG</u>

GTGAGGGGCGAGAGGCGAGGGCCCTGTCGCCAGGGAGA
GGGGAGGGTGGGCC[G]GGCCATGGCTGCTCGGGAGTGGCA    T
GGGACCAGAGAGCTCCTTCTTC**CTTTGTCGTGAAGAG
GGTGC**TGGGAGGATGAACACTCTTGAAGTTGGAGGAGGG
ATTTTA

Fig. 2C exon 6

TCTCTGTGTGTCTACATAGCCTGCCCTCTTCCCACCGTG
CCAGTATTGGGAATTGAGTGGCCGTGCGTGCACCAGGGT
GAGTTAGGTGTGCAGCACCTGAGAGGGCTTATTAAGG
GGCCTTGGCCCTACTGAGGGGTCTAGTCTGGATGCTTCC
CCCCAG

<u>GTTGACTTCTGGCATTCCGATCAGTGCAACATGATCAAT</u>
<u>GGAACTTCTGGGCAAATGTGGCCGCCCTTCATGACTCCT</u>
<u>GAGTCCTCGCTGGAGTTCTACAGCCCGGAGGCCTGCCG</u>

GTAATCACTGGGACTCGGGGCCTCCTGGGTTTCCTGGGT
AGCTCATGGCCAAATTCTGTGGTGTTGGCTGTGCACTT
GGAAAGCATTTTGACTCATCGTGGATTTGACTCAGTAG
CCCTTGGCACCAGCTTGAATTCTCTTTGGTCACACCACC
AAAAGC exon 7

GGAGGTCGCTGCAGCTCCGCGGGTGAGAGATGGGGGCGG
TTTGGACCCGGGAGGTGGTAGCGCCCGTGGGGAGAAGTG
GCTGGATCTGGGCAGCCTTTGGCAGGGCCTGGCTCTGGC
CGCCGGGTCTGGGTGTCCCCTCTCATCCTGTCTGTCC
CCTGCAG

<u>ATCCATGAAGCTAATGTACAAGGAGTCAGGGGTGTTTGA</u>
<u>AGGCATCCCCACCTATCGCTTCGTGGCTCCCAAAACCCT</u>
<u>GTTTGCCAACGGGTCCATCTACCCACCCAACGAAGGCTT</u>
<u>CTGCCCGTGCCTGGAGTCTGGAATTCAGAACGTCAGCAC</u>
<u>CTGCAGGTTCA</u>

GTACGTGCCGTCCCTGTTCTGGGATNGCCGGAGGGTGT
TAGGTNTNGGGCACCTNANGGTTTATCTGCCCAATGCTG
TCTGCTTAATCTCTGGCCTCTGTACTCTTGATAACC
CATTAAGCCAAAAATATGATGCCTCTGGGACGATATCTG

Fig. 2D exon 8

TGGGGCTTTTTACAGAATGGAGGAAGGGATCCTCTCT
GTCGGGTATTATGGTCATCGCCACGGGGGTGCCGTGCAG
ACCACAGCTCTGTGCAGACTTCCGGAGTGGCAGGACGTG
CCAATATACTGTCGTTGTATGATGTCCCCTCCCTGCCCT
TGTTGTAG

<u>GTGCCCCCTTGTTTCTCTCCCATCCTCACTTCCTCAACG
CC̲GACCCGGTTCTGGCAGAAGCGGTGACTGGCCTGCACC</u>   T
<u>CTAACCAGGAGGCACACTCCTTGTTCCTGGACATCCACC
CG</u>

GTGAGCCCCTGCCATCCTCTGTGGGGGGTGGGTGATTCC
TGGTTGGAGCACACCTGGCTGCCTCCTCTCTCCCCAG
GCAGAGAGCTGCTGTGGGCTGGGGTGGTGGGAAGCCTGG
CTTCTAGAATCTCGAGCCACCAAAGTTCCTTACT exon 9

CCCCAGCCTGTGGCTTGTTTTAGGTAAGATACAAGCAAG
CTCCACTGGGCAGTTAGCTGGGACGCCCACCCTCTTGAC
TGGGACCAGGGAAAAGAA**GGTTGACTGTGTCCCTGGA
G**CTTGGGGGTGGCCAGTCTCCTCACTGTGTTTGTTGCCG
CAG

<u>GTCACGGGAATCCCCATGAACTGCTCTGTGAAACTGCAG
CTGAGCCTCTACATGAAATCTGTCGCAGGCATTGG</u>

GTGAGTGGGGACTGGGAACTGGGGCTGCATTGCTCATTG
AGAGATTANGTGCTCAGTGCTCCAGTGTTCCCAGAC
TCCCCTGACATACCCCAGGAAACAGGGCATGGGGAAGGG
AGAGGGTCCTATTGGGGGTGGAATCCAGTCCCTGCTGAT
CTTCTC

Fig. 2E exon 10

ATGGCTCCTAAAGTGTTTCAGCTCATTGTTTATATTT**GG
TGGTGAGGGTTTAGTGTG**TGCAAAATTATACTAAACC
TGTTTAGATGTTGTATTCAAGCAGAATTAGATCAAGTTT
GGGTGTAAGACTTTGTTCCAACACCTATGTCTTGCTTAT
TTCCAG

<u>ACAAACTGGGAAGATTGAGCCTGTGGTCCTGCCGCTGCT
CTGGTTTGCAGAG</u>

GTAAGGGTGCGTTGGGCACAGCGTCGGGGGCTTTTGTTA
ATAGCCAATGTGGGCATTT**GAGGCAGGAGGCGGGGGG
AG**CACCTTGTAGAAGGGAGAGGGCTGAGCCAGGGTAAC
CGGACTGTTACATGGACCAGCGTATCATACACTTCACCC
TGTC exon 11

CCTGGAGGGAGGAGGTCCCTGGCAGGCTCCAACACATGC
TTTAGCCGGGAAGCTTGAGGTGGGGAAAAGCTGAGGCGG
GCACAGAGGAAGGTGTTGGGTGGCATCTGCGCTGTAG
CCCGCAGC[C]TGCGGCCCCAGCTCATGTGTTTGTCATTCT    G
GTCTCCTCAG

<u>AGCGGGGCCATGGAGGGGGAGACTCTTCACACATTCTAC
ACTCAGCTGGTGTTGATGCCCAAGGTGATGCACTATGCC
CAGTACGTCCTCCTGGCGCTGGGCTGCGTCCTGCTGCTG
GTCCTGTCATCTGCCAAATCCGGAGCCAA</u>

GTAGGTGCTGGCCAGAGGGCAGCCCGGGCTGACAGCCAT
TCGCTTGCCTGCTGGGGGAAAGGGGCCTCAGATCGGACC
CTCTGGCCAACCGCAGCCTGGAGCCCACCTCCAGCAG
CAGTCCTGCGTCTCTGCCGGAGTGGGAGCGGTCACTGCT
GGGGG

Fig. 2F exon 12

CCCCACATCTCAGCCACCTGCAATCGTTGAGGGTTGTTG
GACTCTAAACTTATGTGCCTTTCCTGTTTCCTCTTTGCC
TTTTGCAAATTGAAGAACCGTGTAAAACCATTTTTAT
GTGGCTTCAACGTCAACTATAATTAGCTTGGTTATCTT
CTAG

<u>GAGAAATGCTATTTATTTTGGAGTAGTAGTAAAAGGGC</u>
<u>TCAAAGGATAAGGAGGCCATTCAGGCCTATTCTGAATCC</u>
<u>CTGATGACATCAGCTCCCAAGGGCTCTGTGCTGCAGGAA</u>
<u>GCAAAACTGTAG</u>

GTGGGTACCAGGTAATGCCGTGCGCCTCCCCGCCCCCTC
CCATATCAAGTAGAATGCTGGCGGCTTAAAACATTTGGG
GTCCTGCTCATTCCTTCAGCCTCAACTTCACCTGGAG
TGTCTACAGACTGAAGATGCATATTTGTGTATTTTGCTT
TTGGAGAAA

Fig. 2G

ACCGTGCCTCTGCGGGCCTGCGTGCCCGGAGTCCCCGCCTGTGTCTCTGTCGCCGTCCCCGTCCCCGTCTCCTGCCAGGGCG 79

GAGCCCTGCGAGCCCCAGGCGCGGGGTGGGCCCCAGGCGCGAGAC ATG GGC TGC TCC GCC AAA GCG CGC TGG GCT 148
                                               M   G   C   S   A   K   A   R   W   A   10

A   G   A   L   G   V   A   G   L   C   A   V   L   G   A   V   M   I   V   30
GCC GGG GCG CTG GGC GTC GGC GGG CTA CTG TGC GCT GTG CTG GGC GCT GTC ATG ATC GTG   208
                                            ↑ exon 1

M   V   P   S   L   I   K   Q   Q   V   L   K   N   V   R   I   D   P   S   S   50
ATG GTG CCG TCG CTC ATC AAG CAG CAG GTC CTT AAG AAC GTG CGC ATC GAC CCC AGT AGC   268
                                          ↑ exon 2

L   S   F   N   M   W   K   E   I   L   P   F   Y   L   S   V   Y   F   F   70
CTG TCC TTC AAC ATG TGG AAG GAG ATC CTG CCC TTC TAT CTC TCC GTC TAC TTC TTT   328

D   V   M   N   P   S   E   E   F   K   P   E   K   Q   V   R   E   G   90
GAC GTC ATG AAC CCC AGC GAG GAG TTC AAG CCG GAG AAG CAG CGG GAG GGG   388
                      ↑ exon 3

P   Y   V   Y   R   M   R   T   F   Q   S   N   I   T   F   N   N   D   T   110
CCC TAC GTG TAC AGG ATG AGG ACC TTC CAG AGC AAC ATC ACC TTC AAC AAC GAC ACC   448

V   S   F   L   E   Y   R   T   F   Q   P   S   K   S   H   G   S   E   130
GTG TCC TTC CTC GAG TAC CGC ACC TTC CAG CCC TCC AAG TCC CAC GGC TCG GAG   508

S   D   Y   I   V   M   L   V   L   G   A   V   M   E   N   150
AGC GAC TAC ATC GTC ATG CTG GTT GGT GCG GCG GTG ATG GAG AAT   568
                                    ↑ exon 4

K   P   M   T   L   K   I   M   T   L   A   F   T   L   G   E   R   A   170
AAG CCC ATG ACC CTG AAG ATC ATG ACC TTG GCA TTC ACC CTC GGC GAA CGT GCC   628

```
AGGGAGAGGCTCGTCAACAACCACTGTTCTGGAACCTTCTCTCCACGTGGCCCTGACCACAGGGGCTGTGGG    1964
TCCTGCGTCCCCTTCCTCGGGTGAGCCTGGCCTGTCCCGTTCAGCCGTTGGGCCCAGGCTTCCTCCCCTCCAACGTGAA    2043
ACACTGCAGTCCCCGGTGTGGTGGCTCCCCCATGCAGGACGGGCCAGGCTGGGAGTGCCGCCTTCCTGTGCCAAATTCAGT    2122
GGGGACTCAGTGCCCAGGCCCTGGCCACGAGCTTTGGCCTTGGTCTACCTGCCAGGCCAGGCAAAGCCTTTACACAG    2201
GCCTCGGAAAACAATGGAGTGAGCACAAGATGCCCTGTGCAGCTGCCCGAGGGTCTCCGCCCACCCCGGCCGGACTTTG    2280
ATCCCCCGAAGTCTTCACAGGCACTCCATCGGGTTGTCTGGCGCCCTTTTCCTCCAGCCTAAACTGACATCATCCTAT    2359
GGACTGAGCCGGCCACTYTYTGGCCGAAGTGGCCCAGGCTGTGCCCCCGAGCTGCCCCACCCCCTCACAGGGTCCCT    2438
CAGATTATAGGTGCCCAGGCTGAGGTGAAGAGGCCTGGGGCCCTGCCTTCCGGCCGCTCCTGGACCCCTGGGGCAAACC    2517
TGTGACCCTTTTCTACTGGAATAGAAATGAGTTTATCATCTTTGAAAAATAATTCACTCTTGAAGTAATAAACGTTTA    2596
AAAAAATGGGAAAAAAAAAAAAAAAAAAAAAAAA    2630
```

Fig. 3B-2

HUMAN INTRONIC AND POLYMORPHIC SR-BI NUCLEIC ACIDS AND USES THEREFOR

This application is a continuation-in-part of U.S. application Ser. No. 08/890,979, filed Jul. 10, 1997 (U.S. Pat. No. 6,030,778), the contents of which are incorporated herein by reference.

GOVERNMENT SUPPORT

This invention was made with government support under 58-1950-9-001 awarded by the United States Department of Agriculture. The government has certain rights in the invention.

1. BACKGROUND OF THE INVENTION

Coronary heart disease is a major health risk throughout the industrialized world. Atherosclerosis, the most prevalent of cardiovascular diseases, is the principal cause of heart attack, stroke, and gangrene of the extremities, and thereby the principle cause of death in the United States. Although historically much emphasis has been placed on total plasma cholesterol levels as a risk factor for coronary heart disease, it has been clearly established that low levels of high density lipoprotein cholesterol (HDL-C) is an independent risk factor for this disease. Family and twin studies have shown that there are genetic components that affect HDL levels. However, mutations in the main protein components of HDL (ApoAI and ApoAII) and in the enzymes that are known to be involved in HDL metabolism (e.g., CETP, HL, LPL and LCAT) do not explain all of the genetic factors affecting HDL levels in the general population (J. L. Breslow, in *The Metabolic and Molecular Bases of Inherited Disease*, C. R. Scriver, A. L. Beaudet, W. Sly, D. Valle, Eds. (McGraw-Hill, New York, 1995), pp 2031–2052; and S. M. Grundy, (1995) *J. Am. Med. Assoc.* 256: 2849). This finding in combination with the fact that the mechanisms of HDL metabolism are poorly understood, suggests that there are other as yet unknown factors that contribute to the genetic variability of HDL levels.

Another disorder that is often associated with high triglyceride and low high density lipoprotein (HDL) concentrations is obesity, which renders a subject susceptible to cardiovascular diseases, such as ischemia, restenosis, congestive heart failure, and atherosclerosis. Severely obese individuals (weighing 60% over a normal weight) have a high risk of developing cardiorespiratory problems. They are also at risk of developing chronic hypoventilation, which can lead to hypercapnia, pulmonary hypertension, and heart failure. Severe episodic hypoxia, which can cause arrhythmias and sudden death, is 10 times more common in the severely obese. Severely obese individuals are also at increased risk of suffering from obstructive sleep apnea, pickwickian syndrome (i.e., daytime hypoventilation, somnolence, polycythemia, cor pulmonale), and renal vein thrombosis. ("Cecil Essentials of Medicine", Andreoli et al., Third Edition, 1993, W. B. Saunders Company).

Moderate obesity (corresponding to a weight between 20–60% above normal weight) poses increased risk of early mortality. Obese individuals suffer more frequently than non obese individuals from hypertension. Type II diabetes mellitus can also be aggravated by excess weight. Obesity can also increase the risk of a subject developing cholelithiasis and endometrial carcinoma.

One candidate factor that is likely to be involved both in obesity and cardiovascular disease is the SR-BI receptor, which has been shown to bind HDL and LDL cholesterol and mediate uptake into cells (Acton, S. et al., (1996) *Science* 271:518–520). SR-BI is likely to contribute to genetic lipoprotein variability, thereby playing a role in the development of lipid metabolism disorders and thus generally, cardiovascular diseases.

In addition, cholesterol gallstone formation could be caused by a defective SR-BI receptor, since the SR-BI receptor is likely to be involved in transferring HDL-cholesterol from extrahepatic tissues to the liver (reverse cholesterol transport) e.g. for incorporation into bile (J. L. Breslow, in *The Metabolic and Molecular Bases of Inherited Disease*, C. R. Scriver, A. L. Beaudet, W. Sly, D. Valle, Eds. (McGraw-Hill, New York, 1995), pp 2031–2052; S. M. Grundy, (1995) *J. Am. Med. Assoc.* 256: 2849; G. Assman, A. von Eckardstein, H. B. Brewer Jr. in *The Metabolic and Molecular Bases of Inherited Disease*, C. R. Scriver, A. L. Beaudet, W. Sly, D. Valle, Eds. (McGraw-Hill, New York, 1995), pp 2053–2072; W. J. Johnson et al., (1991) *Biochem. Biophys. Acta* 1085:273; M. N. Pieters et al., (1994) *Ibid* 1225:125; and C. J. Fielding and P. E. Fielding, (1995) *J. Lipid Res* 36:211).

Further, a defective SR-BI receptor or abnormal levels of SR-BI receptor could influence the fertility of a subject, since SR-BI appears to be involved in HDL-cholesteryl ester delivery to steroidogenic tissues (ovary, adrenal glands and testis) for hormone synthesis (Acton, S. et al., (1996) *Science* 271:518–520; Landschulz, et al., (1996) *J. Clin. Invest.* 98:984–95; J. M. Anderson and J. M. Dietschy (1981) *J. Biol. Chem.* 256: 7362; M. S. Brown et al., (1979) *Recent Prog Horm. Res.* 35:215; J. T. Gwynne and J. F. Strauss III, (1982) *Endocr. Rev.* 3:299; B. D. Murphy et al., (1985) *Endocrinology* 116: 1587).

The SR-BI receptor (Scavenger Receptor-BI) is a scavenger receptor that mediates endocytosis of unmodified and modified lipoproteins, e.g., LDL, acetylated LDL, oxidized LDL (Acton et al. (1994) J. Biol. Chem. 269:21003), HDL ((Acton, S. et al., (1996) *Science* 271:518–520), anionic phospholipids (Rigotti et al. (1995) J. Biol. Chem. 270:16221), negatively charged liposomes and apoptotic cells (Fukasawa et al. (1996) Exp. Cell Res. 222:246). The human SR-BI receptor (also termed "CLA-1") exists in two differentially spliced forms (Calvo and Vega (1993) J. Biol. Chem. 268:18929). The predominant form of human SR-BI is a protein of 509 amino acids. The shorter form of the SR-BI receptor has 409 amino acids, and is lacking the 100 amino acids located 42 amino acids downstream of the initiation codon (Calvo and Vega, supra). The nucleotide sequence of a cDNA encoding human SR-BI is disclosed in Calvo and Vega, supra and the nucleotide sequence of a cDNA encoding hamster SR-BI is disclosed in Acton et al. (1994) J. Biol. Chem. 269:21003 and in PCT Application WO 96/00288.

2. SUMMARY OF THE INVENTION

The present invention is based at least in part on the discovery of the genomic structure of the human SR-BI gene and on the identification of polymorphic regions within the gene, which are associated with specific diseases or disorders, including abnormal body mass and abnormal lipoprotein levels, i.e., high HDL and low LDL levels. The human SR-BI gene contains 12 coding exons and one non coding exon (exon 13). The structure of the gene and the position of the introns relative to the nucleotide sequence of the exons are shown in FIGS. 1, 2, and 3.

Several polymorphic regions that are associated with specific diseases or disorders, have been found in the human SR-BI gene by analyzing the DNA of a specific population of individuals. One polymorphism found in the population is a change from a guanine to an adenine at position 146 in exon 1, which results in a change from a glycine to a serine at amino acid residue 2 of the encoded protein. A second polymorphism is a change from a guanine to an adenine at position 119 in exon 3, which results in a change from a valine to an isoleucine at amino acid residue 135 of the encoded protein. A third polymorphism is a change from a cytidine to a thymidine at position 41 of exon 8, which does not result in a difference in the amino acid sequence of the encoded protein. A fourth polymorphism is a change from a cytidine to a thymidine at position 56 of intron 5. A fifth polymorphism is a change from a cytidine to a guanine at position −41 of intron 10 (position −1 corresponds to the first nucleotide upstream of exon 11).

Specific allelic variants of these polymorphic regions are shown herein to be associated with specific disorders. In particular, the presence of a thymidine at position 41 in exon 8 was found to be associated with low plasma LDL levels in women. Furthermore, a thymidine at position 54 of intron 5 was found to be associated with a high BMI and high plasma LDL levels in women. In men, the presence of a thymidine at position 41 in exon 8, a thymidine at position 54 of intron 5 and/or an adenine at position 146 of exon 1 was found to be associated with a high plasma HDL level. Since abnormal lipid, lipoprotein levels, and BMI may be associated with obesity, cachexia, cardiovascular disease, gallstone formation and other disorders, SR-BI polymorphic variants are directly or indirectly associated with obesity, cachexia, cardiovascular disease, gallstone formation and other disorders.

In one embodiment, the invention provides isolated nucleic acids comprising an intronic sequence from an SR-BI gene. In a preferred embodiment, the SR-BI gene is a human gene. In another preferred embodiment, the nucleic acid of the invention has a nucleotide sequence set forth in FIG. 2 or in any of the intronic sequences in SEQ ID Nos. 1–121, complements thereof, or homologs thereof. In yet another embodiment, the intronic sequence of the nucleic acid is capable of hybridizing under an appropriate stringency to a nucleic acid having an intronic nucleotide sequence set forth in any of SEQ ID Nos. 1–121 or complements thereof.

Other preferred nucleic acids of the invention comprise at least an allelic variant of a polymorphic region. A preferred allele has a polymorphic region that is located in an exon and comprises, e.g., a nucleotide sequence set forth in SEQ ID NO: 65, SEQ ID NO: 95, or SEQ ID NO:96 or a polymorphic region that is located in an intron and comprises, e.g., a nucleotide sequence set forth in SEQ ID NO: 66 or SEQ ID NO: 97. The isolated nucleic acid preferably comprises from about 15 to about 30 nucleotides and can comprise, e.g., a nucleotide sequence selected from the group consisting of SEQ ID NO: 41 to SEQ ID NO: 64 and SEQ ID NO: 89 to SEQ ID NO: 94. The isolated nucleic acid can be double stranded or single stranded and can further comprise a label.

The nucleic acids of the invention can be used, e.g., in prognostic, diagnostic, and therapeutic methods. For example, the nucleic acids of the invention can be used as probes or primers to determine whether a subject has or is at risk of developing a disease or disorder associated with a specific allelic variant of an SR-BI polymorphism, e.g., a disease or disorder associated with an aberrant SR-BI activity.

The invention further describes vectors comprised of the claimed nucleic acids; host cells transfected with said vectors whether prokaryotic or eukaryotic; and transgenic non-human animals which contain a heterologous form of a functional or non-functional SR-BI allele described herein. Such a transgenic animal can serve as an animal model for studying, e.g., the effect of specific allelic variations, including mutations of an SR-BI gene or for use in drug screening or recombinant protein production.

The invention further provides methods for determining the molecular structure of at least a portion of an SR-BI gene. In a preferred embodiment, the method comprises contacting a sample nucleic acid comprising an SR-BI gene sequence with a probe or primer having a sequence which is complementary to an SR-BI gene sequence and comparing the molecular structure of the sample nucleic acid with the molecular structure of a control (known) SR-BI gene (e.g., an SR-BI gene from a human not afflicted with a cardiovascular condition or a disease associated with an aberrant SR-BI activity). The method of the invention can be used for example in determining the molecular structure of at least a portion of an exon, an intron, or the promoter. In a preferred embodiment, the method comprises determining the identity of at least one nucleotide. In even more preferred embodiments, the nucleotide is nucleotide 146 of exon 1, nucleotide 119 of exon 3, nucleotide 41 of exon 8, nucleotide 54 of intron 5, and/or nucleotide −41 of intron 10. In another preferred embodiment, the method comprises determining the nucleotide content of at least a portion of an SR-BI gene, such as by sequence analysis. In yet another embodiment, determining the molecular structure of at least a portion of an SR-BI gene is carried out by single-stranded conformation polymorphism. In yet another embodiment, the method is an oligonucleotide ligation assay. Other methods within the scope of the invention for determining the molecular structure of at least a portion of an SR-BI gene include hybridization of allele-specific oligonucleotides, sequence specific amplification, and primer specific extension.

In at least some of the methods of the invention, the probe or primer is allele specific. Preferred probes or primers are single stranded nucleic acids, which optionally are labeled.

The methods of the invention can be used for determining the identity of the allelic variant of a polymorphic region of a human SR-BI gene present in a subject. For example, the method of the invention can be useful for determining whether a subject has, or is at risk of developing, a disease or condition associated with a specific allelic variant of a polymorphic region in the human SR-BI gene. In one embodiment, the disease or condition is characterized by an aberrant SR-BI activity, such as an aberrant SR-BI protein level, which can result from an aberrant expression of an SR-BI gene. The disease or condition can be an abnormal lipid metabolism, inappropriate lipid or lipoprotein level, an abnormal body mass index, atherosclerosis, or gallstone formation. Accordingly, the invention provides methods for predicting or diagnosing cardiovascular diseases and other diseases associated with an aberrant SR-BI activity.

For example, a female subject having the more common allele (a cytidine) at residue 41 of exon 8 of SR-BI has or is likely to have a tendency of having higher LDL levels than a female subject having a thymidine at that position, thereby being at a higher risk of developing a cardiovascular disease; a female subject having the less common allele (a thymidine) at residue 54 of intron 5 has or is likely to develop a high BMI and/or high LDL levels, relative to a female subject having a cytidine at that position; and a male subject having the more common allele at residue 41 of exon 8, the more common allele at residue 54 of intron 5, and the more common allele at residue 146 of exon 1 is likely to have or to develop lower HDL levels relative to a subject male having the less common alleles of at least one of these polymorphic regions, thereby being at a higher risk of developing a cardiovascular disease.

The methods of the invention can also be used in selecting the appropriate drug to administer to a subject to treat a disease or condition, such as an abnormal lipid metabolism, inappropriate lipid level, a cardiovascular disease such as atherosclerosis, gallstone formation, or an abnormal body mass index. In fact, specific allelic variants of SR-BI polymorphic regions may be associated with a specific response of an individual having such an allele to a specific drug. For example, a specific SR-BI allele may encode an SR-BI protein having a modified affinity for certain types of molecules, e.g, lipids. Accordingly, the action of a drug necessitating interaction with an SR-BI protein will be different in individuals carrying such an SR-BI allele.

In a further embodiment, the invention provides a method for treating a subject having a disease or condition associated with a specific allelic variant of a polymorphic region of an SR-BI gene. In one embodiment, the method comprises (a) determining the identity of the allelic variant; and (b) administering to the subject a compound that compensates for the effect of the specific allelic variant. In a preferred embodiment, the specific allelic variant is a mutation. The mutation can be located, e.g., in a promoter region, an intron, or an exon of the gene. In one embodiment, the compound modulates (i.e., agonizes or antagonizes) SR-BI protein levels. In a preferred embodiment, the compound is selected from the group consisting of a nucleic acid, a protein, a peptidomimetic, or a small molecule. The compound can be, for example an, SR-BI protein. Thus, e.g., if a female subject has the more common allele of residue 41 of exon 8, high LDL levels and resulting cardiovascular disorders can be prevented from occurring or can be reduced, by administering to the subject a pharmaceutically effective amount of a compound which reduces LDL level to a normal LDL level. Similarly, if a female subject has the less common allele of residue 54 of intron 5, a high BMI and/or LDL level and consequences thereof, such as diabetes and cardiovascular disorders, can be prevented from occurring or can be reduced, by administering to the subject a pharmaceutically effective amount of a compound which reduces the BMI and/or the LDL levels. If, on the other hand, a male subject has the more common allele at residue 41 of exon 8, the more common allele at residue 54 of intron 5, and the more common allele at residue 146 of exon 1, development of low HDL levels can be prevented or increased by administering to the subject a pharmaceutically effective amount of a compound that increases HDL levels.

The invention also provides probes and primers comprising substantially purified oligonucleotides, which correspond to a region of nucleotide sequence which hybridizes to at least 6 consecutive nucleotides of the sequence set forth as SEQ ID Nos: 1, 2, or 3 or to the complement of the sequences set forth as SEQ ID Nos: 1, 2, or 3; or naturally occurring mutants thereof. In preferred embodiments, the probe/primer further includes a label group attached thereto, which is capable of being detected.

In another embodiment, the invention provides a kit for amplifying and/or for determining the molecular structure of at least a portion of an SR-BI gene, comprising a probe or primer capable of hybridizing to an SR-BI gene and instructions for use. In one embodiment, the probe or primer is capable of hybridizing to an SR-BI intron. In another embodiment, the probe or primer is capable of hybridizing to an allelic variant of a polymorphic region. In a preferred embodiment, the polymorphic region is located in an exon, such as exon 1, 3, or 8 or in an intron, such as intron 5 or 10. In a preferred embodiment, determining the molecular structure of a region of an SR-BI gene comprises determining the identity of the allelic variant of the polymorphic region. Determining the molecular structure of at least a portion of an SR-BI gene can comprise determining the identity of at least one nucleotide or determining the nucleotide composition, e.g., the nucleotide sequence.

A kit of the invention can be used, e.g., for determining whether a subject has or is at risk of developing a disease associated with a specific allelic variant of a polymorphic region of an SR-BI gene. In a preferred embodiment, the invention provides a kit for determining whether a subject has or is at risk of developing a disease or condition associated with abnormal lipid metabolism, inappropriate lipid or lipoprotein levels, a cardiovascular disease such as atherosclerosis, gallstone formation, or an abnormal body mass index. The disease or condition can be associated with an aberrant SR-BI activity, which can result, e.g., from a mutation in the SR-BI gene. The kit of the invention can also be used in selecting the appropriate drug to administer to a subject to treat a disease or condition, such as a disease or condition set forth above. In fact, pharmacogenetic studies have shown that the genetic background of individuals play a role in determining the response of an individual to a specific drug. Thus, determining the allelic variants of SR-BI polymorphic regions of an individual can be useful in predicting how an individual will respond to a specific drug, e.g, a drug for treating a disease or disorder associated with an aberrant SR-BI activity and/or a cardiovascular disease or a disease associated with an aberrant lipid level.

Other features and advantages of the invention will be apparent from the following detailed description and claims.

3. BRIEF DESCRIPTION OF THE FIGURES

FIG. 1 is a schematic depiction of the chromosomal structure of the human SR-BI gene indicating the introns (1 through 12) and exons (I-XIII). Black boxes represent coding exons (exons I-XII) and the white box represents the non-coding exon (exon XIII) boxed and the nucleotides in the newly identified alleles are indicated.

FIGS. 2A–2G represents the nucleotide sequence of the exons (underlined sequence) of the human SR-BI gene, portions of the introns which are adjacent to the exons, and 3' end of promoter sequence (SEQ ID Nos. 5–40). The putative 5' end of the cDNA, as predicted by GRAIL is indicated in italics. The TATA-like box is indicated in italics and is boxed. Bold sequences correspond to the nucleotide sequence or the complement of the nucleotide sequence of preferred primers for amplifying each of the exons or a promoter region. The nucleotide polymorphisms in exons 1, 3, and 8 and introns 5 and 10 are boxed.

FIGS. 3A and 3B shows the nucleotide sequence of the full length human SR-BI cDNA (SEQ ID NO: 1) and the position of introns 1–12 relative to the nucleotide sequence of the exons. The nucleotide polymorphisms in exons 1, 3, and 8 are boxed.

4. DETAILED DESCRIPTION OF THE INVENTION

4.1. General

The present invention is based at least in part on the discovery of the genomic structure of the human SR-BI gene and on the identification of polymorphic regions within the gene which correlate with specific diseases or conditions, such as an abnormal BMI or an abnormal lipoprotein (i.e., HDL or LDL) level.

Figure 1:
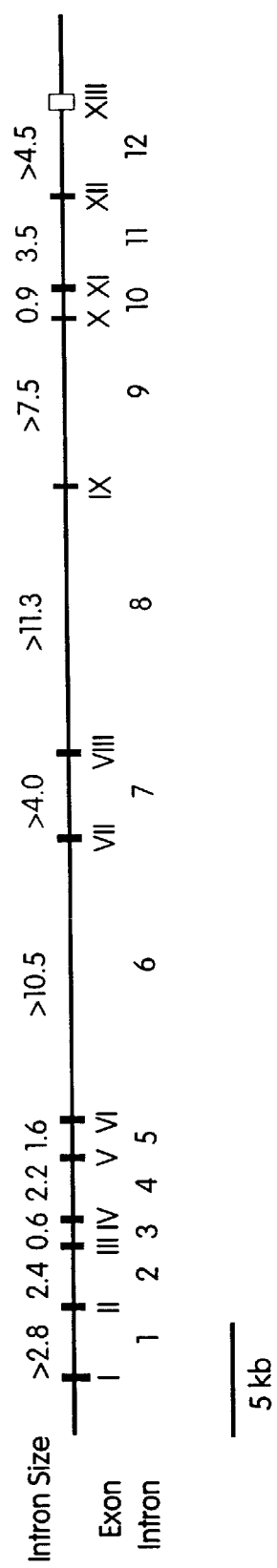

As shown in FIG. 1, the human SR-BI gene is at least 50 kilobase pairs long and has 12 coding exons, one non-coding exon (exon 13), and 12 introns. The exons are numbered 1 to 13 from 5' to 3' and the introns are labeled 1 through 12 from 5' to 3'. Exon 1 corresponds to the first exon located downstream of the promoter and contains the initiation codon. Intron 1 is located immediately downstream of exon 1 (see FIG. 1). The position of the introns relative to the nucleotide sequence of the full length cDNA encoding SR-BI is shown in FIG. 2. The nucleotide sequence of the human SR-BI cDNA, shown in FIG. 3 and in SEQ ID NO: 1 encodes a protein of 509 amino acids. SEQ ID NO. 1 contains the nucleotide sequence of the cDNA disclosed in Calvo and Vega (1993) J. Biol. Chem. 268:18929, and contains in addition a complete 5' end. The amino acid sequence of the protein set forth in SEQ ID NO: 2 is identical to the Cla-I protein disclosed in Calvo and Vega (1993) J. Biol. Chem. 268:18929. As set forth in Calvo and Vega, supra, differential splicing of the human SR-BI gene also results in a short mRNA lacking 300 nucleotides located 126 nucleotides downstream of the initiation codon, i.e., lacking exons 2 and 3 set forth in FIG. 3, which encodes a protein of 409 amino acids. The shorter protein is referred to herein as "splice variant". The nucleotide sequence of a full length cDNA encoding the splice variant is set forth in SEQ ID NO: 3 and the amino acid sequence of the SR-BI splice variant protein encoded by this nucleotide sequence is set forth in SEQ ID NO: 4. The splice variant is rare relative to the 509 amino acid SR-BI protein.

FIG. 2 shows the nucleotide sequence of the 3' end of the SR-BI promoter. Additional promoter sequence is disclosed in U.S. patent application Ser. No. 08/812,204 by Acton, incorporated herein by reference.

Set forth below in Table I are the locations and sizes of the exons in the human SR-BI gene relative to the nucleotide sequence of a full length cDNA encoding human SR-BI protein (SEQ ID NO: 1), in which nucleotide 1 corresponds to the first nucleotide in the isolated transcript. Table I also indicates the portions of the human SR-BI protein encoded by each of these exons. Amino acid 1 is the initiating methionine. Also indicated is the length of the intron located downstream of each of the exons.

TABLE I

| | cDNA Nucleotide position | Amino acid position | Size of intron |
|---|---|---|---|
| Exon 1 | 1–244 | 1–42 | intron 1: >2827 |
| Exon 2 | 245–402 | 43–95 | intron 2: 2429 |
| Exon 3 | 403–544 | 95–142 | intron 3: 567 |
| Exon 4 | 545–748 | 143–210 | intron 4: 2229 |
| Exon 5 | 749–844 | 211–242 | intron 5: 1580 |
| Exon 6 | 845–960 | 243–281 | intron 6: >10532 |
| Exon 7 | 961–1127 | 281–337 | intron 7: >3985 |
| Exon 8 | 1228–1246 | 337–376 | intron 8: >11321 |
| Exon 9 | 1247–1320 | 377–401 | intron 9: 7562 |
| Exon 10 | 1321–1372 | 401–418 | intron 10: 902 |
| Exon 11 | 1373–1519 | 419–467 | intron 11: 3547 |
| Exon 12 | 1520–1648 | 468–509 | intron 12: >4578 |
| Exon 13 | 1649–2630 | | |

FIG. 2 shows the nucleotide sequence of portions of the introns which are adjacent to the exons. The nucleotide sequence of each of the exons and adjacent portions of introns shown in FIG. 2 are set forth in SEQ ID Nos. 5 to 16. The portions of each of the introns shown in FIG. 2 are set forth in SEQ ID Nos. 18 to 40. For convenience, the identity of the sequences referred to as SEQ ID Nos. 1 to 40 are set forth below in Table II:

TABLE II

| | |
|---|---|
| SEQ ID NO: 1 | full length cDNA encoding human SR-BI; |
| SEQ ID NO: 2 | full length amino acid sequence of human SR-BI protein; |
| SEQ ID NO: 3 | full length cDNA encoding splice variant of human SR-BI (Calvo and Vega, supra); |
| SEQ ID NO: 4 | full length amino acid sequence of splice variant of human SR-BI protein (Calvo and Vega, supra); |
| SEQ ID NO: 5 | 3' end of promoter, exon 1, and 5' end of intron 1; |
| SEQ ID NO: 6 | 3' end of intron, exon 2, and 5' end of intron 2; |
| SEQ ID NO: 7 | 3' end of intron 2, exon 3, and 5' end of intron 3; |
| SEQ ID NO: 8 | 3' end of intron 3, exon 4, and 5' end of intron 4; |
| SEQ ID NO: 9 | 3' end of intron 4, exon 5, and 5' end of intron 5; |
| SEQ ID NO: 10 | 3' end of intron 5, exon 6, and 5' end of intron 6; |
| SEQ ID NO: 11 | 3' end of intron 6, exon 7, and 5' end of intron 7; |
| SEQ ID NO: 12 | 3' end of intron 7, exon 8, and 5' end of intron 8; |
| SEQ ID NO: 13 | 3' end of intron 8, exon 9, and 5' end of intron 9; |
| SEQ ID NO: 14 | 3' end of intron 9, exon 10, and 5' end of intron 10; |
| SEQ ID NO: 15 | 3' end of intron 10, exon 11, and 5' end of intron 11; |
| SEQ ID NO: 16 | 3' end of intron 11, exon 12, and 5' end of intron 12; |
| SEQ ID NO: 17 | 3' end of promoter; |
| SEQ ID NO: 18 | 5' end of intron 1; |
| SEQ ID NO: 19 | 3' end of intron 1; |
| SEQ ID NO: 20 | 5' end of intron 2; |
| SEQ ID NO: 21 | 3' end of intron 2; |
| SEQ ID NO: 22 | 5' end of intron 3; |
| SEQ ID NO: 23 | 3' end of intron 3; |
| SEQ ID NO: 24 | 5' end of intron 4; |
| SEQ ID NO: 25 | 3' end of intron 4; |
| SEQ ID NO: 26 | 5' end of intron 5; |
| SEQ ID NO: 27 | 3' end of intron 5; |
| SEQ ID NO: 28 | 5' end of intron 6; |
| SEQ ID NO: 29 | 3' end of intron 6; |
| SEQ ID NO: 30 | 5' end of intron 7; |
| SEQ ID NO: 31 | 3' end of intron 7; |

TABLE II-continued

| SEQ ID NO: 32 | 5' end of intron 8; |
|---|---|
| SEQ ID NO: 33 | 3' end of intron 8; |
| SEQ ID NO: 34 | 5' end of intron 9; |
| SEQ ID NO: 35 | 3' end of intron 9; |
| SEQ ID NO: 36 | 5' end of intron 10; |
| SEQ ID NO: 37 | 3' end of intron 10; |
| SEQ ID NO: 38 | 5' end of intron 11; |
| SEQ ID NO: 39 | 3' end of intron 11; and |
| SEQ ID NO: 40 | 5' end of intron 12. |

An analysis of the human SR-BI gene in a population of individuals chosen because these individuals had a known age, known HDL and LDL levels, known body mass index, and known triglycerides and total cholesterol levels revealed the existence of several polymorphisms in the SR-BI gene in this population. These polymorphisms were identified by performing single stranded conformation polymorphism (SSCP) analysis of genomic DNA from independent individuals as described in Example 3, using PCR primers complementary to intronic or promoter sequences surrounding each of the exons. The nucleotide sequence of these PCR primers (having SEQ ID Nos. 41–64) is shown in Table IV (in the Examples).

The results indicated the presence of at least five polymorphic regions in the human SR-BI gene in the population studied. The location and identity of these polymorphisms is indicated in Table III.

is set forth in SEQ ID NO: 96 (which is identical to SEQ ID NO: 7, except for nucleotide 119 of exon 3 which is an adenine).

A third polymorphism is a change from a cytidine to a thymidine at position 41 of exon 8, which does not result in a difference in the amino acid sequence of the encoded protein. The nucleotide sequence of exon 8 of this allele is set forth in SEQ ID NO: 65 (SEQ ID NO: 65 is identical to SEQ ID NO: 12, except for nucleotide 41 of the exon sequence which is a thymidine). About 35% of the individuals of a Spanish population of 142 individuals were found to be homozygous for the allele having a cytidine at position 41 (i.e., SR-BI sequence originally disclosed); about 17% of the individuals were found to be homozygous for the allele having a thymidine at position 41 of exon 8; and about 48% of the individuals were found to be heterozygous, i.e., having one allele having a cytidine at position 41 and one allele having a thymidine at position 41.

A fourth polymorphism is a change from a cytidine to a thymidine at position 54 of intron 5 (position 1 being defined as the first nucleotide in the intron). This nucleotide substitution destroys the ApaI restriction site which is present when the nucleotide at position 54 is a cytidine. The nucleotide sequence of the 5' end of intron 5 of this allele is set forth in SEQ ID NO: 66 (SEQ ID NO: 66 is identical to SEQ ID NO: 26, except for nucleotide 54 which is a thymidine).

A fifth polymorphism in the SR-BI gene is a change from a cytidine to a guanine at position –41 of intron 10 (position

TABLE III

Locations of polymorphisms in the human SR-BI gene.

| polymorphism | cDNA position | amino acid position | change | location |
|---|---|---|---|---|
| exon 1 | 4 | 2 | Gly -> Ser | 1   2   3<br>ATG (G/A)GC TGC |
| exon 3 | 403 | 135 | Val -> Ile | 135   136 137<br>(G/A)TC ATG CCC |
| intron 5 | na | na | na | 240 241 242<br>CTG AGC AAG gtgaggggcgagaggcgagggccctgt<br>                                  cgccagggagggagggtgggcc(c/t)g SEQ ID NO:87 |
| exon 8 | 1050 | 350 | none | 350   351 352<br>(G/A)TC ATG CCC |
| intron 10 | na | na | na |                                                                                                  419<br>c(c/g)tgcggccccagctcatgtgtttgtcattctgtctcctcag AGC<br><br>420 421<br>GGG GCC SEQ ID NO:88 |

The intron is defined as being after its corresponding exon (intron 1 is 3' of exon 1), cDNA position 1 = the first base of the initiator methionine, the numbers above the sequences refer to the amino acid number, na = not applicable, lower case indicates intronic sequence, and the polymorphisms are in parentheses.

As can be seen in Table III, one polymorphism is a change from a guanine to an adenine at position 146 in exon 1, which results in a change from a glycine to a serine at amino acid residue 2 of the encoded protein. The nucleotide sequence of this allele is set forth in SEQ ID NO: 95 (which is identical to SEQ ID NO: 5, except for nucleotide 146 of exon 1 which is an adenine).

A second polymorphism is a change from a guanine to an adenine at position 119 in exon 3, which results in a change from a valine to an isoleucine at amino acid residue 135 of the encoded protein. The nucleotide sequence of this allele –1 corresponds to the first nucleotide upstream of exon 11). The nucleotide sequence of the 3' end of intron 10 of this allele is set forth in SEQ ID NO: 97 (SEQ ID NO: 97 is identical to SEQ ID NO: 15, except for nucleotide –41 of intron 10 which is a guanine).

Further analysis of the human SR-BI gene is likely to reveal the existence of yet other polymorphic regions. Such analysis can be performed using the methods described herein and genomic DNA from random subjects or subjects of families associated with specific diseases. For example, the polymorphism studies described herein can also be applied to populations in which cholesterol gallstones are prevalent.

Accordingly, the invention provides nucleic acids, e.g, intronic sequences useful as probes or primers for determining the identity of an allelic variant of an SR-BI polymorphic region. The invention also provides methods for determining the identity of the alleles of a specific polymorphic region of an SR-BI gene. Such methods can be used, for example, to determine whether a subject has or is at risk of developing a disease or condition associated with one or more specific alleles of polymorphic regions of an SR-BI gene. In a preferred embodiment, the disease or condition is caused or contributed to by an aberrant SR-BI bioactivity. Other aspects of the invention are described below or will be apparent to one of skill in the art in light of the present disclosure.

4.2 Definitions

For convenience, the meaning of certain terms and phrases employed in the specification, examples, and appended claims are provided below.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

The term "allelic variant of a polymorphic region of an SR-BI gene" refers to a region of an SR-BI gene having one of several nucleotide sequences found in that region of the gene in other individuals.

"Biological activity" or "bioactivity" or "activity" or "biological function", which are used interchangeably, for the purposes herein when applied to SR-BI means an effector or antigenic function that is directly or indirectly performed by an SR-BI polypeptide (whether in its native or denatured conformation), or by any subsequence (fragment) thereof. Biological activities include binding to a ligand, e.g., a lipid or lipoprotein, such as LDL or modified forms thereof, or HDL or modified forms thereof. Other molecules which can bind an SR-BI receptor include anionic molecules, such as anionic phospholipids, negatively charged liposomes, and apoptotic cells. Another biological activity of an SR-BI protein includes endocytosis of a ligand interacting with the receptor. A biological activity is also intended to include binding to a protein, such as binding to the cytoplasmic domain of SR-BI. Yet other biological activities include signal transduction from the receptor, modulation of expression of genes responsive to binding of a ligand to an SR-BI receptor, and other biological activities, whether presently known or inherent. An SR-BI bioactivity can be modulated by directly affecting an SR-BI protein. Alternatively, an SR-BI bioactivity can be modulated by modulating the level of an SR-BI protein, such as by modulating expression of an SR-BI gene. Antigenic functions include possession of an epitope or antigenic site that is capable of cross-reacting with antibodies raised against a naturally occurring or denatured SR-BI polypeptide or fragment thereof.

Biologically active SR-BI polypeptides include polypeptides having both an effector and antigenic function, or only one of such functions. SR-BI polypeptides include antagonist polypeptides and native SR-BI polypeptides, provided that such antagonists include an epitope of a native SR-BI polypeptide. An effector function of SR-BI polypeptide can be the ability to bind to a ligand, e.g., a lipid or modified form thereof.

As used herein the term "bioactive fragment of a SR-BI protein" refers to a fragment of a full-length SR-BI protein, wherein the fragment specifically mimics or antagonizes the activity of a wild-type SR-BI protein. The bioactive fragment preferably is a fragment capable of binding to a second molecule, such as a ligand.

The term "an aberrant activity" or "abnormal activity", as applied to an activity of a protein such as SR-BI, refers to an activity which differs from the activity of the wild-type or native protein or which differs from the activity of the protein in a healthy subject, e.g., a subject not afflicted with a disease associated with a specific allelic variant of an SR-BI polymorphism. An activity of a protein can be aberrant because it is stronger than the activity of its native counterpart. Alternatively, an activity can be aberrant because it is weaker or absent related to the activity of its native counterpart. An aberrant activity can also be a change in an activity. For example an aberrant protein can interact with a different protein relative to its native counterpart. A cell can have an aberrant SR-BI activity due to overexpression or underexpression of the gene encoding SR-BI. An aberrant SR-BI activity can result, e.g., from a mutation in the gene, which results, e.g., in lower or higher binding affinity of a lipid to the SR-BI protein encoded by the mutated gene. An aberrant SR-BI activity can also result from a lower or higher level of SR-BI receptor on cells, which can result, e.g., from a mutation in the 5' flanking region of the SR-BI gene or any other regulatory element of the SR-BI gene, such as a regulatory element located in an intron. Accordingly, an aberrant SR-BI activity can result from an abnormal SR-BI promoter activity.

The terms "abnormal SR-BI promoter activity", "aberrant SR-BI promoter activity", "abnormal SR-BI transcriptional activity" and "aberrant SR-BI transcriptional activity", which are used interchangeably herein, refer to the transcriptional activity of an SR-BI promoter which differs from the transcriptional activity of the same promoter in a healthy subject. An abnormal SR-BI activity can result from a higher or lower transcriptional activity than that in a healthy subject. An aberrant SR-BI promoter activity can result, e.g., from the presence of a genetic lesion in a regulatory element, such as in a regulatory element located in the promoter. An "aberrant SR-BI promoter activity" is also intended to refer to the transcriptional activity of an SR-BI promoter which is functional (capable of inducing transcription of a gene to which it is operably linked) in tissues or cells in which the "natural" or wild-type SR-BI promoter is not functional or which is non functional in tissues or cells in which the "natural" or wild-type SR-BI promoter is functional. Thus, a tissue distribution of SR-BI in a subject which differs from the tissue distribution of SR-BI in a "normal" or "healthy" subject, can be the result of an abnormal transcriptional activity from the SR-BI promoter region. Such an abnormal transcriptional activity can result, e.g., from one or more mutations in a promoter region, such as in a regulatory element thereof. An abnormal transcriptional activity can also result from a mutation in a transcription factor involved in the control of SR-BI gene expression.

The term "body mass index" or "BMI" refers to the ratio of weight (kg)/height (m)$^2$ and can be used to define whether a subject is overweight. Typically, a subject is underweight if he has a BMI<20; normal if he has a BMI of 20–25, overweight if he has a BMI of 25–30, obese if he has a BMI of 30–40 and severely obese if he has a BMI>40.

As used herein, a subject has an "abnormal body mass" or "abnormal body mass index" or "aberrant body mass" or "aberrant body mass index" if his body mass index is outside the range defined for a healthy or normal subject, i.e., BMI of 20–25. A disorder of body mass include any disorder affecting the body mass of a subject such that his body mass is outside the normal range. For example, obesity is a disorder of body mass. Wasting is also a disorder of body mass. An abnormal body mass index can have a hormonal origin, e.g., in premenopausal women.

The term "cardiovascular disorder" refers to a disease or disorder of the cardiovascular system and includes ischemia, restenosis, congestive heart failure, and atherosclerosis.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during MRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term" a homolog of a nucleic acid" refers to a nucleic acid having a nucleotide sequence having a certain degree of homology with the nucleotide sequence of the nucleic acid or complement thereof. A homolog of a double stranded nucleic acid having SEQ I) NO: x is intended to include nucleic acids having a nucleotide sequence which has a certain degree of homology with SEQ ID NO: x or with the complement thereof. Preferred homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "intronic sequence" or "intronic nucleotide sequence" refers to the nucleotide sequence of an intron or portion thereof.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "lipid" shall refer to a fat or fat-like substance that is insoluble in polar solvents such as water. The term "lipid" is intended to include true fats (e.g. esters of fatty acids and glycerol); lipids (phospholipids, cerebrosides, waxes); sterols (cholesterol, ergosterol) and lipoproteins (e.g. HDL, LDL and VLDL).

The term "locus" refers to a specific position in a chromosome. For example, a locus of an SR-BI gene refers to the chromosomal position of the SR-BI gene.

The term "modulation" as used herein refers to both upregulation, (i.e., activation or stimulation), for example by agonizing; and downregulation (i.e. inhibition or suppression), for example by antagonizing of a bioactivity (e.g. expression of a gene).

The term "molecular structure" of a gene or a portion thereof refers to the structure as defined by the nucleotide content (including deletions, substitutions, additions of one or more nucleotides), the nucleotide sequence, the state of methylation, and/or any other modification of the gene or portion thereof.

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous (for that gene) subject, the mutation is said to be co-dominant.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The term "nucleotide sequence complementary to the nucleotide sequence set forth in SEQ ID NO: x" refers to the nucleotide sequence of the complementary strand of a nucleic acid strand having SEQ ID NO: x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO: x refers to the complementary strand of the strand having SEQ ID NO: x or to any nucleic acid having the nucleotide sequence of the complementary strand of SEQ ID NO: x. When referring to a single stranded nucleic acid having the nucleotide sequence SEQ ID NO: x, the complement of this nucleic acid is a nucleic acid having a nucleotide sequence which is complementary to that of SEQ ID NO: x. The nucleotide sequences and complementary sequences thereof are always given in the 5' to 3' direction. The term "complement" and "reverse complement" are used interchangeably herein.

A "non-human animal" of the invention can include mammals such as rodents, non-human primates, sheep, goats, horses, dogs, cows, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which an exogenous sequence is found, or in which an exogenous sequence is expressed in some but not all cells of the animal. The term "tissue-specific chimeric animal" indicates that an exogenous sequence is present and/or expressed or disrupted in some tissues, but not others.

The term "operably linked" is intended to mean that the promoter is associated with the nucleic acid in such a manner as to facilitate transcription of the nucleic acid from the promoter.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

A "regulatory element", also termed herein "regulatory sequence is intended to include elements which are capable of modulating transcription from a basic promoter and include elements such as enhancers and silencers. The term "enhancer", also referred to herein as "enhancer element", is intended to include regulatory elements capable of increasing, stimulating, or enhancing transcription from a basic promoter. The term "silencer", also referred to herein as "silencer element" is intended to include regulatory elements capable of decreasing, inhibiting, or repressing transcription from a basic promoter. Regulatory elements are typically present in 5' flanking regions of genes. However, regulatory elements have also been shown to be present in other regions of a gene, in particular in introns. Thus, it is possible that SR-BI genes have regulatory elements located in introns, exons, coding regions, and 3' flanking sequences. Such regulatory elements are also intended to be encompassed by the present invention and can be identified by any of the assays that can be used to identify regulatory elements in 5' flanking regions of genes.

The term "regulatory element" further encompasses "tissue specific" regulatory elements, i.e., regulatory elements which effect expression of the selected DNA sequence preferentially in specific cells (e.g., cells of a specific tissue). Gene expression occurs preferentially in a specific cell if expression in this cell type is significantly higher than expression in other cell types. The term "regulatory element" also encompasses non-tissue specific regulatory elements, i.e., regulatory elements which are active in most cell types. Furthermore, a regulatory element can be a constitutive regulatory element, i.e., a regulatory element which constitutively regulates transcription, as opposed to a regulatory element which is inducible, i.e., a regulatory element which is active primarily in response to a stimulus. A stimulus can be, e.g., a molecule, such as a hormone, cytokine, heavy metal, phorbol ester, cyclic AMP (cAMP), or retinoic acid.

Regulatory elements are typically bound by proteins, e.g., transcription factors. The term "transcription factor" is intended to include proteins or modified forms thereof, which interact preferentially with specific nucleic acid sequences, i.e., regulatory elements, and which in appropriate conditions stimulate or repress transcription. Some transcription factors are active when they are in the form of a monomer. Alternatively, other transcription factors are active in the form of a dimer consisting of two identical proteins or different proteins (heterodimer). Modified forms of transcription factors are intended to refer to transcription factors having a postranslational modification, such as the attachment of a phosphate group. The activity of a transcription factor is frequently modulated by a postranslational modification. For example, certain transcription factors are active only if they are phosphorylated on specific residues. Alternatively, transcription factors can be active in the absence of phosphorylated residues and become inactivated by phosphorylation. A list of known transcription factors and their DNA binding site can be found, e.g., in public databases, e.g., TFMATRIX Transcription Factor Binding Site Profile database.

As used herein, the term "specifically hybridizes" or "specifically detects" refers to the ability of a nucleic acid molecule of the invention to hybridize to at least approximately 6, 12, 20, 30, 40, 50, 60, 70, 80, 90, 100, 110, 120, 130 or 140 consecutive nucleotides of either strand of an SR-BI gene.

"SR-BI" or "SR-BI receptor" refers to a class B scavenger receptor that has been shown to bind HDL cholesterol and mediate uptake into cells (Acton, S. et al., *Science* 271:518–520). SR-BI has also been shown to bind with high affinity to modified proteins (e.g. acetylated LDL, oxidized LDL, maleylated bovine serum albumin) and native LDL (Acton, et al., (1994) *J. Biochem.* 269:21003–21009). Further, SR-BI has been shown to bind anionic phospholipids, such as phosphatidylserine and phosphatidylinositol, but not zwitterionic phospholipids, such as phosphatidylcholine, phosphatidylethanolamine and sphingomyelin. Competition studies suggest that anionic phospholipids bind to SR-BI at a site close to or identical with the sites of native and modified LDL binding and that the interaction may involve polyvalent binding via multiple anionic phospholipid molecules (Rigotti, A., S. Acton and M. Krieger (1995) *J. Biochem* 270:16221–16224). SR-BI has also been shown to bind to negatively charged liposomes and apoptotic cells. The human SR-BI protein is described in Calvo et al. (1993) J. Biol. Chem. 268:18929 and hamster SR-BI is described in International Patent Application Number WO 96/00288 entitled "Class B1 and C1 Scavenger Receptors" by Acton, S. et al.

The term "SR-BI therapeutic" refers to various forms of SR-BI polypeptides, as well as peptidomimetics, nucleic acids, or small molecules, which can modulate at least one activity of an SR-BI by mimicking or potentiating (agonizing) or inhibiting (antagonizing) the effects of a naturally-occurring SR-BI polypeptide. An SR-BI therapeutic which mimics or potentiates the activity of a wild-type SR-BI polypeptide is a "SR-BI agonist". Conversely, an SR-BI therapeutic which inhibits the activity of a wild-type SR-BI polypeptide is a "SR-BI antagonist". SR-BI therapeutics can be used to treat diseases which are associated with a specific SR-BI allele which encodes a protein having an amino acid sequence that differs from that of the wild-type SR-BI protein.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, or an antisense transcript, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). Alternatively, a transgene can also be present in an episome. A transgene can include one or more transcriptional regulatory sequence and any other nucleic acid, (e.g. intron), that may be necessary for optimal expression of a selected nucleic acid.

A "transgenic animal" refers to any animal, preferably a non-human animal, e.g. a mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of a protein, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

The term "treating" as used herein is intended to encompass curing as well as ameliorating at least one symptom of the condition or disease.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

Nucleic Acids of the Present Invention

As described below, one aspect of the invention pertains to isolated nucleic acids comprising an intronic sequence of an SR-BI gene. In a preferred embodiment, the invention provides an intronic sequence of the genomic DNA sequence encoding an SR-BI protein, comprising an intronic sequence shown in FIG. 2 or set forth in any of SEQ ID NOs. 1–121 or complements thereof or homologs thereof. Other preferred nucleic acids of the invention include specific SR-BI alleles, which differ from the allelic variant having the nucleotide sequence set forth in SEQ ID NO: 1 or SEQ ID NO: 3, or at least a portion thereof having a polymorphic region. Nucleic acids of the invention can function as probes or primers, e.g., in methods for determining the identity of an allelic variant of an SR-BI polymorphic region. The nucleic acids of the invention can also be used to determine whether a subject is at risk of developing a disease associated with a specific allelic variant of an SR-BI polymorphic region, e.g, a disease or disorder associated with an aberrant SR-BI activity. The nucleic acids of the invention can further be used to prepare SR-BI polypeptides encoded by specific alleles, such as mutant alleles. Such polypeptides can be used in gene therapy. Polypeptides encoded by specific SR-BI alleles, such as mutant SR-BI polypeptides, can also be used for preparing reagents, e.g., antibodies, for detecting SR-BI proteins encoded by these alleles. Accordingly, such reagents can be used to detect mutant SR-BI proteins.

Certain nucleic acids of the invention comprise an intronic sequence of an SR-BI gene. The term "SR-BI intronic sequence" refers to a nucleotide sequence of an intron of an SR-BI gene. An intronic sequence can be directly adjacent to an exon or located further away from the exons. Preferred nucleic acids of the invention include an intronic sequence of an SR-BI gene which is adjacent to an exon and comprises at least about 3 consecutive nucleotides, at least about 6 consecutive nucleotides, at least about 9 consecutive nucleotides, at least about 12 consecutive nucleotides, at least about 15 consecutive nucleotides, at least about 18 consecutive nucleotides, or at least about 20 consecutive nucleotides. Isolated nucleic acids which comprise an SR-BI intronic sequence which is immediately adjacent to an exon and comprises at least about 25 consecutive nucleotides, at least about 30 consecutive nucleotides, at least about 35 consecutive nucleotides, at least about 40 consecutive nucleotides, at least about 50 consecutive nucleotides, or at least about 100 consecutive nucleotides are also within the scope of the invention. Preferred isolated nucleic acids of the invention also include those having an SR-BI intronic sequence having a nucleotide sequence of at least about 10 nucleotides, at least about 15 nucleotides, at least about 20 nucleotides, at least about 25 nucleotides, at least about 30 nucleotides, at least about 35 nucleotides, at least about 40 nucleotides, at least about 50 nucleotides or at least about 100 nucleotides. Other preferred nucleic acids of the invention can comprise an SR-BI intronic sequence having less than about 10 nucleotides, provided that the nucleotide sequence is novel. Yet other preferred isolated nucleic acids of the invention include SR-BI intronic nucleic acid sequences of an SR-BI intron, having at least about 150 consecutive nucleotides, at least about 200 consecutive nucleotides, at least about 250 consecutive nucleotides, at least about 300 consecutive nucleotides, at least about 350 consecutive nucleotides, at least about 400 consecutive nucleotides, at least about 500 consecutive nucleotides or at least about 1000 consecutive nucleotides.

Preferred nucleic acids of the invention comprise an SR-BI intronic sequence having a nucleotide sequence shown in FIG. 2, and/or in any of SEQ ID Nos. 1–121, complement thereof, reverse complement thereof or homolog thereof. In a preferred embodiment, the invention provides an isolated nucleic acid comprising an SR-BI intronic which is at least about 70% 75%, 80%, 85%, 90%, 95%, or preferably at least about 98%, and most preferably at least about 99% identical to an intronic nucleotide sequence shown in FIG. 2 or set forth in any of SEQ ID NOS. 1–121 or a complement thereof. In fact, as described herein, several alleles of human SR-BI genes have been identified. The invention is intended to encompass all of these alleles and SR-BI alleles not yet identified, which can be identified, e.g, according to the methods described herein.

The invention also provides isolated nucleic acids comprising at least one polymorphic region of an SR-BI gene having a nucleotide sequence which differs from the nucleotide sequence set forth in SEQ ID NO: 1 or SEQ ID NO: 3. Preferred nucleic acids have a polymorphic region located in an exon of an SR-BI gene, such as exons 1, 3 or 8. Accordingly, preferred nucleic acids of the invention comprise an adenine at position 146 of exon 1 (as set forth in SEQ ID NO: 95), an adenine at position 119 of exon 3 (as set forth in SEQ ID NO: 96, and/or a thymidine at position 41 of exon 8 (as set forth in SEQ ID NO:

65). Preferred nucleic acids can also have a polymorphic region in an intron, e.g., intron 5 or 10. For example, the invention provides nucleic acids having a polymorphic nucleotide at position 54 of intron 5 and/or at position −41 of intron 10. In a preferred embodiment, the nucleic acid has a thymidine at position 54 of intron 5 (as set forth in SEQ ID NO: 66) and/or a guanine at position 41 of intron 10 (as set forth in SEQ ID NO: 97). The nucleic acids can be genomic DNA, cDNA, or RNA (in which case, the nucleic acid has a uridine at position 54 of intron 5).

Also within the scope of the invention are isolated nucleic acids which encode an SR-BI protein, such as an SR-BI protein having an amino acid sequence which differs from the amino acid sequence set forth in SEQ ID NOs 2 and 4. Preferred nucleic acids encode an SR-BI polypeptide comprising an amino acid sequence from SEQ ID NO: 2 or 4 in which residue 2 is a serine and/or in which residue 135 is an isoleucine.

Preferred nucleic acids of the invention are from vertebrate genes encoding SR-BI proteins. Particularly preferred vertebrate nucleic acids are mammalian nucleic acids. A particularly preferred nucleic acid of the invention is a human nucleic acid, such as a nucleic acid comprising an SR-BI intronic sequence shown in FIG. 2 or set forth in any of SEQ ID NOS. 1–121 or complement thereof or an allele comprising a nucleotide sequence set forth in SEQ ID NO: 65 or SEQ ID NO: 97.

Another aspect of the invention provides a nucleic acid which hybridizes under appropriate stringency to an SR-BI intronic sequence having a nucleotide sequence shown in introns shown in FIG. 2 or in intronic sequences set forth in any of SEQ ID Nos. 1–121 or complement thereof. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a preferred embodiment, a nucleic acid of the present invention will bind to at least about 20, preferably at least about 25, more preferably at least about 30 and most preferably at least about 50 consecutive nucleotides of a sequence shown in FIG. 2 or set forth in any of SEQ ID Nos. 1–121 under moderately stringent conditions, for example at about 2.0×SSC and about 40° C. Even more preferred nucleic acids of the invention are capable of hybridizing under stringent conditions to an intronic sequence of at least about 20, 30, 40, or at least about 50 nucleotides as shown in FIG. 2 or as set forth in an intronic sequence of any of SEQ ID Nos. 1–121.

Hybridization, as described above, can be used to isolate nucleic acids comprising an SR-BI intron or portion thereof from various animal species. A comparison of these nucleic acids should be indicative of intronic sequences which may have a regulatory or other function, since these regions are expected to be conserved among various species. Hybridization can also be used to isolate SR-BI alleles.

The nucleic acid of the invention can be single stranded DNA (e.g., an oligonucleotide), double stranded DNA (e.g., double stranded oligonucleotide) or RNA. Preferred nucleic acids of the invention can be used as probes or primers. Primers of the invention refer to nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes of the invention refer to nucleic acids which hybridize to the region of interest and which are not further extended. For example, a probe is a nucleic acid which hybridizes to a polymorphic region of an SR-BI gene, and which by hybridization or absence of hybridization to the DNA of a subject will be indicative of the identity of the allelic variant of the polymorphic region of the SR-BI gene.

Numerous procedures for determining the nucleotide sequence of a nucleic acid, or for determining the presence of mutations in nucleic acids include a nucleic acid amplification step, which can be carried out by, e.g., polymerase chain reaction (PCR). Accordingly, in one embodiment, the invention provides primers for amplifying portions of an SR-BI gene, such as portions of exons and/or portions of introns. In a preferred embodiment, the exons and/or sequences adjacent to the exons of the human SR-BI gene will be amplified to, e.g., detect which allelic variant of a polymorphic region is present in the SR-BI gene of a subject. Preferred primers comprise a nucleotide sequence complementary to an SR-BI intronic sequence or a specific allelic variant of an SR-BI polymorphic region and of sufficient length to selectively hybridize with an SR-BI gene. In a preferred embodiment, the primer, e.g., a substantially purified oligonucleotide, comprises a region having a nucleotide sequence which hybridizes under stringent conditions to about 6, 8, 10, or 12, preferably 25, 30, 40, 50, or 75 consecutive nucleotides of an SR-BI gene. In an even more preferred embodiment, the primer is capable of hybridizing to an SR-BI intron and has a nucleotide sequence of an intronic sequence shown in FIG. 2 or set forth in any of SEQ ID Nos. 1–121, complements thereof, allelic variants thereof, or complements of allelic variants thereof. For example, primers comprising a nucleotide sequence of at least about 15 consecutive nucleotides, at least about 20 nucleotides or having from about 15 to about 25 nucleotides shown in FIG. 2 or set forth in any of SEQ ID NOS. 1–121 or complement thereof are provided by the invention. Primers having a sequence of more than about 25 nucleotides are also within the scope of the invention. Preferred primers of the invention are primers that can be used in PCR for amplifying each of the exons of an SR-BI gene. Even more preferred primers of the invention have the nucleotide sequence set forth in any of SEQ ID Nos. 41–64 and 89–94 (see Table VII).

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified. A forward primer can be a primer having a nucleotide sequence or a portion of the nucleotide sequence shown in FIG. 2 or in SEQ ID Nos. 1–40, 65, 66, and 95–97. A reverse primer can be a primer having a nucleotide sequence or a portion of the nucleotide sequence that is complementary to a nucleotide sequence shown in FIG. 2 or in SEQ ID Nos. 1–40, 65, 66, and 95–97. Preferred forward primers comprise a nucleotide sequence set forth in SEQ ID Nos. 41, 43, 45, 47, 49, 51, 53, 55, 57, 59, 61, 63, and 85 (shown in Table IV). Preferred reverse primers comprise a nucleotide sequence set forth in SEQ ID Nos. 42, 44, 46, 48, 50, 52, 54, 56, 58, 60, 62, 64, and 86. Preferred pairs of primers for amplifying each of the exons of human SR-BI are set forth in Table IV.

Yet other preferred primers of the invention are nucleic acids which are capable of selectively hybridizing to an allelic variant of a polymorphic region of an SR-BI gene. Thus, such primers can be specific for an SR-BI gene sequence, so long as they have a nucleotide sequence which is capable of hybridizing to an SR-BI gene. Preferred primers are capable of specifically hybridizing to an allelic variant in which nucleotide 146 of exon 1 of human SR-BI is an adenine, e.g., a nucleic acid having SEQ ID NO: 95; an allelic variant in which nucleotide 119 of exon 3 is an adenine, e.g., a nucleic acid having SEQ ID NO: 96; or an allelic variant in which nucleotide 41 of exon 8 of human SR-BI is a thymidine, e.g., a nucleic acid having SEQ ID NO: 65. Other preferred primers are capable of specifically hybridizing to an allelic variant in which nucleotide 54 of intron 5 is a thymidine, e.g., a nucleic acid having SEQ ID NO: 66 or nucleotide −41 of intron 10 is a guanine, e.g., a nucleic acid having SEQ ID NO: 97. Such primers can be used, e.g., in sequence specific oligonucleotide priming as described further herein.

The SR-BI nucleic acids of the invention can also be used as probes, e.g., in therapeutic and diagnostic assays. For instance, the present invention provides a probe comprising a substantially purified oligonucleotide, which oligonucleotide comprises a region having a nucleotide sequence that hybridizes under stringent conditions to at least approximately 6, 8, 10 or 12, preferably about 25, 30, 40, 50 or 75 consecutive nucleotides of an SR-BI gene. In one embodiment, the probes preferably hybridize to an intron of an SR-BI gene, having an intronic nucleotide sequence shown in FIG. 2 or set forth in any of SEQ ID Nos. 1–121, allelic variants thereof, complements thereof or complements of allelic variants thereof. In another embodiment, the probes are capable of hybridizing to a nucleotide sequence encompassing an intron/exon border of an SR-BI gene.

Other preferred probes of the invention are capable of hybridizing specifically to a region of an SR-BI gene which is polymorphic. In an even more preferred embodiment of the invention, the probes are capable of hybridizing specifically to one allelic variant of an SR-BI gene having a nucleotide sequence which differs from the nucleotide sequence set forth in SEQ ID NO: 1 or 3. Such probes can then be used to specifically detect which allelic variant of a polymorphic region of an SR-BI gene is present in a subject. The polymorphic region can be located in the promoter, exon, or intron sequences of an SR-BI gene.

For example, preferred probes of the invention are capable of hybridizing specifically to a region overlapping nucleotide 146 of exon 1 of the human SR-BI gene. In one embodiment, the probe overlapping nucleotide 146 of exon 1 is capable of hybridizing specifically to a nucleotide sequence wherein nucleotide 146 is an adenine (as shown in SEQ ID NO: 95). Examples of such probes include a probe having the nucleotide sequence 5' GCGGAGCAGCTCATGTCTGCG 3' (SEQ ID NO: 98); 5' CTTTCGCGGAGCAGCTCATGTCTGCGCGCCT 3'(SEQ ID NO: 99); and probes having the complement of these nucleotide sequences, i.e., 5° CGCAGACATGAGCTGCTCCGC 3' (SEQ ID NO: 100); 5' AGGCGCGCAGACATGAGCTGCTCCGCCAAAG 3'(SEQ ID NO: 101). The bold nucleotides represents the location of the nucleotide polymorphism. In another embodiment, the probe overlapping nucleotide 146 of exon 1 is capable of specifically hybridizing to a nucleotide sequence wherein nucleotide 146 is a guanine (as shown in FIG. 2 and set forth in SEQ ID NO: 5). Examples of such probes include a probe having the nucleotide sequence 5' GCGGAGCAGCGCATGTCTGCG 3' (SEQ ID NO: 102); CTTTCGCGGAGCAGCGCATGTCTGCGCGCCT 3' (SEQ ID NO: 103) and probes having the complement of these nucleotide sequences, i.e., 5' CGCAGACATGCGCTGCTCCGC 3' (SEQ ID NO: 104); 5' AGGCGCGCAGACATGCGCTGCTCCGCCAAAG 3' (SEQ ID NO: 105).

Preferred probes of the invention are capable of hybridizing specifically to a region overlapping nucleotide 119 of exon 3 of the human SR-BI gene. In one embodiment, the probe overlapping nucleotide 119 of exon 3 is capable of hybridizing specifically to a nucleotide sequence wherein nucleotide 119 is an adenine (as shown in SEQ ID NO: 96). Examples of such probes include a probe having the nucleotide sequence 5' TTGGGCATGATGATGTAGACG 3' (SEQ ID NO: 106); 5' GGATGTTGGGCATGATGATGTA-GACGCTCTC 3' (SEQ ID NO: 107); and probes having the complement of these nucleotide sequences, i.e., 5' CGAC-TACATCATCATGCCCAA 3' (SEQ ID NO: 108); 5' GAGAGCGACTACATCATCATGCCCAACATCC 3' (SEQ ID NO: 109). The bold nucleotides represents the location of the nucleotide polymorphism. In another embodiment, the probe overlapping nucleotide 119 of exon 3 is capable of specifically hybridizing to a nucleotide sequence wherein nucleotide 119 is a guanine (as shown in FIG. 2 and set forth in SEQ ID NO: 7). Examples of such probes include a probe having the nucleotide sequence 5' TTGGGCATGAGGAT-GTAGACG 3' (SEQ ID NO: 110); GGATGTTGGGCAT-GAGGATGTAGACGCTCTC 3' (SEQ ID NO: 111) and probes having the complement of these nucleotide sequences, i.e., 5' CGACTACATCCTCATGCCCAA 3' (SEQ ID NO: 112); 5' GAGAGCGACTACATCCATCAT-GCCCAACATCC 3' (SEQ ID NO: 113).

Other preferred probes of the invention are capable of hybridizing specifically to a region overlapping nucleotide 41 of exon 8 of the human SR-BI gene. In one embodiment, the probe overlapping nucleotide 41 of exon 8 is capable of hybridizing specifically to a nucleotide sequence wherein nucleotide 41 is a thymidine (as shown in SEQ ID NO: 65). Examples of such probes include a probe having the nucleotide sequence 5' AACCGGGTCAGCGTTGAGGA 3' (SEQ ID NO: 67); 5' TGCCAGAACCGGGTCAGCGT-TGAGGAAGTGA 3' (SEQ ID NO: 68); and probes having the complement of these nucleotide sequences, i.e., 5'TCCT-CAACGCTGACCCGGTT 3' (SEQ ID NO: 69); 5' TCACT-TCCTCAACGCTGACCCGGTTCTGGCA 3' (SEQ ID NO: 70). The bold nucleotides represents the location of the nucleotide polymorphism. In another embodiment, the probe overlapping nucleotide 41 of exon 8 is capable of specifically hybridizing to a nucleotide sequence wherein nucleotide 41 is a cytidine (as shown in FIG. 2 and set forth in SEQ ID NO: 12). Examples of such probes include a probe having the nucleotide sequence 5' AACCGGGTCG-GCGTTGATGA 3' (SEQ ID NO: 71); TGCCAGAAC-CGGGTCGGCGT TGATGAAGTGA 3' (SEQ ID NO: 72) and probes having the complement of these nucleotide sequences, i.e., 5' TCATCAACGCCGACCCGGTT 3' (SEQ ID NO: 73); 5' TCACTTCATCAACGCCGACCCGGT-TCTGGCA 3' (SEQ ID NO: 74).

Yet other preferred probes of the invention are capable of hybridizing specifically to a region overlapping nucleotide 54 of intron 5 of the human SR-BI gene. In one embodiment, the probe overlapping nucleotide 54 of intron 5 is capable of hybridizing specifically to a nucleotide sequence wherein nucleotide 54 is a cytidine (as shown in FIG. 2 and set forth in SEQ ID NOS. 9 and 26). Examples of such probes include a probe having the nucleotide sequence 5' AGCCATGGC-CGGGCCCACCCT 3'(SEQ ID NO: 75); 5' CGAGCAGC-CATG GCCGGGCCCACCCTCCCCT 3' (SEQ ID NO: 76); and probes having the complement of these nucleotide sequences, i.e., 5'AGGGTGGGCCCGGCCATGGCT 3' (SEQ ID NO: 77); 5'AGGGGAGGGTGGGCCCGGC-CATGGCTGCTCG 3' (SEQ ID NO: 78). In another embodiment, the probe overlapping nucleotide 54 of intron 5 is capable of specifically hybridizing to a nucleotide sequence wherein nucleotide 54 is a thymidine (as shown in SEQ ID NO: 66). Examples of such probes include a probe having the nucleotide sequence 5' AGCCATGGCCAGGC-CCACCCT 3' (SEQ ID NO: 79); 5° CGAGCAGCCATG-GCCAG GCCCACCCTCCCCT 3' (SEQ ID NO: 80); and probes having the complement of these nucleotide sequences, i.e., 5' AGGGTGGGCCTGGCCATGGCT 3' (SEQ ID NO: 81); 5' AGGGGAGGGTGGGCCTGGC-CATGGCTGCTCG 3' (SEQ ID NO: 82).

Still other preferred probes of the invention are capable of hybridizing specifically to a region overlapping nucleotide −41 of intron 10 of the human SR-BI gene. In one embodiment, the probe overlapping nucleotide −41 of intron 10 is capable of hybridizing specifically to a nucleotide sequence wherein nucleotide −41 is a guanine (as shown in SEQ ID NO: 97). Examples of such probes include a probe having the nucleotide sequence 5' TGGGGCCGCACGCT-GCGGGCT 3' (SEQ ID NO: 114); 5' TGAGCTGGGGC-CGCACGCTGCGGGCTACAGC 3' (SEQ ID NO: 115); and probes having the complement of these nucleotide sequences, i.e., 5' AGCCCGCAGCGTGCGGCCCCA 3' (SEQ ID NO: 116); 5' GCTGTAGCCCGCAGCGTGCG-GCCCCAGCTCA 3' (SEQ ID NO: 117). The bold nucleotides represents the location of the nucleotide polymorphism. In another embodiment, the probe overlapping nucleotide −41 of intron 10 is capable of specifically hybridizing to a nucleotide sequence wherein nucleotide −41 is a cytidine (as shown in FIG. 2 and set forth in SEQ ID NO: 15). Examples of such probes include a probe having the nucleotide sequence 5' TGGGGCCGCAGGCTGCGGGCT 3' (SEQ ID NO: 118); TGAGCTGGGGCCGCAGGCT-GCGGGCTACAGC 3'(SEQ ID NO: 119) and probes having the complement of these nucleotide sequences, i.e., 5' AGC-CCGCAGCCTGCGGCCCCA 3'(SEQ ID NO: 120); 5' GCTGTAGCCCGCAGCCTGCGGCCCCAGCTCA 3 (SEQ ID NO: 121).

Particularly, preferred probes of the invention have a number of nucleotides sufficient to allow specific hybridization to the target nucleotide sequence. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of an SR-BI gene may first be amplified and thus isolated from the rest of the chromosomal DNA and then hybridized to a probe. In such a situation, a shorter probe will likely provide sufficient specificity of hybridization. For example, a probe having a nucleotide sequence of about 10 nucleotides may be sufficient.

In preferred embodiments, the probe or primer fuirther comprises a label attached thereto, which, e.g., is capable of being detected, e.g. the label group is selected from amongst radioisotopes, fluorescent compounds, enzymes, and enzyme co-factors.

In a prefeffed embodiment of the invention, the isolated nucleic acid, which is used, e.g., as a probe or a primer, is modified, such as to become more stable. Exemplary nucleic acid molecules which are modified include phosphoramidate, phosphothioate and methylphosphonate analogs of DNA (see also U.S. Pat. Nos. 5,176,996; 5,264,564; and 5,256,775).

The nucleic acids of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988), hybridization-triggered cleavage agents. (See, e.g., Krol et al., 1988, *Bio Techniques* 6:958–976) or intercalating agents. (See, e.g., Zon, 1988, Pharm. Res. 5:539–549). To this end, the nucleic acid of the invention may be conjugated to another molecule, e.g., a peptide, hybridization triggered cross-linking agent, transport agent, hybridization-triggered cleavage agent, etc.

The isolated nucleic acid comprising an SR-BI intronic sequence may comprise at least one modified base moiety which is selected from the group including but not limited to 5-fluorouracil, 5-bromouracil, 5-chlorouracil, 5-iodouracil, hypoxanthine, xantine, 4-acetylcytidine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytidine, 5-methylcytidine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytidine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The isolated nucleic acid may also comprise at least one modified sugar moiety selected from the group including but not limited to arabinose, 2-fluoroarabinose, xylulose, and hexose.

In yet another embodiment, the nucleic acid comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the nucleic acid is an α-anomeric oligonucleotide. An α-anomeric oligonucleotide forms specific double-stranded hybrids with complementary RNA in which, contrary to the usual P-units, the strands run parallel to each other (Gautier et al., 1987, *Nucl Acids Res.* 15:6625–6641). The oligonucleotide is a 2'-0-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Any nucleic acid fragment of the invention can be prepared according to methods well known in the art and described, e.g., in Sambrook, J. Fritsch, E. F., and Maniatis, T. (1989) *Molecular Cloning: A Laboratory Manual*, Cold Spring Harbor Laboratory Press, Cold Spring Harbor, N.Y. For example, discrete fragments of the DNA can be prepared and cloned using restriction enzymes. Alternatively, discrete fragments can be prepared using the Polymerase Chain Reaction (PCR) using primers having an appropriate sequence.

Oligonucleotides of the invention may be synthesized by standard methods known in the art, e.g by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

The invention also provides vectors and plasmids containing the nucleic acids of the invention. For example, in one embodiment, the invention provides a vector comprising at least a portion of an SR-BI gene comprising a polymorphic region and/or intronic sequence. Thus, the invention provides vectors for expressing at least a portion of the newly identified allelic variants of the human SR-BI gene, as well as other allelic variants, having a nucleotide sequence which is different from the nucleotide sequence disclosed in Calvo and Vega, supra. The allelic variants can be expressed in eukaryotic cells, e.g., cells of a subject, or in prokaryotic cells.

In one embodiment, the vector comprising at least a portion of an SR-BI allele is introduced into a host cell, such that a protein encoded by the allele is synthesized. The SR-BI protein produced can be used, e.g., for the production of antibodies, which can be used, e.g., in methods for detecting mutant forms of SR-BI. Alternatively, the vector can be used for gene therapy, and be, e.g., introduced into a subject to produce SR-BI protein. Host cells comprising a vector having at least a portion of an SR-BI gene are also within the scope of the invention.

Polypeptides of the present invention

The present invention makes available isolated SR-BI polypeptides, such as SR-BI polypeptides which are encoded by specific allelic variants of SR-BI, such as those identified herein. Accordingly, preferred SR-BI polypeptides of the invention have an amino acid sequence which differs from SEQ ID NOs 2 and 4. In one embodiment, the SR-BI polypeptides are isolated from, or otherwise substantially free of other cellular proteins. The term "substantially free of other cellular proteins" (also referred to herein as "contaminating proteins") or "substantially pure or purified preparations" are defined as encompassing preparations of SR-BI polypeptides having less than about 20% (by dry weight) contaminating protein, and preferably having less than about 5% contaminating protein. Functional forms of the subject polypeptides can be prepared, for the first time, as purified preparations by using a cloned gene as described herein.

Preferred SR-BI proteins of the invention have an amino acid sequence which is at least about 60%, 70%, 80%, 85%, 90%, or 95% identical or homologous to an amino acid sequence of SEQ ID NO. 2 or 4. Even more preferred SR-BI proteins comprise an amino acid sequence which is at least about 97, 98, or 99% homologous or identical to an amino acid sequence of SEQ ID NO. 2 or 4. Such proteins can be recombinant proteins, and can be, e.g., produced in vitro from nucleic acids comprising a specific allele of an SR-BI polymorphic region. For example, recombinant polypeptides preferred by the present invention can be encoded by a nucleic acid, which is at least 85% homologous and more preferably 90% homologous and most preferably 95% homologous with a nucleotide sequence set forth in SEQ ID NO. 1 or 3, and comprises an allele of a polymorphic region that differs from that set forth in SEQ ID Nos. 1 and 3. Polypeptides which are encoded by a nucleic acid that is at least about 98–99% homologous with the sequence of SEQ ID NO: 1 or 3 and comprises an allele of a polymorphic region that differs from that set forth in SEQ ID Nos. 1 and 3 are also within the scope of the invention.

In a preferred embodiment, an SR-BI protein of the present invention is a mammalian SR-BI protein. In an even more preferred embodiment, the SR-BI protein is a human protein, such as an SR-BI polypeptide comprising an amino acid sequence from SEQ ID NO.2 in which amino acid 2 is a serine and/or amino acid 135 is an isoleucine. Other preferred SR-BI polypeptides comprise an amino acid sequence from SEQ ID NO. 4 in which amino acid 2 is a serine.

SR-BI polypeptides preferably are capable of functioning in one of either role of an agonist or antagonist of at least one biological activity of a wild-type ("authentic") SR-BI protein of the appended sequence listing. The term "evolutionarily related to", with respect to amino acid sequences of SR-BI proteins, refers to both polypeptides having amino acid sequences which have arisen naturally, and also to mutational variants of human SR-BI polypeptides which are derived, for example, by combinatorial mutagenesis.

Full length proteins or fragments corresponding to one or more particular motifs and/or domains or to arbitrary sizes, for example, at least 5, 10, 25, 50, 75 and 100, amino acids in length are within the scope of the present invention.

Isolated peptidyl portions of SR-BI proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an SR-BI polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") SR-BI protein.

In general, polypeptides referred to herein as having an activity (e.g., are "bioactive") of an SR-BI protein are defined as polypeptides which which mimic or antagonize all or a portion of the biological/biochemical activities of an SR-BI protein having SEQ ID NOs 2 or 4, such as the ability to bind lipids. Other biological activities of the subject SR-BI proteins are described herein or will be reasonably apparent to those skilled in the art. According to the present invention, a polypeptide has biological activity if it is a specific agonist or antagonist of a naturally-occurring form of an SR-BI protein.

Assays for determining whether an SR-BI protein or variant thereof, has one or more biological activities are well known in the art.

Other preferred proteins of the invention are those encoded by the nucleic acids set forth in the section pertaining to nucleic acids of the invention. In particular, the invention provides fusion proteins, e.g., SR-BI-immunoglobulin fusion proteins. Such fusion proteins can provide, e.g., enhanced stability and solubility of SR-BI proteins and may thus be useful in therapy. Fusion proteins can also be used to produce an immunogenic fragment of an SR-BI protein. For example, the VP6 capsid protein of rotavirus can be used as an immunologic carrier protein for portions of the SR-BI polypeptide, either in the monomeric form or in the form of a viral particle. The nucleic acid sequences corresponding to the portion of a subject SR-BI protein to which antibodies are to be raised can be incorporated into a fusion gene construct which includes coding sequences for a late vaccinia virus structural protein to produce a set of recombinant viruses expressing fusion proteins comprising SR-BI epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an SR-BI protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple antigen peptide system for peptide-based immunization can also be utilized to generate an immunogen, wherein a desired portion of an SR-BI polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of SR-BI proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the SR-BI polypeptides of the present invention. For example, SR-BI polypeptides can be generated as glutathione—S—transferase (GST-fusion) proteins. Such GST-fusion proteins can enable easy purification of the SR-BI polypeptide, as for example by the use of glutathione-derivatized matrices (see, for example, Current Protocols in Molecular Biology, eds. Ausubel et al. (N.Y.: John Wiley & Sons, 1991)).

The present invention further pertains to methods of producing the subject SR-BI polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant SR-BI polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant SR-BI polypeptide is a fusion protein containing a domain which facilitates its purification, such as GST fusion protein.

Moreover, it will be generally appreciated that, under certain circumstances, it may be advantageous to provide homologs of one of the subject SR-BI polypeptides which function in a limited capacity as one of either an SR-BI agonist (mimetic) or an SR-BI antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of SR-BI proteins.

Homologs of each of the subject SR-BI proteins can be generated by mutagenesis, such as by discrete point mutation(s), or by truncation. For instance, mutation can give rise to homologs which retain substantially the same, or merely a subset, of the biological activity of the SR-BI polypeptide from which it was derived. Alternatively, antagonistic forms of the protein can be generated which are able to inhibit the function of the naturally occurring form of the protein, such as by competitively binding to an SR-BI receptor.

The recombinant SR-BI polypeptides of the present invention also include homologs of SR-BI polypeptides which differ from the SR-BI proteins having SEQ ID NO.2 or 4, such as versions of those protein which are resistant to proteolytic cleavage, as for example, due to mutations which alter ubiquitination or other enzymatic targeting associated with the protein.

SR-BI polypeptides may also be chemically modified to create SR-BI derivatives by forming covalent or aggregate conjugates with other chemical moieties, such as glycosyl groups, lipids, phosphate, acetyl groups and the like. Covalent derivatives of SR-BI proteins can be prepared by linking the chemical moieties to functional groups on amino acid sidechains of the protein or at the N-terminus or at the C-terminus of the polypeptide.

Modification of the structure of the subject SR-BI polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the SR-BI polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed. by L. Stryer, WH Freeman and Co.: 1981). Whether a change in the amino acid sequence of a peptide results in a functional SR-BI homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

Kits

As set forth herein, the invention provides methods, e.g., diagnostic and therapeutic methods, e.g., for determining the type of allelic variant of a polymorphic region present in an SR-BI gene, such as a human SR-BI gene. In preferred embodiments, the methods use probes or primers comprising nucleotide sequences which are complementary to an SR-BI intronic sequence or to a polymorphic region of an SR-BI gene. Accordingly, the invention provides kits for performing these methods.

In a preferred embodiment, the invention provides a kit for determining whether a subject has or is at risk of developing a disease or condition associated with a specific allelic variant of an SR-BI polymorphic region. In an even more preferred embodiment, the disease or disorder is characterized by an abnormal SR-BI activity. In an even more preferred embodiment, the invention provides a kit for determining whether a subject has or is at risk of developing a cardiovascular disease, e.g., ischemia, restenosis, congestive heart failure, atherosclerosis, aberrant lipid (e.g., cholesterol), lipoprotein (e.g., HDL, LDL) or triglyceride levels, gallstone formation, or an abnormal body mass index, e.g, obesity or cachexia. A preferred kit provides reagents for determining whether a female subject is likely to develop high LDL levels or a high BMI or whether a male subject is likely to develop low HDL levels.

Preferred kits comprise at least one probe or primer which is capable of specifically hybridizing to an SR-BI sequence or polymorphic region and instructions for use. The kits preferably comprise at least one of the above described nucleic acids, e.g., including nucleic acids hybridizing to an exon/intron border. Preferred kits for amplifying at least a portion of an SR-BI gene, e.g., an exon, comprise two primers, at least one of which is capable of hybridizing to an SR-BI intronic sequence or an allelic variant sequence. Even more preferred kits comprise a pair of primers selected from the group consisting of SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 53 and SEQ ID NO: 54, SEQ ID NO: 55 and SEQ ID NO: 56, SEQ ID NO: 57 and SEQ ID NO: 58, SEQ ID NO: 59 and SEQ ID NO: 60, SEQ ID NO: 61 and SEQ ID NO: 62, SEQ ID NO:63 and SEQ ID NO: 64, SEQ ID NO: 85 and SEQ ID NO: 86, SEQ ID NO:89 and SEQ ID NO: 90, SEQ ID NO:91 and SEQ ID NO: 92, and SEQ ID NO:93 and SEQ ID NO: 94.

The kits of the invention can also comprise one or more control nucleic acids or reference nucleic acids, such as nucleic acids comprising an SR-BI intronic sequence. For example, a kit can comprise primers for amplifying a polymorphic region of an SR-BI gene and a control DNA corresponding to such an amplified DNA and having the nucleotide sequence of a specific allelic variant. Thus, direct comparison can be performed between the DNA amplified from a subject and the DNA having the nucleotide sequence of a specific allelic variant. In one embodiment, the control nucleic acid comprises at least a portion of an SR-BI gene of an individual, who does not have a cardiovascular disease, aberrant lipid levels, gallstones, or a disease or disorder associated with an aberrant SR-BI activity.

Yet other kits of the invention comprise at least one reagent necessary to perform the assay. For example, the kit can comprise an enzyme. Alternatively the kit can comprise a buffer or any other necessary reagent.

Predictive Medicine

The invention further features predictive medicines, which are based, at least in part, on determination of the identity of SR-BI polymorphic regions which are associated with specific diseases or disorders.

For example, information obtained using the diagnostic assays described herein (alone or in conjunction with information on another genetic defect, which contributes to the same disease) is useful for diagnosing or confirming that a symptomatic subject has an allele of a polymorphic region which is associated with a particular disease or disorder. Alternatively, the information (alone or in conjunction with information on another genetic defect, which contributes to the same disease) can be used prognostically for predicting whether a non-symptomatic subject is likely to develop a disease or condition, which is associated with one or more specific alleles of SR-BI polymorphic regions in a subject. Based on the prognostic information, a doctor can recommend a regimen (e.g. diet or exercise) or therapeutic protocol, useful for preventing or prolonging onset of the particular disease or condition in the individual.

In addition, knowledge of the identity of a particular SR-BI allele in an individual (the SR-BI genetic profile), alone or in conjunction with information on other genetic defects contributing to the same disease (the genetic profile of the particular disease) allows customization of therapy for a particular disease to the individual's genetic profile, the goal of "pharmacogenomics". For example, an individual's SR-BI genetic profile or the genetic profile of a disease or condition associated with a specific allele of an SR-BI polymorphic region, can enable a doctor: 1) to more effectively prescribe a drug that will address the molecular basis of the disease or condition; and 2) to better determine the appropriate dosage of a particular drug. For example, the expression level of SR-BI proteins, alone or in conjunction with the expression level of other genes, known to contribute to the same disease, can be measured in many patients at various stages of the disease to generate a transcriptional or expression profile of the disease. Expression patterns of individual patients can then be compared to the expression profile of the disease to determine the appropriate drug and dose to administer to the patient.

The ability to target populations expected to show the highest clinical benefit, based on the SR-BI or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of SR-BI as a marker is useful for optimizing effective dose).

These and other methods are described in further detail in the following sections.

Prognostic and Diagnostic Assays

The present methods provide means for determining if a subject has (diagnostic) or is at risk of developing (prognostic) a disease, condition or disorder that is associated a specific SR-BI allele, e.g., a body mass disorder or an abnormal lipid level (HDL and LDL) and disorders resulting therefrom.

The present invention provides methods for determining the molecular structure of an SR-BI gene, such as a human SR-BI gene, or a portion thereof. In one embodiment, determining the molecular structure of at least a portion of an SR-BI gene comprises determining the identity of the allelic variant of at least one polymorphic region of an SR-BI gene. A polymorphic region of an SR-BI gene can be located in an exon, an intron, at an intron/exon border, or in the promoter of the SR-BI gene.

The invention provides methods for determining whether a subject has, or is at risk of developing, a disease or condition associated with a specific allelic variant of a polymorphic region of an SR-BI gene. Such diseases can be associated with an aberrant SR-BI activity, e.g., abnormal binding to a lipid, or an aberrant SR-BI protein level. An aberrant SR-BI protein level can result from an aberrant transcription or post transcriptional regulation. Thus, allelic differences in specific regions of an SR-BI gene can result in differences of SR-BI protein due to differences in regulation of expression. In particular, some of the identified polymorphisms in the human SR-BI gene may be associated with differences in the level of transcription, RNA maturation, splicing, or translation of the SR-BI gene or transcription product.

Analysis of one or more SR-BI polymorphic region in a subject can be useful for predicting whether a subject has or is likely to develop a body mass disorder, an abnormal lipoprotein or lipid level and disorders resulting therefrom, such as cardiovascular disorders, diabetes and gallstone formation.

In addition, since SR-BI is a receptor that is capable of binding to various lipid related molecules, it is likely that specific alleles of the SR-BI gene are associated with other diseases or conditions involving an inappropriate lipid transfer or metabolism, e.g., atherosclerosis or a biliary disorder, such as gallstone formation. Accordingly, the invention provides diagnostic and prognostic assays for determining whether a subject is at risk of developing a disease characterized by an abnormal lipid level, e.g, atherosclerosis or gall stone formation.

In preferred embodiments, the methods of the invention can be characterized as comprising detecting, in a sample of cells from the subject, the presence or absence of a specific allelic variant of one or more polymorphic regions of an SR-BI gene. The allelic differences can be: (i) a difference in the identity of at least one nucleotide or (ii) a difference in the number of nucleotides, which difference can be a single nucleotide or several nucleotides. The invention also provides methods for detecting differences in SR-BI genes such as chromosomal rearrangements, e.g., chromosomal dislocation. The invention can also be used in prenatal diagnostics.

A preferred detection method is allele specific hybridization using probes overlapping the polymorphic site and having about 5, 10, 20, 25, or 30 nucleotides around the polymorphic region. Examples of probes for detecting specific allelic variants of the polymorphic region located in exon 1 are probes comprising a nucleotide sequence set forth in any of SEQ ID NO: 98–105; probes for detecting specific allelic variants of the polymorphic region located in exon 3 are probes comprising a nucleotide sequence set forth in any of SEQ ID NO: 106–113; and probes for detecting specific allelic variants of the polymorphic region located in exon 8 are probes comprising a nucleotide sequence set forth in any of SEQ ID NO: 67–74. Examples of probes for detecting specific allelic variants of the polymorphic region located in intron 5 are probes comprising a nucleotide sequence set forth in any of SEQ ID NO: 75–82; and probes for detecting specific allelic variants of the polymorphic region located in intron 10 are probes comprising a nucleotide sequence set forth in any of SEQ ID NO: 114–121. In a preferred embodiment of the invention, several probes capable of hybridizing specifically to allelic variants are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment. For example, the identity of the allelic variant of the nucleotide polymorphism in exons 1, 3, 8 or in introns 5 and 10 can be determined in a single hybridization experiment.

In other detection methods, it is necessary to first amplify at least a portion of an SR-BI gene prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA. In preferred embodiments, the primers are located between 150 and 350 base pairs apart. Preferred primers, such as primers for amplifying each of the exons of the human SR-BI gene, are listed in Table VI in the Examples. Details regarding the PCR reaction are indicated in Table V, also in the Examples.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, any of a variety of sequencing reactions known in the art can be used to directly sequence at least a portion of an SR-BI gene and detect allelic variants, e.g., mutations, by comparing the sequence of the sample sequence with the corresponding wild-type (control) sequence. Exemplary sequencing reactions include those based on techniques developed by Maxam and Gilbert (*Proc. Natl Acad Sci USA* (1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including sequencing by mass spectrometry (see, for example, U.S. Pat. No. 5,547,835 and international patent application Publication Number WO 94/16101, entitled *DNA Sequencing by Mass Spectrometry* by H. Koster; U.S. Pat. No. 5,547,835 and international patent application Publication Number WO 94/21822 entitled "DNA Sequencing by Mass Spectrometry Via Exonuclease Degradation" by H. Koster), and U.S. Pat. No. 5,605,798 and International Patent Application No. PCT/US96/03651 entitled DNA *Diagnostics Based on Mass Spectrometry* by H. Koster;. Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing". In some cases, the presence of a specific allele of an SR-BI gene in DNA from a subject can be shown by restriction enzyme analysis. For example, a specific nucleotide polymorphism can result in a nucleotide sequence comprising a restriction site which is absent from the nucleotide sequence of another allelic variant. In particular, the presence of a cytidine at position 54 of intron 5 creates an ApaI site, whereas the presence of a thymidine, at this position destroys the ApaI site. Similarly, the polylmorphism of exon 1 and exon 8 can be determined by analyzing the products or restriction digests (see Table VI).

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) *Science* 230:1242). In general, the technique of "mismatch cleavage" starts by providing heteroduplexes formed by hybridizing a control nucleic acid, which is optionally labeled, e.g., RNA or DNA, comprising a nucleotide sequence of an SR-BI allelic variant with a sample nucleic acid, e.g, RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, Cotton et al (1988) *Proc. Natl Acad Sci USA* 85:4397; Saleeba et al (1992) Methods Enzymod. 217:286–295. In a preferred embodiment, the control or sample nucleic acid is labeled for detection.

In other embodiments, alterations in electrophoretic mobility is used to identify the type of SR-BI allelic variant. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the identity of an allelic variant of a polymorphic region is obtained by analyzing the movement of a nucleic acid comprising the polymorphic region in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al (1989) Proc. Natl Acad. Sca USA 86:6230; and Wallace et al. (1979) Nucl. Acids Res. 6:3543). Such allele specific oligonucleotide hybridization techniques may be used for the simultaneous detection of several nucleotide changes in different polymorphic regions of SR-BI. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238; Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al (1992) Mol. Cell Probes 6: 1).

In another embodiment, identification of the allelic variant is carried out using an oligonucleotide ligation assay (OLA), as described, e.g., in U.S. Pat. No. 4,998,617 and in Landegren, U. et al., Science 241:1077–1080 (1988). The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA.

Several techniques based on this OLA method have been developed and can be used to detect specific allelic variants of a polymorphic region of an SR-BI gene. For example, U.S. Pat. No. 5593826 discloses an OLA using an oligonucleotide having 3'-amino group and a 5'-phosphorylated oligonucleotide to form a conjugate having a phosphoramidate linkage. In another variation of OLA described in Tobe et al. ((1996)Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in an SR-BI gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A. -C., et al., Genomics 8:684–692 (1990); Kuppuswamy, M. N. et al., Proc. Natl. Acad. Sci. (U.S.A.) 88: 1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al., Amer. J. Hum. Genet. 52:46–59 (1993)).

For determining the identity of the allelic variant of a polymorphic region located in the coding region of an SR-BI gene, yet other methods than those described above can be used. For example, identification of an allelic variant which encodes a mutated SR-BI protein can be performed by using an antibody specifically recognizing the mutant protein in, e.g., immunohistochemistry or immunoprecipitation. Antibodies to wild-type SR-BI protein are described, e.g, in Acton et al. (1999) Science 271:518 (anti-mouse SR-BI antibody cross-reactive with human SR-BI). Other antibodies to wild-type SR-BI or mutated forms of SR-BI proteins can be prepared according to methods known in the art. Preferred antibodies specifically bind to a human SR-BI protein having a serine at residue 2 and/or having an isoleucine at amino acid residue 135. Alternatively, one can also measure an activity of an SR-BI protein, such as binding to a lipid or lipoprotein. Binding assays are known in the art and involve, e.g., obtaining cells from a subject, and performing binding experiments with a labeled lipid, to determine whether binding to the mutated form of the receptor differs from binding to the wild-type of the receptor.

Antibodies directed against wild type or mutant SR-BI polypeptides or allelic variant thereof, which are discussed above, may also be used in disease diagnostics and prognostics. Such diagnostic methods, may be used to detect abnormalities in the level of SR-BI polypeptide expression, or abnormalities in the structure and/or tissue, cellular, or subcellular location of an SR-BI polypeptide. Structural differences may include, for example, differences in the size, electronegativity, or antigenicity of the mutant SR-BI polypeptide relative to the normal SR-BI polypeptide. Protein from the tissue or cell type to be analyzed may easily be detected or isolated using techniques which are well known to one of skill in the art, including but not limited to western blot analysis. For a detailed explanation of methods for carrying out Western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of SR-BI polypeptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the SR-BI polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-SR-BI polypeptide specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay, CRC Press, Boca Raton, Fla.,* 1980; Ishikawa, et al., (eds.) Enzyme Immunoassay, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a gene or gene product or polymorphic variants can be used to monitor the course of treatment or therapy.

If a polymorphic region is located in an exon, either in a coding or non-coding portion of the gene, the identity of the allelic variant can be determined by determining the molecular structure of the MRNA, pre-mRNA, or cDNA. The molecular structure can be determined using any of the above described methods for determining the molecular structure of the genomic DNA, e.g., sequencing and SSCP.

The methods described herein may be performed, for example, by utilizing pre-packaged diagnostic kits, such as those described above, comprising at least one probe or primer nucleic acid described herein, which may be conveniently used, e.g., to determine whether a subject has or is at risk of developing a disease associated with a specific SR-BI allelic variant.

Sample nucleic acid for using in the above-described diagnostic and prognostic methods can be obtained from any cell type or tissue of a subject. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Pharmacogenomics

Knowledge of the identity of the allele of one or more SR-BI gene polymorphic regions in an individual (the SR-BI genetic profile), alone or in conjunction with information on other genetic defects contributing to the same disease (the genetic profile of the particular disease) allows a customization of the therapy for a particular disease to the individual's genetic profile, the goal of "pharmacogenomics". For example, subjects having a specific allele of an SR-BI gene may or may not exhibit symptoms of a particular disease or be predisposed to developing symptoms of a particular disease. Further, if those subjects are symptomatic, they may or may not respond to a certain drug, e.g., a specific SR-BI therapeutic, but may respond to another. Thus, generation of an SR-BI genetic profile, (e.g., categorization of alterations in SR-BI genes which are associated with the development of a particular disease), from a population of subjects, who are symptomatic for a disease or condition that is caused by or contributed to by a defective and/or deficient SR-BI gene and/or protein (an SR-BI genetic population profile) and comparison of an individual's SR-BI profile to the population profile, permits the selection or design of drugs that are expected to be safe and efficacious for a particular patient or patient population (i.e., a group of patients having the same genetic alteration).

For example, an SR-BI population profile can be performed by determining the SR-BI profile, e.g., the identity of SR-BI alleles, in a patient population having a disease, which is associated with one or more specific alleles of SR-BI polymorphic regions. Optionally, the SR-BI population profile can further include information relating to the response of the population to an SR-BI therapeutic, using any of a variety of methods, including, monitoring: 1) the severity of symptoms associated with the SR-BI related disease, 2) SR-BI gene expression level, 3) SR-BI mRNA level, and/or 4) SR-BI protein level. and (iii) dividing or categorizing the population based on particular SR-BI alleles. The SR-BI genetic population profile can also, optionally, indicate those particular SR-BI alleles which are present in patients that are either responsive or non-responsive to a particular therapeutic. This information or population profile, is then useful for predicting which individuals should respond to particular drugs, based on their individual SR-BI profile.

In a preferred embodiment, the SR-BI profile is a transcriptional or expression level profile and step (i) is comprised of determining the expression level of SR-BI proteins, alone or in conjunction with the expression level of other genes known to contribute to the same disease at various stages of the disease.

Pharmacogenomic studies can also be performed using transgenic animals. For example, one can produce transgenic mice, e.g., as described herein, which contain a specific allelic variant of an SR-BI gene. These mice can be created, e.g, by replacing their wild-type SR-BI gene with an allele of the human SR-BI gene. The response of these mice to specific SR-BI therapeutics can then be determined.

Monitoring Effects of SR-BI Therapeutics During Clinical Trials

The ability to target populations expected to show the highest clinical benefit, based on the SR-BI or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of SR-BI as a marker is useful for optimizing effective dose).

In situations in which the disease associated with a specific SR-BI allele is characterized by an abnormal SR-BI expression, the treatment of an individual with an SR-BI therapeutic can be monitored by determining SR-BI characteristics, such as SR-BI protein level or activity, SR-BI MRNA level, and/or SR-BI transcriptional level. This measurement will indicate whether the treatment is effective or whether it should be adjusted or optimized. Thus, SR-BI can be used as a marker for the efficacy of a drug during clinical trials.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a preadministration sample from a subject prior to administration of the agent; (ii) detecting the level of expression of an SR-BI protein, mRNA, or genomic DNA in the preadministration sample; (iii) obtaining one or more post-administration samples from the subject; (iv) detecting the level of expression or activity of the SR-BI protein, MRNA, or genomic DNA in the post-administration samples; (v) comparing the level of expression or activity of the SR-BI protein, mRNA, or genomic DNA in the preadministration sample with the SR-BI protein, mRNA, or genomic DNA in the post administration sample or samples; and (vi) altering the administration of the agent to the subject accordingly. For example, increased administration of the agent may be desirable to increase the expression or activity of SR-BI to higher levels than detected, i.e., to increase the effectiveness of the agent. Alternatively, decreased administration of the agent may be desirable to decrease expression or activity of SR-BI to lower levels than detected, i.e., to decrease the effectiveness of the agent.

Cells of a subject may also be obtained before and after administration of an SR-BI therapeutic to detect the level of expression of genes other than SR-BI, to verify that the SR-BI therapeutic does not increase or decrease the expression of genes which could be deleterious. This can be done, e.g., by using the method of transcriptional profiling. Thus, mRNA from cells exposed in vivo to an SR-BI therapeutic and mRNA from the same type of cells that were not exposed to the SR-BI therapeutic could be reverse transcribed and hybridized to a chip containing DNA from numerous genes, to thereby compare the expression of genes in cells treated and not treated with an SR-BI therapeutic. If, for example an SR-BI therapeutic turns on the expression of a proto-oncogene in an individual, use of this particular SR-BI therapeutic may be undesirable.

Methods of Treatment

The present invention provides for both prophylactic and therapeutic methods of treating a subject having or likely to develop a disorder associated with specific SR-BI alleles and/or aberrant SR-BI expression or activity, e.g., disorders or diseases associated with an abnormal BMI or lipid levels.

Prophylactic Methods

In one aspect, the invention provides a method for preventing in a subject, a disease or condition associated with a specific SR-BI allele and/or an aberrant SR-BI expression or activity, such as a body mass disorder or abnormal lipid level and medical conditions resulting therefrom, by administering to the subject an agent which counteracts the unfavorable biological effect of the specific SR-BI allele. Subjects at risk for such a disease can be identified by a diagnostic or prognostic assay, e.g., as described herein. Administration of a prophylactic agent can occur prior to the manifestation of symptoms associated with specific SR-BI alleles, such that a disease or disorder is prevented or, alternatively, delayed in its progression. Depending on the identity of the SR-BI allele in a subject, a compound that counteracts the effect of this allele is administered. The compound can be a compound modulating the plasma level of lipids. The treatment can also be a specific diet. In particular, the treatment can be undertaken prophylactically, before any other symptoms are present. Such a prophylactic treatment could thus prevent the development of an abnormal BMI or lipid level, e.g., abnormally high LDL level or abnormally low HDL. The prophylactic methods are similar to therapeutic methods of the present invention and are further discussed in the following subsections.

Therapeutic Methods

The invention further provides methods of treating subjects having a disease or disorder associated with a specific allelic variant of a polymorphic region of an SR-BI gene. Preferred diseases or disorders include those associated with an abnormal body mass, or abnormal lipoprotein (LDL and HDL) levels and disorders resulting therefrom (e.g. cardiovascular disease, obesity, cachexia and gallstone formation). In one embodiment, the method comprises (a) determining the identity of the allelic variant; and (b) administering to the subject a compound that compensates for the effect of the specific allelic variant. The polymorphic region can be localized at any location of the gene, e.g., in the promoter (e.g., in a regulatory element of the promoter), in an exon, (e.g., coding region of an exon), in an intron, or at an exon/intron border. Thus, depending on the site of the polymorphism in the SR-BI gene, a subject having a specific variant of the polymorphic region which is associated with a specific disease or condition, can be treated with compounds which specifically compensate for the allelic variant.

In a preferred embodiment, the identity of one or more of the following nucleotides of an SR-BI gene of a subject is determined: nucleotide 146 of exon 1, nucleotide 119 of exon 3, nucleotide 41 of exon 8, nucleotide 54 of intron 5, and nucleotide −41 of intron 10. If a female subject has the more common allele of residue 41 of exon 8, high LDL levels and resulting cardiovascular disorders can be prevented from occurring or can be reduced, by administering to the subject a pharmaceutically effective amount of a compound to reduce LDL level to a normal LDL level. Similarly, if a female subject has the less common allele of residue 54 of intron 5, a high BMI and/or high LDL level and consequences thereof, such as diabetes and cardiovascular disorders, can be prevented from occurring or reduced, by administering to the subject a pharmaceutically effective amount of a compound to reduce the BMI. In another embodiment of the invention, if a male subject has the more common allele at residue 41 of exon 8, the more common allele at residue 54 of intron 5, and the more common allele at residue 146 of exon 1, development of low HDL levels can be prevented or increased by administering to the subject a pharmaceutically effective amount of a compound that increases HDL levels.

Generally, the allelic variant can be a mutant allele, i.e., an allele which when present in one, or preferably two copies, in a subject results in a change in the phenotype of the subject. A mutation can be a substitution, deletion, and/or addition of at least one nucleotide relative to the wild-type allele. Depending on where the mutation is located in the SR-BI gene, the subject can be treated to specifically compensate for the mutation. For example, if the mutation is present in the coding region of the gene and results in an inactive or less active SR-BI protein, the subject can be treated, e.g., by administration to the subject of a nucleic acid encoding a wild-type SR-BI protein, such that the expression of the wild-type SR-BI protein compensates for the endogenous mutated form of the SR-BI protein. Nucleic acids encoding wild-type human SR-BI protein are set forth in SEQ ID Nos. 1 and 3 and are described, e.g., in Calvo and Vega (1993) J. Biol. Chem. 268:18929.

Furthermore, depending on the site of the mutation in the SR-BI protein and the specific effect on its activity, specific treatments can be designed to compensate for that effect. The SR-BI protein is a cell surface receptor which binds specific forms of lipids, e.g., modified lipid or lipoproteins, e.g., HDL. Thus, an SR-BI protein has an extracellular domain which binds specific molecules, e.g., lipids, a transmembrane domain, and an intracellular domain, which is likely to transmit an intracellular signal. The structure of SR-BI proteins is further described, e.g., in Calvo and Vega, supra; Acton et al. (1994) J. Biol. Chem. 269:21003; Acton et al. (1 995) Science 271:518; Rigotti et al. (1 995) J. Biol. Chem. 270:16221; Fukasawa et al. (1996) Exp. Cell. Res. 222:246; Wang et al. (1996) J. Biol. Chem. 271:21001; and published PCT Application having publication number WO 96/00288 by Acton et al. Thus, if the mutation results in an SR-BI protein which is less capable of binding certain types of modified lipids, resulting in an accumulation of such lipids in the subject, a treatment can be designed which removes such modified lipids from the subject. In one embodiment, a compound which binds this form of lipid and is capable of targeting the lipid to a site where it is eliminated, is administered to the subject. Alternatively, the expression of another cell surface receptor which binds this type of lipid can be increased. In fact, both SR-BI and the class B scavenger receptor CD36 are capable of interacting with anionic phospholipids (Rigotti et al., supra). Thus, if a subject has a mutant SR-BI protein which is defective in its binding to anionic phospholipids, the subject can be treated by administration of a compound which increases CD36 protein levels in the cells.

In situations in which the mutant SR-BI protein binds certain forms of lipids with higher affinity, and if this is causing or contributing to a disease, a subject having such a mutated SR-BI protein can be treated, e.g., by administration of compounds which inhibit or decrease the interaction between the specific form of the lipid and SR-BI. For example, soluble forms of SR-BI proteins or binding fragments thereof, can be administered to the subject. Alternatively, small molecules can be administered to the subject for interfering in the interaction between SR-BI and a lipid.

A mutant SR-BI protein can also be an SR-BI protein having a mutation in the cytoplasmic domain of the protein which results in an aberrant signal transduction from the receptor. Subjects having such a mutation can be treated, e.g., by administration of compounds which induce the same or similar signal transduction or compounds which act downstream of the receptor.

The effect of a mutation in an SR-BI protein can be determined according to methods known in the art. For example, if the mutation is located in the extracellular portion of the protein, one can perform binding assays with specific forms of lipids, e.g., HDL, and determine whether the binding affinity of such lipid with the mutated SR-BI protein is different from the binding affinity of the lipid with the wild-type protein. Such assays can be performed using a soluble form of an SR-BI protein or a membrane bound form of the protein. If the mutation in the SR-BI protein is located in the cytoplasmic domain of the protein, signal transduction experiments can be performed to determine whether the signal transduced from the mutated receptor differs from the signal transduced from the wild-type receptor. Alternatively, one can also investigate whether binding to a protein which interacts with the cytoplasmic domain of the receptor is affected by the mutation. Such determination can be made by, e.g., by immunoprecipitation.

Yet in another embodiment, the invention provides methods for treating a subject having a mutated SR-BI gene, in which the mutation is located in a regulatory region of the gene. Such a regulatory region can be localized in the promoter of the gene, in the 5' or 3' untranslated region of an exon, or in an intron. A mutation in a regulatory region can result in increased production of SR-BI protein, decreased production of SR-BI protein, or production of SR-BI having an aberrant tissue distribution. The effect of a mutation in a regulatory region upon the SR-BI protein can be determined, e.g., by measuring the SR-BI protein level or mRNA level in cells having an SR-BI gene having this mutation and which, normally (i.e., in the absence of the mutation) produce SR-BI protein. The effect of a mutation can also be determined in vitro. For example, if the mutation is in the promoter, a reporter construct can be constructed which comprises the mutated promoter linked to a reporter gene, the construct transfected into cells, and comparison of the level of expression of the reporter gene under the control of the mutated promoter and under the control of a wild-type promoter. Such experiments can also be carried out in mice transgenic for the mutated promoter. If the mutation is located in an intron, the effect of the mutation can be determined, e.g., by producing transgenic animals in which the mutated SR-BI gene has been introduced and in which the wild-type gene may have been knocked out. Comparison of the level of expression of SR-BI in the mice transgenic for the mutant human SR-BI gene with mice transgenic for a wild-type human SR-BI gene will reveal whether the mutation results in increased, decreased synthesis of the SR-BI protein and/or aberrant tissue distribution of SR-BI protein. Such analysis could also be performed in cultured cells, in which the human mutant SR-BI gene is introduced and, e.g., replaces the endogenous wild-type SR-BI gene in the cell. Thus, depending on the effect of the mutation in a regulatory region of an SR-BI gene, a specific treatment can be administered to a subject having such a mutation. Accordingly, if the mutation results in decreased production of an SR-BI protein, the subject can be treated by administration of a compound which increases synthesis, such as by increasing SR-BI gene expression, and wherein the compound acts at a regulatory element different from the one which is mutated. Alternatively, if the mutation results in increased SR-BI protein levels, the subject can be treated by administration of a compound which reduces SR-BI protein production, e.g., by reducing SR-BI gene expression or a compound which inhibits or reduces the activity of SR-BI.

Furthermore, it is likely that subjects having different allelic variants of an SR-BI polymorphic region will respond differently to therapeutic drugs to treat diseases or conditions, such as those associated with an abnormal lipid level. Cholesterol-lowering drugs include lovastatin (MEVACOR; Merck & Co.), simvastatin (ZOCOR; Merck & Co.), dextrothyroxine (CHOLOXIN; Knoll Pharmaceutical Co.), pamaqueside (Pfizer), cholestryramine (QUESTRAN; Bristol-Myers Squibb), colestipol (COLESTID; Pharmacia & Upjohn), acipomox (Pharmacia & Upjohn), fenofibrate (LIPIDIL), gemfibrozil (LOPID; Warner-Lambert), cerivastatin (LIPOBAY; Bayer), fluvastatin (LESCOL; Novartis), atorvastatin (LIPITOR, Warner-Lambert), etofylline clofibrate (DUOLIP; Merckle (Germany)), probucol (LORELCO; Hoechst Marion Roussel), omacor (Pronova (Norway), etofibrate (Merz (Germany), clofibrate (ATROMID-S; Wyeth-Ayerst (AMP)), and niacin (numerous manufacturers). Drugs for treating obesity and/or gallstones include dexfenflurafnine (REDUX, Interneuron Pharmaceuticals), megestrol acetate (MEGACE, Bristol-Myers Squibb), Phenylpropanolamine (ACUTRIM; Ciba; and DEXUTRIM; Thompson), fluoxetine (PROZAC, Lilly), dextroamphetamine (DEXEDRINE, SmithKline Beecham), fenfluramine and phentenine, chenodiol (CHENIX, Solvay), orlistat (XENICAL, Roche), anandamide (Yissum (Israel)), PCM-4 (Omega Pharmaceutical), mono-octanoin (MOCTAN, Stokely-van Camp), sibutramine (M:ERIDIA, Knoll), testosterone (TESTODERM, Alza), oxandrolone (OXANDRIN, Bio-Technology General), ceruletide diethylamine (TYMTRAN, Pharmacia & Upjohn), testosterone and dihydrotestosterone (ANDROGEL and ANDROGEL-DHT, unimed), somatropin (SEROSTIM, Ares-Serono and BIO-TROPIN, Biotechnology General), and thalidomide (SYNOVIR, Celgene).

A correlation between drug responses and specific alleles of SR-BI can be shown, for example, by clinical studies wherein the response to specific drugs of subjects having different allelic variants of a polymorphic region of an SR-BI gene is compared. Such studies can also be performed using animal models, such as mice having various alleles of human SR-BI genes and in which, e.g., the endogenous SR-BI has been inactivated such as by a knock-out mutation. Test drugs are then administered to the mice having different human SR-BI alleles and the response of the different mice to a specific compound is compared. Accordingly, the invention provides assays for identifying the drug which will be best suited for treating a specific disease or condition in a subject. For example, it will be possible to select drugs which will be devoid of toxicity, or have the lowest level of toxicity possible for treating a subject having a disease or condition.

Other uses for the nucleic acids of the invention

The identification of different alleles of SR-BI can also be useful for identifying an individual among other individuals from the same species. For example, DNA sequences can be used as a fingerprint for detection of different individuals within the same species (Thompson, J. S. and Thompson, eds., Genetics in Medicine, WB Saunders Co., Philadelphia, Pa. (1991)). This is useful, e.g., in forensic studies.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

5. EXAMPLES

The invention now being generally described, it will be more readily understood by reference to the following examples which are included merely for purposes of illustration of certain aspects and embodiments of the present invention, and are not intended to limit the invention.

Example 1

Isolation and sequence analysis of genomic DNA encoding the human SR-BI protein

A probe consisting of a 474 base pair fragment of the human SR-BI cDNA was used to isolate bacterial artificial chromosomes (BACs) containing genomic DNA encoding the human SR-BI protein from a human BAC library (Research Genetics Inc. (Huntsville, Ala.) Cat.#96041)). Two BACs were isolated by hybridizing the probe to this library. These BACs were then sized by pulse-field electrophoresis and the inserts were found to be approximately 80 and 70 kilobases long for BAC 179m10 and BAC 256i19, respectively. All further discussion will focus on BAC 179 m10.

BAC 179m10 was digested with restriction enzymes and analyzed by Southern blot hybridization with portions of human SR-BI cDNA, and shown to contain a large portion of the SR-BI sequence. This BAC was then sheared by nebulizing the DNA into fragments of approximately 1–3 kb which were inserted into the pminisk vector and the resulting insert sizes ranged from 1–3 kb. Initially, clones which hybridized to the coding sequence of the full-length human SR-BI cDNA were sequenced, leading to the identification of most of the exons of the gene. Further random sequencing of the BAC sheared library led to the identification of the remaining coding exons and the adjacent intron flanking sequences.

Figure 3A-2:
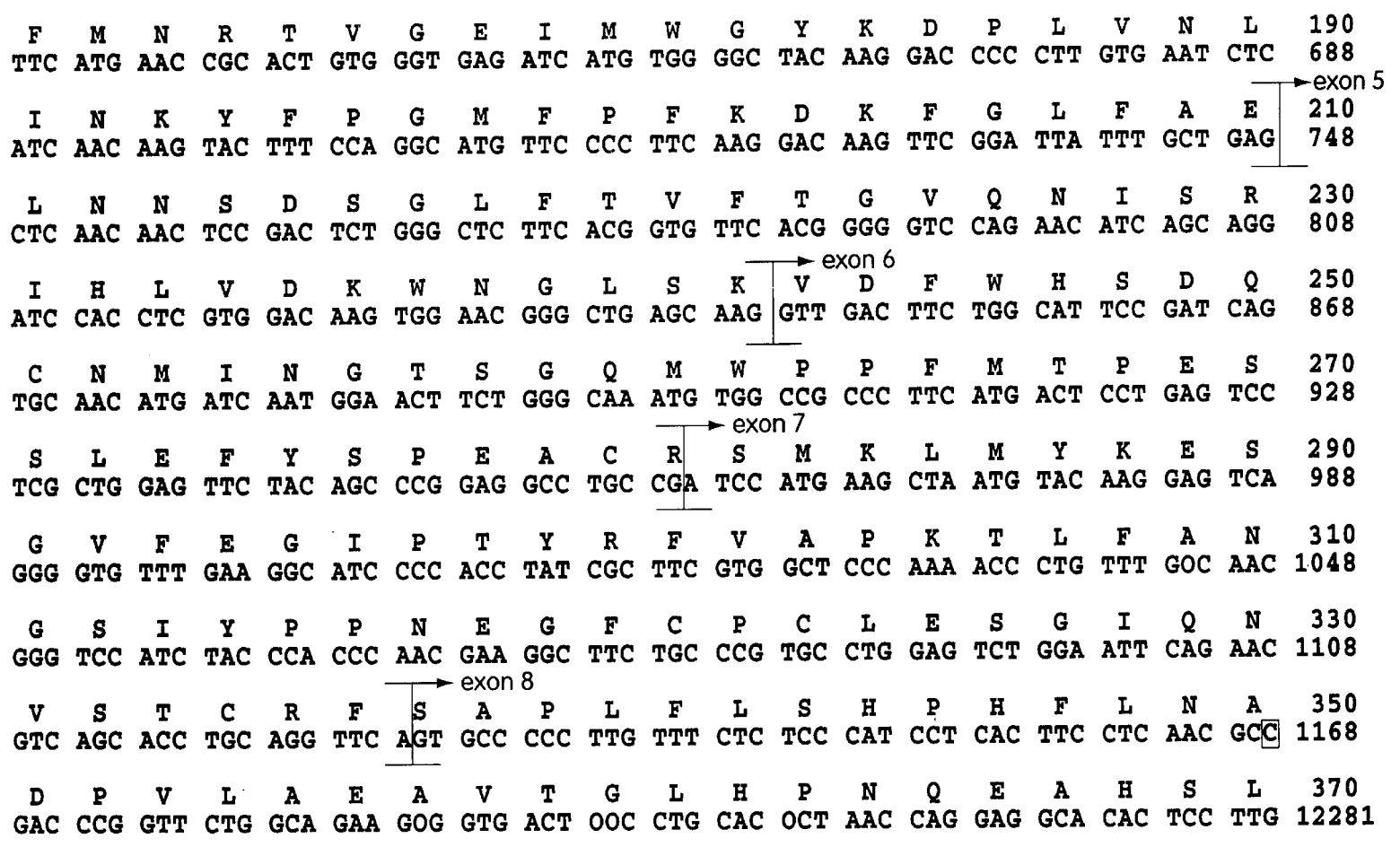
Figure 3B-1:
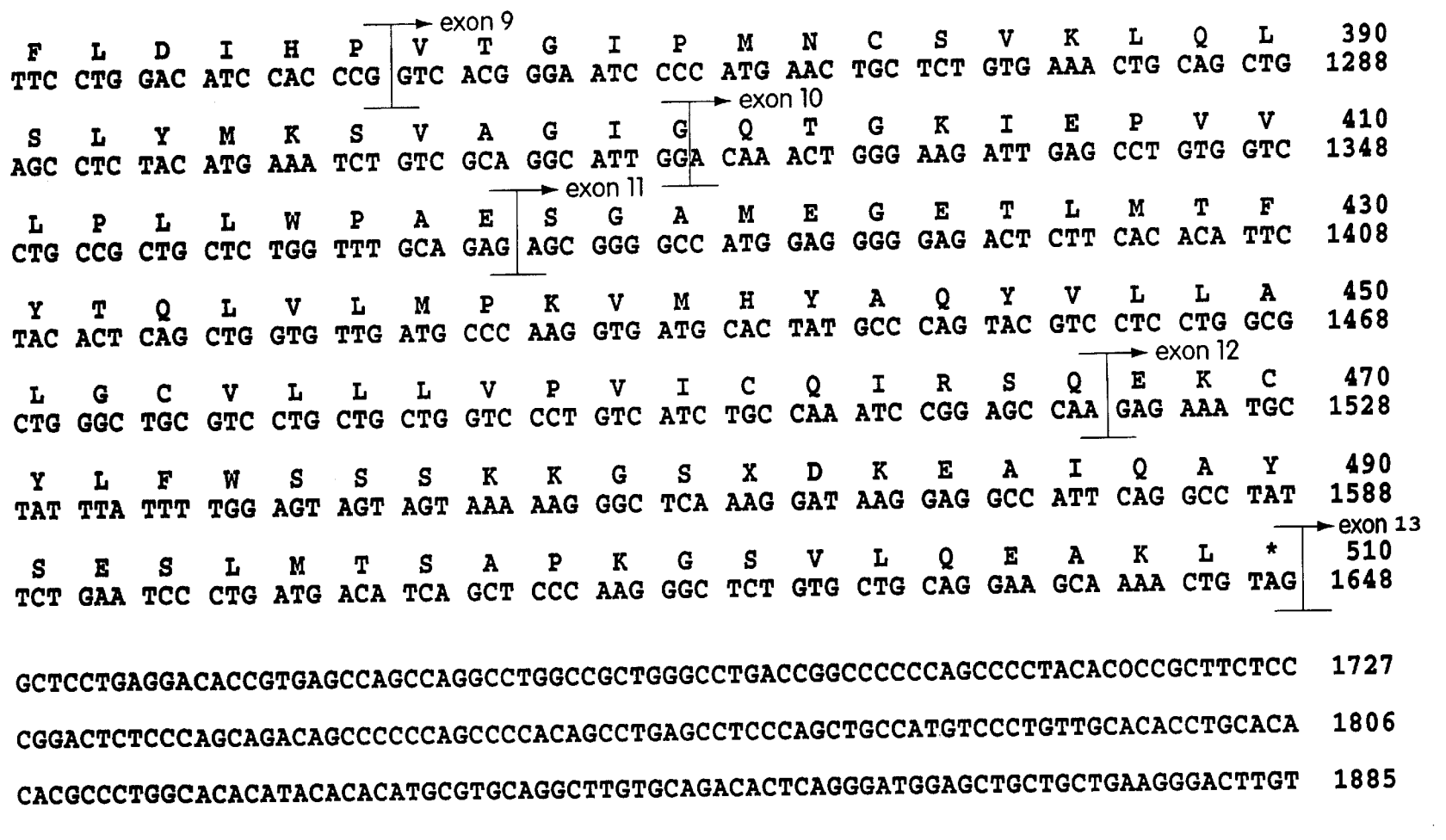

Sequence analysis of the genomic DNA indicated that the human SR-BI gene is at least 50 kb and contains 12 coding exons and one non-coding exon (exon 13, which contains the entire 3' untranslated region). The genomic structure of human SR-BI is shown in FIG. 1. The nucleotide sequence of the exons and portions of the introns which are adjacent to the exons is shown in FIG. 2. The coding region of the human SR-BI gene consists of 12 exons (see Table I in the Detailed Description). The location of introns relative to the nucleotide sequence of a cDNA encoding human SR-BI is shown in FIG. 2 and FIG. 3 and indicated in Table II of the Detailed Description. The portions of the protein encoded by each of the exons is also shown in FIG. 3 and in Table II.

A number of the introns are extremely large (>10 kb) (see Table I in the Detailed Description). The intron/exon boundaries were remarkably similar to those found in the human CD36 gene, which is a member of the same protein family as SR-BI (Tang et al. (1994) J. Biol. Chem. 269:6011).

Example 2

Identification of primer pairs to isolate intronic, exonic, and promoter sequences for detection of polymorphisms and mutations Multiple pairs of primers were synthesized in order to amplify each of the exons or portions thereof and adjacent intronic regions. Genomic DNA from a human subject was subjected to PCR in 25 µl reactions (1× PCR Amplitaq polymerase buffer, 0.1 mM dNTPs, 0.8 µM 5' primer, 0.8 µM 3' primer, 0.75 units of Amplitaq polymerase, 50 ng genomic DNA) using each of the above described pairs of primers under the following cycle conditions: 94° C. for 2 min, 35× [94° C. for 40 sec, annealing temp for 30 sec, 72° C. for 1 min], 72° C. for 5 min, 4° C. hold. The resulting PCR products were analyzed on a 2% agarose gel. The identity of the PCR product was confirmed by digestion with a restriction enzyme and subsequent agarose electrophoresis. Twelve pairs of oligomers were chosen to serve as PCR primers to amplify regions containing each of the 12 coding exons of the human SR-BI gene and one pair of primers was chosen to serve as PCR primers to amplify a promoter region. The nucleotide sequence of these primers in indicated in Table VI and nucleotide sequences to which these primers bind are shown in FIG. 2. The optimum PCR annealing temperature for each primer pair as well as the expected sizes of the PCR products and diagnostic restriction sites is set forth below in Table V. Table V also indicates the size of DNA fragments obtained when digesting the amplified fragment with the restriction enzyme indicated in the table. A PCR reaction using primers having SEQ ID NO: 41 and 42 for amplifying exon 1 is preferably carried out in the presence of 10% DMSO.

TABLE IV

| exon | primer name | SEQ ID NO: | Nucleotide Sequence (5' -> 3') |
|---|---|---|---|
| 1 | 5e16srb1 | 41 | CCCCTGCCGCCGGAATCCTGAAG |
|   | 3e16srb1 | 42 | CGCTTTGGCGGAGCAGCCCATGTC |
| 2 | 5e22srb1 | 43 | TGGGGCCCTCATCACTCTCCTCAC |
|   | 3e22srb1 | 44 | GCAGCCTCCCCATCCCGTCCACT |
| 3 | 5e30srb1 | 45 | ATTGCAGGCGAGTAGAAG |
|   | 3e30srb1 | 46 | CAGGCGGGAGGAGAGACA |
| 4 | 5e41srb1 | 47 | TGGGCTCTTTGCTGTGAGGC |
|   | 3e41srb1 | 48 | CCAGGCTGTGTGAGGGGAAG |
| 5 | 5e50srb1 | 49 | GCCCAGAATGTTCAGACCAG |
|   | 3e50srb1 | 50 | GCACCCTCTTCACGACAAAG |
| 6 | 5e60srb1 | 51 | CACCTGAGAGGGCTTATTA |
|   | 3e60srb1 | 52 | CAAAATGCTTTCCAAGTGC |
| 7 | 5e71srb1 | 53 | GCCGCCGGGTCTGGGTGTCC |
|   | 3e71srb1 | 54 | CAGAGGCCAGAGATTAAGCAGAC |
| 8 | 5e81srb1 | 55 | TTGTATGATGTCCCCTCCCT |
|   | 3e81srb1 | 56 | TTCCCACCACCCCAGCCCAC |

TABLE IV-continued

| exon | primer name | SEQ ID NO: | Nucleotide Sequence (5' -> 3') |
|---|---|---|---|
| 9 | 5e91srb1 | 57 | GGTTGACTGTGTCCCTGGAG |
|   | 3e91srb1 | 58 | GGGAACACTGGAGCACTGAGC |
| 10 | 5e104srb1 | 59 | GGTGGTGAGGGTTTAGTGTG |
|   | 3e104srb1 | 60 | CTCCCCCCGCCTCCTGCCTC |
| 11 | 5e112srb1 | 61 | AAGGTGTTGGGTGGCATCTG |
|   | 3e112srb1 | 62 | GGCTCCAGGCTGCGGTTGGC |
| 12 | 5e100srb1 | 63 | TTGAAGAACCGTGTAAAAC |
|   | 3e100srb1 | 64 | TTGAGGCTGAAGGAATGA |
| Prom. | 5p13srb1 | 83 | TCCTGGGTGGGCTGGCGAAGTC |
|   | 5p13srb1 | 84 | GTTTTGGGGCGGGAGCTGATGAAG |

TABLE V

| Exon | primer pairs | Temp. | Product length | Enzyme check |
|---|---|---|---|---|
| 1 | SEQ ID NO: 41<br>SEQ ID NO: 42 | 65° C. | 162 bp | BamHI (144, 118) |
| 2 | SEQ ID NO: 43<br>SEQ ID NO: 44 | 64° C. | 294 bp | ApaI (189, 98, 7) |
| 3 | SEQ ID NO: 45<br>SEQ ID NO: 46 | 57° C. | 281 bp | XhoI (153, 128) |
| 4 | SEQ ID NO: 47<br>SEQ ID NO: 48 | 59° C. | 360 bp | SpeI (292, 68) |
| 5 | SEQ ID NO: 49<br>SEQ ID NO: 50 | 57° C. | 291 bp | BamHI (157, 134) |
| 6 | SEQ ID NO: 51<br>SEQ ID NO: 52 | 52° C. | 273 bp | DraII (179, 72, 22) |
| 7 | SEQ ID NO: 53<br>SEQ ID NO: 54 | 59° C. | 290 bp | EcoRI (184, 106) |
| 8 | SEQ ID NO: 55<br>SEQ ID NO: 56 | 58° C. | 261 bp | HaeIII (158, 103) |
| 9 | SEQ ID NO: 57<br>SEQ ID NO: 58 | 57° C. | 206 bp | PstI (107, 99) |
| 10 | SEQ ID NO: 59<br>SEQ ID NO: 60 | 56° C. | 253 bp | AvaII (148, 105) |
| 11 | SEQ ID NO: 61<br>SEQ ID NO: 62 | 60° C. | 327 bp | NcoI (242, 85) |
| 12 | SEQ ID NO: 63<br>SEQ ID NO: 64 | 51° C. | 303 bp | PstI (184, 119) |
| prom. | SEQ ID NO: 83<br>SEQ ID NO: 84 | 63° C. | 247 bp | BstXI (200, 47) |

Example 3

Detection of polymorhic regions in the human SR-BI gene by SSCP

Genomic DNA from a population of 389 unrelated Caucasian men and women, chosen because they had a known HDL and LDL level (high, normal, or low), known body mass index, known level of triglycerides, and known age (see Table VI) was analyzed as described below.

TABLE VI

Anthropometric and plasma lipid concentrations of the population studied

|  | Men (n = 101) | Women (n = 288) |
|---|---|---|
| Age (years) | 40 ± 16 | 36 ± 12 |
| BMI (kg/m$^2$) | 25.2 ± 3.3 | 22.8 ± 3.6 |
| TC (mg/dL) | 227 ± 57 | 198 ± 45 |
| LDL-C (mg/dL) | 158 ± 49 | 122 ± 39 |
| HDL-C (mg/dL) | 45 ± 23 | 63 ± 17 |
| TG (mg/dL) | 120 ± 64 | 68 ± 34 |

Genomic DNA from each of these individuals was subjected to PCR in 25 µl reactions (1× PCR Amplitaq polymerase buffer, 0.1 mM dNTPs, 0.8 µM 5' primer, 0.8 µM 3' primer, 0.75 units of Amplitaq polymerase, 50 ng genomic DNA) using each of the above described pairs of primers under the following cycle conditions: 94° C. for 2 min, 35× [94° C. for 40 sec, annealing temp for 30 sec, 72° C. for 1 min], 72° C. 5 min, 4° C. hold. The optimum PCR annealing temperatures for each set of primers are given in Table V. The expected sizes of the PCR products, as well as diagnostic restriction sites, are also indicated in Table V.

The amplified genomic DNA fragments were then analyzed by SSCP (Orita et al. (1989) *PNAS USA* 86:2766, see also Cotton (1993)*Mutat Res* 285:125–144; and Hayashi (1992) *Genet Anal Tech Appl* 9:73–79). From each 25 µl PCR reaction, 3 µl was taken and added to 7 µl of loading buffer. The mixture was heated to 94° C. for 5 min and then immediately cooled in a slurry of ice-water. 3–4 µl were then loaded on a 10% polyacrylamide gel containing 10% glycerol and then subjected to electrophoresis either overnight at 4 Watts at room temperature, overnight at 4 Watts at 4° C. (for amplifying a promoter region), or for 5 hours at 20 Watts at 4° C. (for amplifying exons 3 and 4). The secondary structure of single-stranded nucleic acids varies according to sequence, thus allowing the detection of small differences in nucleic acid sequence between similar nucleic acids. At the end of the electrophoretic period, the DNA was analyzed by gently overlaying a mixture of dyes onto the gel (1× the manufacturer's recommended concentration of SYBR Green I and SYBR Green II in 0.5× TBE buffer (Molecular Probes)) for 5 min, followed by rinsing in distilled water and detection in a Fluoroimager 575 (Molecular Dynamics). Polymorphisms were found in or near exons 1, 3, 5, 8, and 10.

Example 4
Identification of polymorphic regions in the human SR-BI gene by direct sequencing of PCR products To determine the sequences of the polymorphisms identified, the regions containing the polymorphisms were reamplified using the aforementioned primers which were modified to contain additional sequence which could be used to directly sequence the PCR product (M13 forward sequence for 5' primer and +M13 reverse sequence for 3' primer) on the 5' end of the primers as listed in Table IV. In particular, the forward primers (5' end primers) contained the nucleotide sequence "TGTAAAACGACGGCCAGT" (SEQ ID NO: 85) located 5' of the nucleotide sequences shown in Table IV and the reverse primer (3' end primer) contained the nucleotide sequence "CAGGAAACAGCTAT-GACC" (SEQ ID NO: 86) located 5' of the nucleotide sequence shown in Table III. The genomic DNA from the subjects was subjected to PCR in 50 µl reactions (1× PCR Amplitaq polymerase buffer, 0.1 mM dNTPs, 0.8 µM 5' primer, 0.8 µM 3' primer, 0.75 units of Amplitaq polymerase, 50 ng genomic DNA) using each of the above described pairs of primers under the following cycle conditions: 94° C. for 2 min, 35× [94° C. for 40 sec, annealing temp for 30 sec, 72° C. for 1 min], 72° C. 5 min, 4° C. hold. The optimum PCR annealing temperatures for each of the primer pairs are given in Table V. The newly amplified products were then purified by agarose gel electrophoresis and subjected to sequencing using M13 forward and reverse primers.

The results indicate that the polymorphism in the region of exon 1 is a change from a guanine at nucleotide 146 to an adenine, resulting in a change of the second amino acid of the protein from a glycine to a serine. The polymorphism in the region of exon 3 is a change from the guanine at position to 119 to an adenine, resulting in a change of amino acid 135 of the protein from a valine to isoleucine. The polymorphism in the region of exon 8 was determined to constitute a change in base position 41 of exon 8, from a cytidine to a thymidine. This substitution does not result in a change in amino acid. In a subpopulation of 142 individuals, about 35% of these individuals were homozygous for an allele having a cytidine at position 41 of exon 8; about 17% of these individuals were homozygous for an allele having a thymidine at this position; and about 48% of these individuals were heterozygous, having one allele of each type. The polymorphism in the region of exon 5 is a change in nucleotide 54 of intron 5 (nucleotide 1 being the first nucleotide of the intron), from a cytidine to a thymidine. In a subpopulation of 142 individuals, about 24% of individuals have a thymidine at position 54 of intron 5. The polymorphism in the region of exon 11 is a change from the cytidine at position −41 (nucleotide −1 corrresponds to the most 3' nucleotide of intron 10) of intron 10 to a guanine. The polymorphisms are indicated in Table III and in FIG. 2.

Example 5
Association of common polymorphisms at the SR-BI gene with plasma lipids and anthropometric parameters After identification of the mutations in exons 1, 3, and 8 and introns 5 and 10, subjects were typed by digestion of PCR products using the primers and enzymes listed in Table VI.

TABLE VII

Primers and enzymes for typing allelic variants

| polymorphism | primers | temp | digest | product sizes |
|---|---|---|---|---|
| exon 1 | CCGGCGATGGGGCATAAAACCACT SEQ ID NO:89 | 68–62 C. | AluI | GG: 263 |
| (G/A) | CGCCCAGCACAGCGCACAGTAGC SEQ ID NO:90 |  |  | GA: 263, 192, 71 |
|  |  |  |  | AA: 192, 71 |

TABLE VII-continued

Primers and enzymes for typing allelic variants

| poly-morphism | primers | temp | digest | product sizes |
|---|---|---|---|---|
| intron 5 (C/T) | GCCCAGAATGTTCAGACCAG SEQ ID NO:91<br>GCACCCTCTTCACGACAAAG SEQ ID NO:92 | 57 C. | ApaI | CC: 194, 67, 30<br>CT: 194, 97, 67, 30<br>TT: 194, 97 |
| exon 8 (C/T) | CCTTGTTTCTCTCCCATCCTCACTTCCTCAAGGCA SEQ ID NO:93<br>CACCACCCCAGCCCACAGCAGC SEQ ID NO:94 | 66–61 C. | HaeIII | CC: 154, 33, 31<br>CT: 154, 64, 33, 31<br>TT: 154, 64 |

Plasma lipids were measured after a 12 to 14-hour overnight fast, using blood collected in tubes containing 0.1% EDTA. Plasma HDL-cholesterol was measured after precipitation of plasma apoB-containing lipoproteins as previously described. Plasma total cholesterol, HDL cholesterol and triglyceride levels were measured as previously described. LDL cholesterol was calculated by the Friedewald equation when triglyceride levels were below 400 mg/dL. Coefficients of variation between runs for all lipid assays were less than 5%.

The SPSS statistical package PC version 7.5.1 was used for the statistical analysis. Because of the differences observed between men and women for several of the anthropometric and lipid variables, all the statistical analyses were carried out separately by gender. Triglycerides were log transformed for analysis. For each of the variables examined, the significance of the differences between alleles or genotypes was estimated by analysis of covariance (ANCOVA) using the General Linear Model (GLM) procedure from SPSS, with age as covariate and the Tukey's post hoc test for multiple comparisons for observed means. For analysis related to HDL-C, smoking and alcohol intake were also included as covariates. Means and standard deviations for all variables were calculated for each genotype group and the significance level was established at p<0.05. The allele and haplotype frequencies were estimated using the EH linkage utility program (Terwilliger and Ott J. (1994) *Handbook for human genetic linkage*. Johns Hopkins University Press, Baltimore, Md.).

The frequencies of the less common allele for each of the polymorphisms described at the SR-BI gene locus were as follows: exon 1: 0.1136; exon 3: 0.0184; intron 5: 0.1002; exon 8: 0.4389 and intron 11: 0.0425. The associations between these common polymorphisms and plasma lipid concentrations and BMI are presented in table VIII for men and table IX for women. For men, no significant associations were observed between any of the variables examined and the common polymorphisms at exon 1, intron 5 and exon 8. Conversely, in women, the less common allele defined by the polymorphism at exon 8 was associated with significantly lower mean plasma LDL cholesterol concentrations (118±38 and 116±36 mg/dL for heterozygotes and homozygotes, respectively) than those observed in subjects homozygous for the most common allele (131±42 mg/dL; p=0.043). No other significant associations were observed between these polymorphisms and other lipid variables. In women, a significant association was observed between the intron 5 polymorphism and BMI. Women carriers of the less common allele showed a mean BMI value (23.8±3.8) that was significantly greater (p=0.03 1) than those women homozygous for the most common allele (22.4±3.4).

TABLE VIII

Anthropometric characteristics and plasma lipid concentration of the population studied according to SR-BI genotypes (Men)

| | Exon 1 | | | Intron 5 | | | Exon 8 | | | |
|---|---|---|---|---|---|---|---|---|---|---|
| | 1/1 (n = 71) | 1/2 (n = 8) | P value | 1/1 (n = 74) | 1/2 (n = 19) | P value | 1/1 (n = 22) | 1/2 (n = 49) | 2/2 (n = 18) | P value |
| Age (years) | 41 ± 14 | 38 ± 16 | 0.659 | 40 ± 15 | 46 ± 13 | 0.114 | 47 ± 14 | 42 ± 14 | 37 ± 13 | 0.068 |
| BMI (kg/m$^2$) | 25.7 ± 3.0 | 25.6 ± 1.9 | 0.883 | 25.3 ± 2.6 | 26.1 ± 3.8 | 0.326 | 25.7 ± 3.6 | 25.8 ± 2.5 | 25.0 ± 3.2 | 0.583 |
| TC (mg/dL) | 228 ± 46 | 221 ± 38 | 0.712 | 225 ± 55 | 240 ± 41 | 0.282 | 234 ± 40 | 221 ± 51 | 225 ± 47 | 0.559 |
| LDL-C (mg/dL) | 159 ± 46 | 157 ± 47 | 0.908 | 156 ± 51 | 175 ± 48 | 0.145 | 168 ± 44 | 154 ± 52 | 158 ± 47 | 0.520 |
| HDL-C (mg/dL) | 43 ± 22 | 43 ± 14 | 0.983 | 43 ± 24 | 45 ± 19 | 0.733 | 39 ± 17 | 43 ± 25 | 44 ± 16 | 0.761 |
| TG (mg/dL) | 127 ± 65 | 105 ± 43 | 0.346 | 129 ± 68 | 98 ± 27 | 0.052 | 133 ± 63 | 122 ± 60 | 119 ± 69 | 0.715 |

TABLE IX

Anthropometric characteristics and plasma lipid concentration of the population studied according to SR-BI genotypes (Women)

| | Exon 1 | | | | Intron 5 | | | Exon 8 | | | |
|---|---|---|---|---|---|---|---|---|---|---|---|
| | 1/1 (n = 181) | 1/2 (n = 66) | 2/2 (n = 1) | P value | 1/1 (n = 74) | 1/2 (n = 19) | P value | 1/1 (n = 73) | 1/2 (n = 148) | 2/2 (n = 37) | P value |
| Age (years) | 35 ± 12 | 38 ± 12 | 40 | 0.218 | 36 ± 12 | 38 ± 12 | 0.333 | 37 ± 12 | 36 ± 12 | 34 ± 12 | 0.458 |
| BMI (k/(m$^2$)) | 22.9 ± 3.9 | 22.5 ± 3.0 | 19.7 | 0.552 | 22.4 ± 3.4 | 23.8 ± 3.8 | 0.031 | 22.8 ± 3.0 | 23.0 ± 3.9 | 21.9 ± 3.4 | 0.252 |
| TC (mg/dL) | 197 ± 45 | 198 ± 42 | 211 | 0.932 | 198 ± 46 | 204 ± 44 | 0.446 | 206 ± 49 | 196 ± 42 | 192 ± 42 | 0.215 |
| LDL-C (mg/dL) | 121 ± 39 | 120 ± 38 | 134 | 0.928 | 122 ± 39 | 125 ± 42 | 0.711 | 131 ± 42 | 118 ± 38 | 116 ± 36 | 0.043 |
| HDL-C (m/dL) | 63 ± 17 | 64 ± 19 | 63 | 0.930 | 62 ± 16 | 64 ± 21 | 0.145 | 61 ± 16 | 64 ± 17 | 64 ± 22 | 0.500 |
| TG (mg/dL) | 64 ± 28 | 71 ± 37 | 72 | 0.317 | 68 ± 35 | 64 ± 30 | 0.423 | 67 ± 35 | 70 ± 38 | 57 ± 22 | 0.146 |

Figure 4:
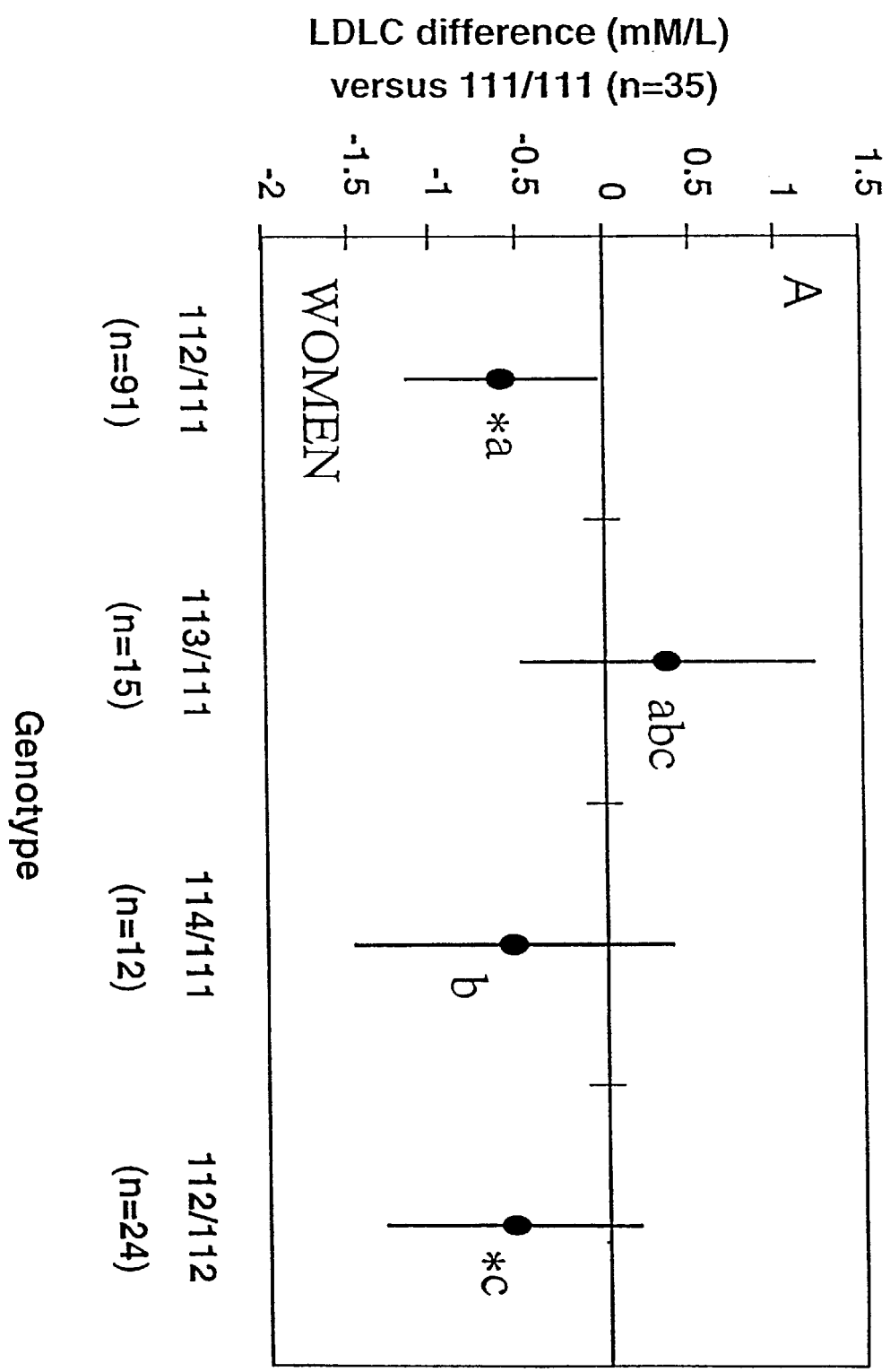
FIG. 4 is a graphic representing the mean LDL-C differences (+/−95% Confidence intervals) between SR-BI genotypes carrying variant alleles and the wild-type genotype (111/111) in women. *significantly different from 111/111 ($p<0.030$). The differences between genotypes sharing letters are statistically significant (a: $p=0.001$; b: $p=0.016$; c: $p=0.004$).
Figure 5:
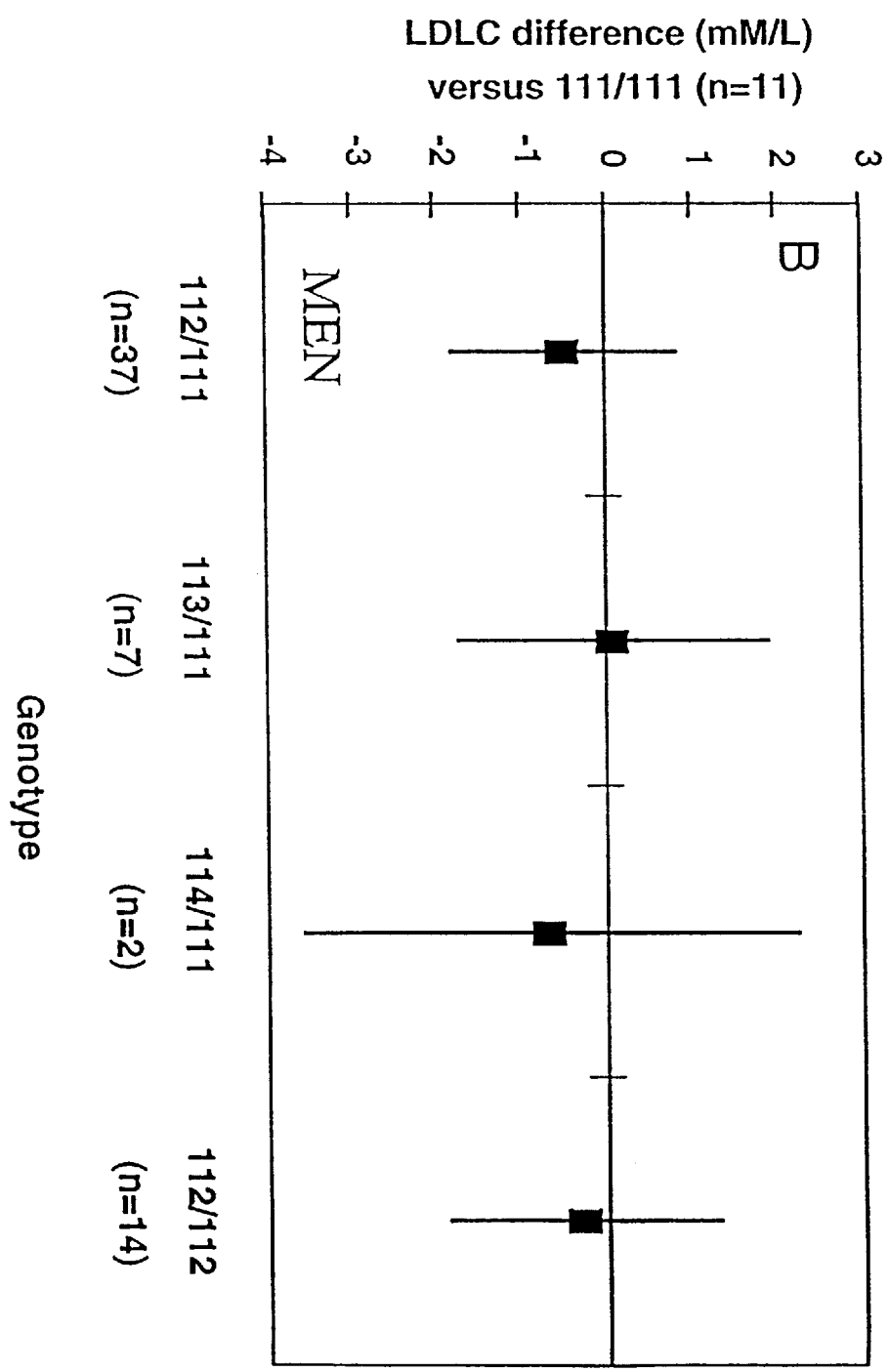
FIG. 5 is a graphic representing the mean LDL-C differences (+/−95% Confidence intervals) between SR-BI genotypes carrying variant alleles and the wild-type genotype (111/111) in men. *significantly different from 111/111 (p<0.030). The differences between genotypes sharing letters are statistically significant (a: p=0.001; b: p=0.016; c: p=0.004).
Figure 6:
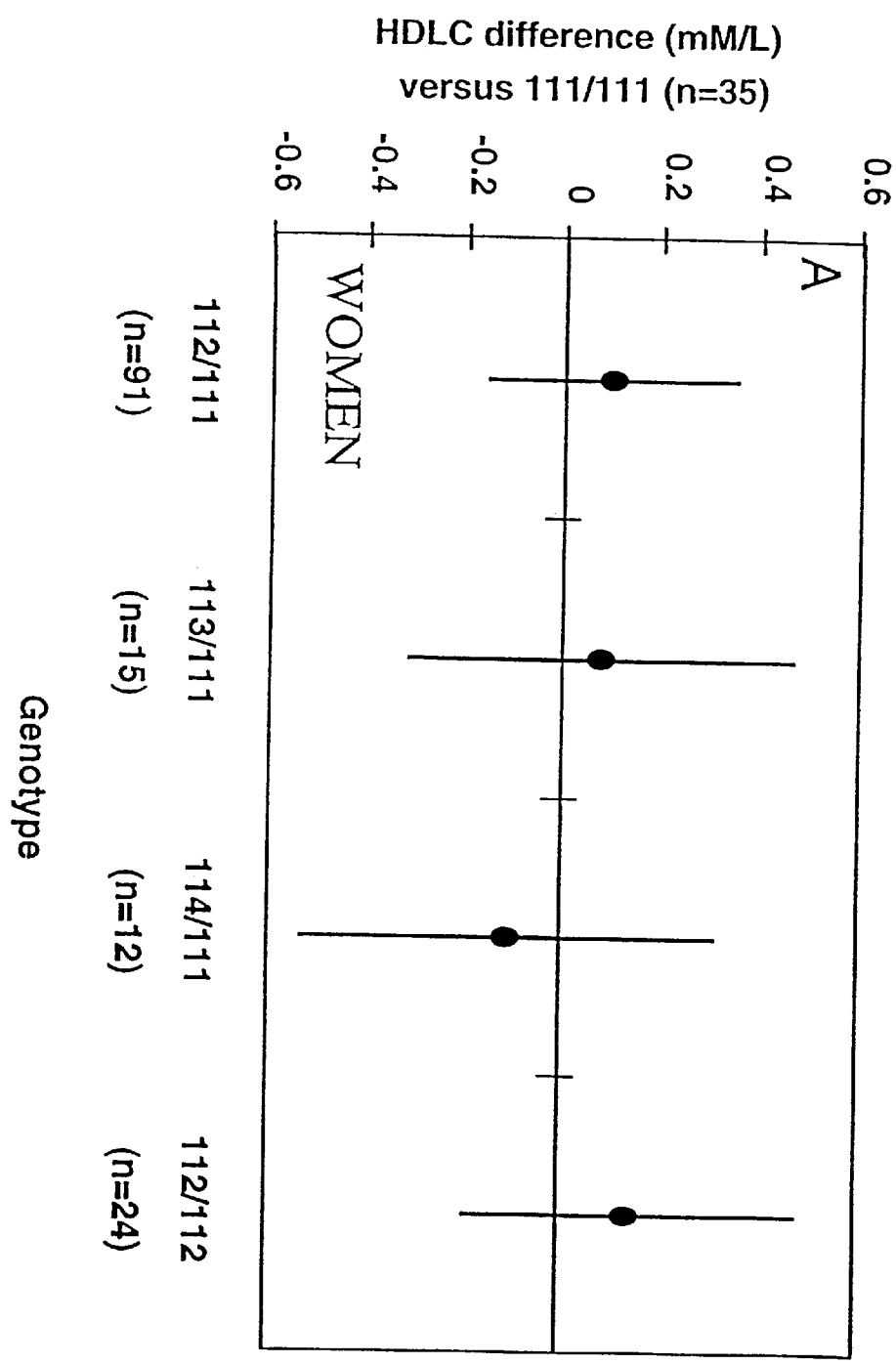
FIG. 6 is a graphic representing mean HDL-C differences (+/−95% Confidence intervals) between SR-BI genotypes carrying variant alleles and the wild-type genotype (111/111) in women.
Figure 7:
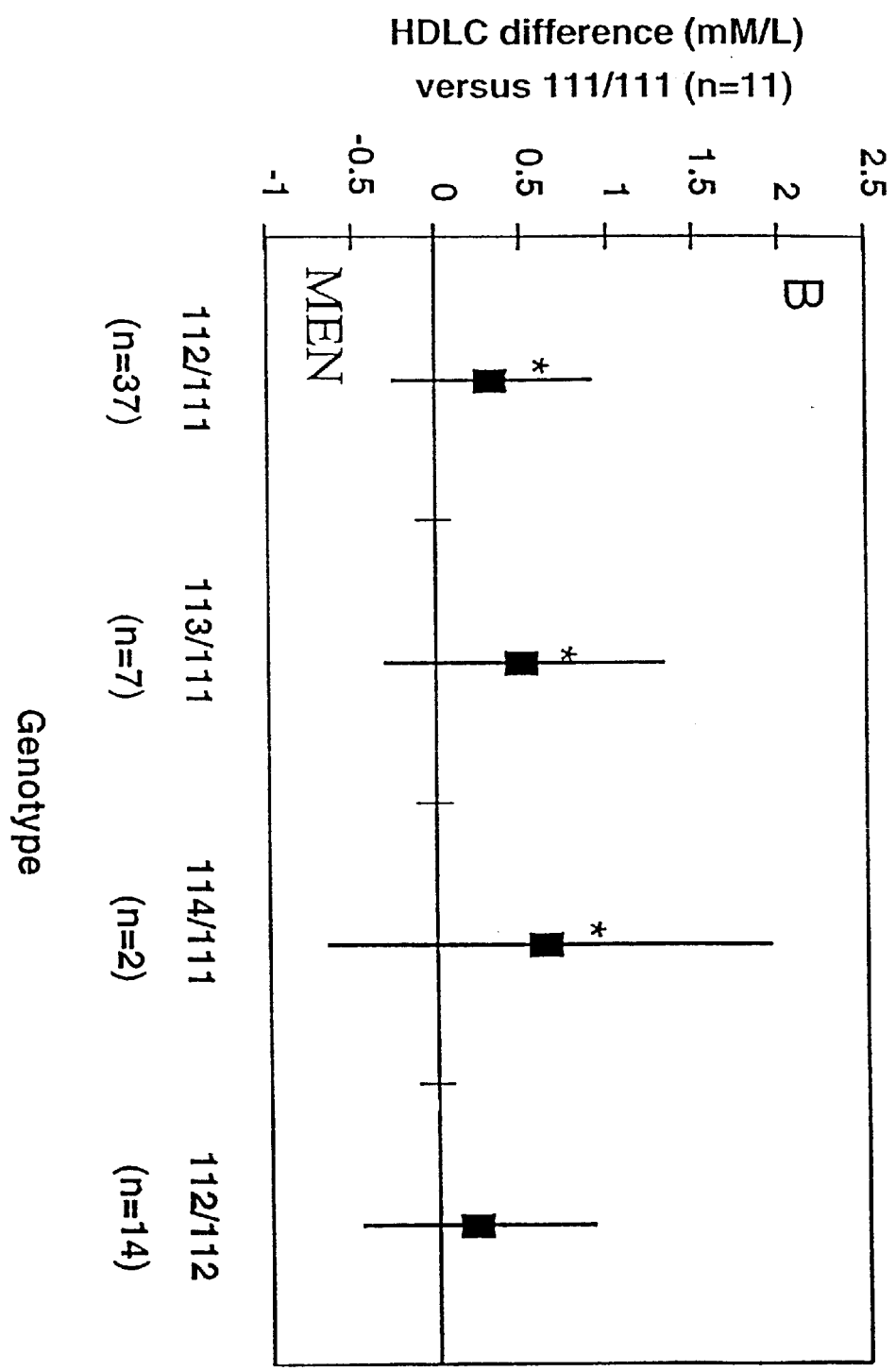
FIG. 7 is a graphic representing mean HDL-C differences (+/−95% Confidence intervals) between SR-BI genotypes carrying variant alleles and the wild-type genotype (111/111) in men. *significantly different from 111/111 (p<0.040).

Haplotype analyses (using the method described by Terwillinger and Ott, 1994, supra) 20 using the three most common polymorphisms identified at this locus (exon 1, intron 5 and exon 8) were carried out. Six possible haplotypes were identified according to the absence (1) or presence (2) of the variant allele at each one of the three polymorphic sites. Four of the haplotypes were common: 111 (wild type); 112 (exon 8 variant); 121 (intron 5 variant); 211 (exon 1 variant); whereas two of the estimated haplotypes were rare: 221 (variants at exon 1 25 and intron 5) and 212 (variants at exons 1 and 8). The most common haplotype, 111, had the highest apparent frequency in women (44.6%) and therefore was considered to be wild-type. Each subject was assigned to the most plausible genotype; however, because of the uncertainty associated with genotype assignments in double heterozygotes when studying unrelated subjects on whom the phase of the polymorphisms cannot be directly ascertained, we used in further analysis only those subjects with unequivocal genotypes. In women, the 111/112 and 112/112 genotypes were found to be associated with lower LDL-C levels as compared with the wild genotype (111/111); whereas the 111/121 genotype was associated with increased LDL-C levels as compared with the 111/112 and 111/211 genotypes (FIG. 4). In men the trends were similar to those observed in women; however, the differences did not reach statistical significance (FIG. 5). In terms of HDL-C levels, all the alleles carrying mutations were associated with increased HDL-C levels in men (FIG. 7); however, no significant effects were observed in women (FIG. 6). Thus, as compared to the wild-type haplotype, the analyses revealed that men with haplotypes 112, 121, and 211 tended to have significantly higher HDL. In fact, those subjects with haplotype 211 (one wild-type chromosome and one with a polymorphism in exon 1) had an average of 75% higher HDL levels than individuals containing only wild-type chromosomes. Such associations were not observed in women. Without wanting to be limited by a specific mechanism of action, it has been shown that, though less efficient than the LDL receptor, SR-BI is able to mediate the degradation of LDL in vitro. SR-BI may also play an indirect role in LDL cholesterol metabolism by altering cholesterol homeostasis in the individual.

Figure 8:
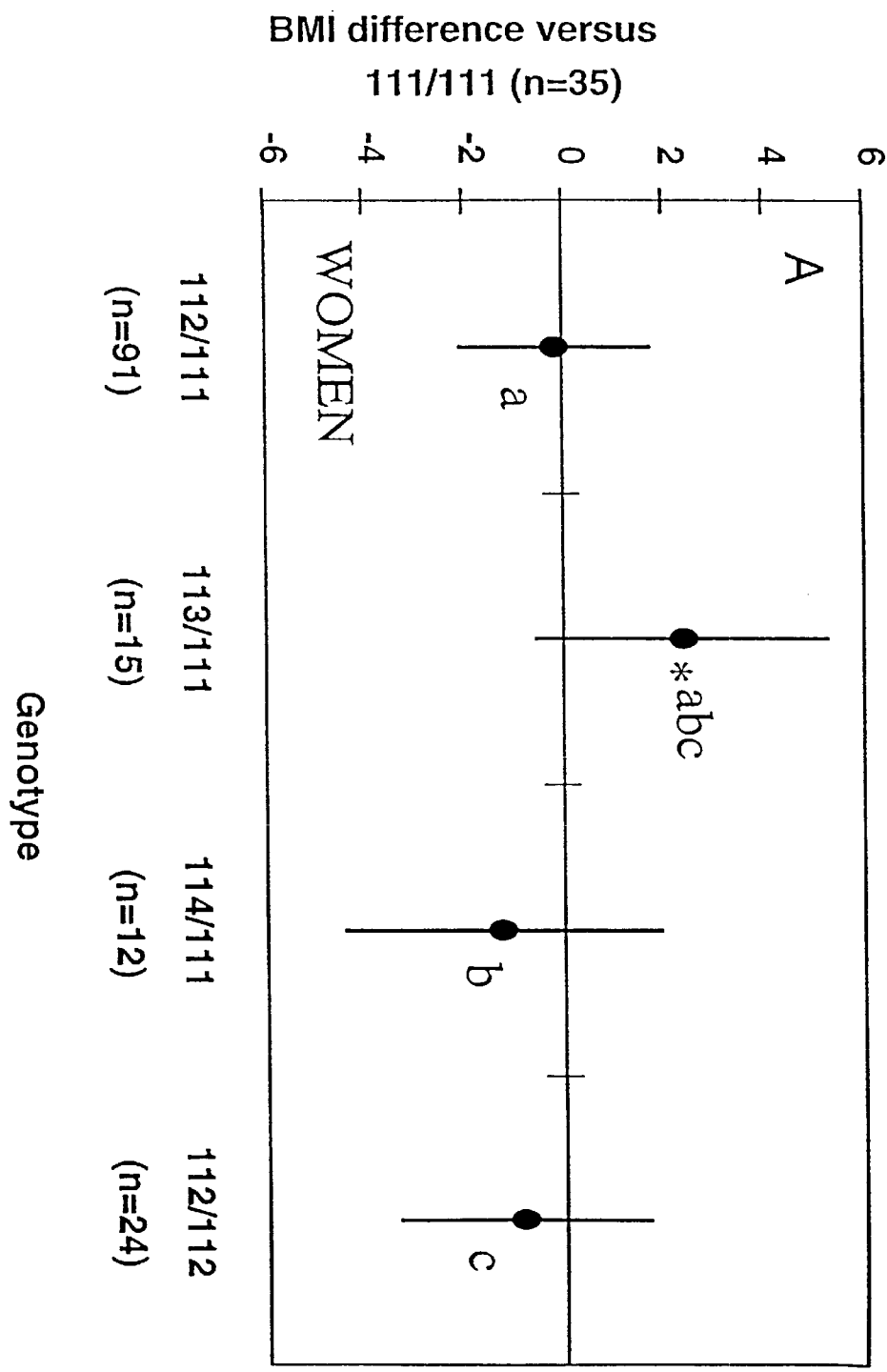
FIG. 8 is a graphic representing mean BMI differences (+/−95% Confidence intervals) between SR-BI genotypes carrying variant alleles and the wild-type genotype (111/111) in women. *significantly different from 111/111 (p=0.020). The differences between genotypes sharing letters are statistically significant (a: p=0.007; b: p=0.005; c: p=0.004).
Figure 9:
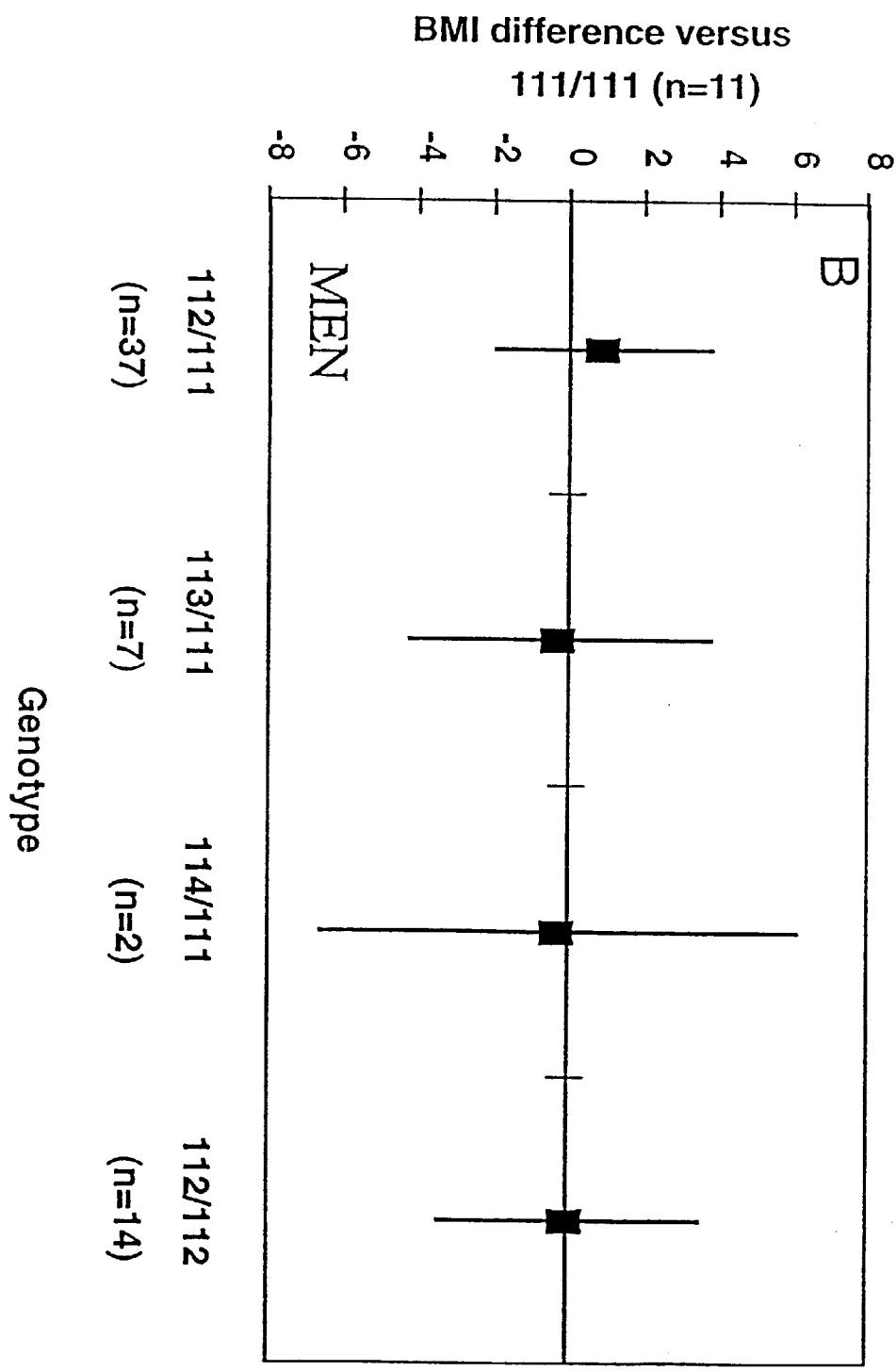
FIG. 9 is a graphic representing mean BMI differences (+/−95% Confidence intervals) between SR-BI genotypes carrying variant alleles and the wild-type genotype (111/111) in men.

The previous association between the intron 5 polymorphism and BMI observed in women using single marker analysis was stronger using haplotype analysis. Subjects carrying the 121 haplotype (n=12), had a mean BMI (25.0"3.3) significantly greater (p<0.05) than that observed in subjects homozygous for the wild haplotype 111 (n=29; 22.8"3.2) and those carriers of the 112 (n=78; 22.8"3.9) and 211 (n=12; 21.5"2.1) haplotypes (FIG. 8). However, no association was observed in men (FIG. 9).

There was also a significant association between the intron 5 polymorphism and BMI in women. The latter finding was most significant in premenopausal women. The 288 female subjects in this study were not considered to be obese. Thus, this effect was observed on individuals within the normal weight range. There are only a few polymorphisms known to date that are associated with BMI values in humans (Bouchard and Perusse (1996) *Obesity Research* 4:81–90), and thus this is a significant finding. Increased body-mass index has been associated with higher mortality from all causes and from cardiovascular disease. For mortality from cardiovascular disease, the relative risk associated with an increment of one in the body-mass index in women in the age range of 30-to-44 year old has been reported to be 1.08 (95 percent confidence interval, 1.05 to 1.11) (Stevens et al. (1998) *N Engl J Med* 338:1–7; Colditz et al. (1995) *Ann Inten Med.* 122(7):481–486). The data presented herein show that for an average woman, the presence of the 121 haplotype raises the BMI by approximately 2.2 kg/m2 which corresponds to about 6 kgs. This increase in BMI could result in an increase in CHD mortality of about 17.6%, primarily due to a greater risk of developing non-insulin dependent diabetes mellitus (Stevens et al. (1998) supra; Colditz et al. (1995) supra), a major risk for coronary artery atherosclerosis. An intriguing observation is the fact that no subjects were found to be homozygous for this polymorphism in this sample of 389 randomly selected individuals, despite the expected frequency of 1% (~4 individuals) assuming Hardy-Weinberg equilibrium.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for determining whether a female subject has, or is at risk of developing, an abnormally high LDL level, comprising determining whether the subject has an allelic variant of a polymorphic region of an SR-BI gene that is associated with an abnormal LDL level, to thereby determine whether the subject has or is at risk of developing an abnormally high LDL level.

2. A method of claim 1, wherein the polymorphic region is located in an exon.

3. A method of claim 2, wherein the exon is exon 8.

4. A method of claim 3, wherein the polymorphic region is a nucleotide polymorphism located at nucleotide 41 of exon 8.

5. A method of claim 4, wherein the presence of a thymidine at nucleotide 41 of exon 8 of an SR-BI gene is indicative that the subject has or is likely to develop a low LDL level.

6. A method of claim 1, wherein the polymorphic region is located in an intron.

7. A method of claim 6, wherein the intron is intron 5.

8. A method of claim 7, wherein the polymorphic region is a nucleotide polymorphism located at nucleotide 54 of intron 5.

9. A method of claim 8, wherein the presence of a thymidine at nucleotide 54 of intron 5 of an SR-BI gene is indicative that the subject has or is at risk of developing an abnormally high LDL level.

10. A method for determining whether a male subject has, or is at risk of developing, an abnormally low HDL level, comprising determining whether the subject has an allelic variant of a polymorphic region of an SR-BI gene that is associated with high HDL levels, wherein the presence of an allelic variant that is associated with high HDL levels indicates that the subject has or is likely to develop a high HDL level.

11. A method of claim 10, comprising determining whether the subject comprises an adenine at nucleotide 146 in exon 1, a thymidine at nucleotide 41 in exon 8 and/or a thymidine at nucleotide 54 in intron 5, wherein the presence of an adenine at nucleotide 146 of exon 1, the presence of a thymidine at nucleotide 41 of exon 8 and/or the presence of a thymidine at nucleotide 54 of intron 5 indicates that the subject has or is a high HDL level.

12. A method of claim 1, comprising contacting a nucleic acid of the subject with at least one probe or primer which hybridizes specifically to an SR-BI gene.

13. A method of claim 12, wherein the probe or primer hybridizes specifically to a nucleic acid sequence comprising nucleotide 41 of exon 8.

14. A method of claim 13, wherein the probe or primer hybridizes specifically to a nucleic acid sequence comprising a thymidine at nucleotide 41 of exon 8.

15. A method of claim 14, wherein the probe or primer hybridizes specifically to a nucleic acid sequence of SEQ ID NO: 65 or the complement thereof.

16. A method of claim 14, wherein the probe or primer comprises a nucleotide sequence selected from the group consisting of SEQ ID NOs: 67–70.

17. A method of claim 12, wherein the probe or primer hybridizes specifically to a nucleic acid sequence comprising nucleotide 54 of intron 5.

18. A method of claim 17, wherein the probe or primer hybridizes specifically to a nucleic acid sequence comprising a thymidine at nucleotide 54 of intron 5.

19. A method of claim 18, wherein the probe or primer hybridizes specifically to a nucleic acid sequence of SEQ ID NO: 66 or the complement thereof.

20. A method of claim 18, wherein the probe or primer comprises a nucleotide sequence selected from the group consisting of SEQ ID NOs: 79–82.

21. A method of claim 12, wherein the probe or primer is selected from the group consisting of SEQ ID NOs: 49, 50, 55 and 56.

22. A method of claim 12, wherein the probe or primer has a nucleotide sequence from about 15 to about 30 nucleotides.

23. A method of claim 12, wherein the probe or primer is a single stranded nucleic acid.

24. A method of claim 12, wherein the probe or primer is labeled.

25. A method of claim 1, wherein determining whether the subject has an allelic variant of a polymorphic region of the SR-BI gene that is associated with an abnormal LDL level is carried out by allele specific hybridization.

26. A method of claim 1, wherein determining whether the subject has an allelic variant of a polymorphic region of the SR-BI gene that is associated with an abnormal LDL level is carried out by primer specific extension.

27. A method of claim 1, wherein determining whether the subject has an allelic variant of a polymorphic region of the SR-BI gene that is associated with an abnormal LDL level is carried out by oligonucleotide ligation assay.

28. A method of claim 1, wherein determining whether the subject has an allelic variant of a polymorphic region of the SR-BI gene that is associated with an abnormal LDL level is carried out by performing a restriction enzyme analysis.

29. A method of claim 1, wherein determining whether the subject has an allelic variant of a polymorphic region of the SR-BI gene that is associated with an abnormal LDL level is carried out by single-stranded conformation polymorphism.

30. A method of claim 10, comprising contacting a nucleic acid of the subject with at least one probe or primer which hybridizes specifically to an SR-BI gene.

31. A method of claim 30, wherein the probe or primer hybridizes specifically to a nucleic acid sequence comprising nucleotide 41 of exon 8.

32. A method of claim 31, wherein the probe or primer hybridizes specifically to a nucleic acid sequence comprising a thymidine at nucleotide 41 of exon 8.

33. A method of claim 32, wherein the probe or primer hybridizes specifically to a nucleic acid sequence of SEQ ID NO: 65 or the complement -thereof.

34. A method of claim 32, wherein the probe or primer comprises a nucleotide sequence selected from the group consisting of SEQ ID NOs: 67–70.

35. A method of claim 30, wherein the probe or primer hybridizes specifically to a nucleic acid sequence comprising nucleotide 54 of intron 5.

36. A method of claim 35, wherein the probe or primer hybridizes specifically to a nucleic acid sequence comprising a thymidine at nucleotide 54 of intron 5.

37. A method of claim 36, wherein the probe or primer hybridizes specifically to a nucleic acid sequence of SEQ ID NO: 66 or the complement thereof.

38. A method of claim 36, wherein the probe or primer comprises a nucleotide sequence selected from the group consisting of SEQ ID NOs. 79–82.

39. A method of claim 32, wherein the probe or primer hybridizes specifically to a nucleic acid sequence comprising nucleotide nucleotide 146 in exon 1.

40. A method of claim 39, wherein the probe or primes hybridizes specifically to a nucleic acid sequence comprising an adenine at nucleotide 146 in exon 1.

41. A method of claim 40, wherein the probe or primer hybridizes specifically to a nucleic acid sequence of SEQ ID NO: 95 or the complement thereof.

42. A method of claim 40, wherein the probe or primer comprises a nucleotide sequence selected from the group consisting of SEQ ID NOs: 98–101.

43. A method of claim 32, wherein the probe or primer is selected from the group consisting of SEQ ID NOs: 41, 42, 49, 50, 55, and 56.

44. A method of claim 32, wherein the probe or primer has a nucleotide sequence from about 15 to about 30 nucleotides.

45. A method of claim 32, wherein the probe or primer is a single stranded nucleic acid.

46. A method of claim 32, wherein the probe or primer is labeled.

47. A method of claim 10, wherein determining whether the subject has an allelic variant of a polymorphic region of the SR-BI gene that is associated with an abnormally high HDL level is carried out by allele specific hybridization.

48. A method of claim 10, wherein determining whether the subject has an allelic variant of a polymorphic region of the SR-BI gene that is associated with an abnormally high HDL level is carried out by primer specific extension.

49. A method of claim 10, wherein determining whether the subject has an allelic variant of a polymorphic region of the SR-BI gene that is associated with an abnormally high HDL level is carried out by oligonucleotide ligation assay.

50. A method of claim 10, wherein determining whether the subject has an allelic variant of a polymorphic region of the SR-BI gene that is associated with an abnormally high HDL level is carried out by performing a restriction enzyme analysis.

51. A method of claim 10, wherein determining whether the subject has an allelic variant of a polymorphic region of the SR-BI gene that is associated with an abnormally high HDL level is carried out by single-stranded conformation polymorphism.

* * * * *

UNITED STATES PATENT AND TRADEMARK OFFICE
CERTIFICATE OF CORRECTION

PATENT NO. : 6,228,581 B1  Page 1 of 1
DATED : May 8, 2001
INVENTOR(S) : Acton et al.

It is certified that error appears in the above-identified patent and that said Letters Patent is hereby corrected as shown below:

Title page,
Item [54], Insert DIAGNOSTIC ASSAYS AND KITS FOR BODY MASS AND CARDIOVASCULAR DISORDERS Signed and Sealed this First Day of January, 2002

*Attest:*

*Attesting Officer*

JAMES E. ROGAN
*Director of the United States Patent and Trademark Office*

SEQUENCE LISTING

<160> NUMBER OF SEQ ID NOS: 121

<210> SEQ ID NO 1
<211> LENGTH: 2630
<212> TYPE: DNA
<213> ORGANISM: Human
<220> FEATURE:
<221> NAME/KEY: CDS
<222> LOCATION: (119)..(1645)

<400> SEQUENCE: 1

```
accgtgcctc tgcggcctgc gtgcccggag tccccgcctg tgtcgtctct gtcgccgtcc      60
ccgtctcctg ccaggcgcgg agccctgcga gccgcgggtg ggccccaggc gcgcagac       118 atg ggc tgc tcc gcc aaa gcg cgc tgg gct gcc ggg gcg ctg ggc gtc       166
Met Gly Cys Ser Ala Lys Ala Arg Trp Ala Ala Gly Ala Leu Gly Val
 1               5                  10                  15 gcg ggg cta ctg tgc gct gtg ctg ggc gct gtc atg atc gtg atg gtg       214
Ala Gly Leu Leu Cys Ala Val Leu Gly Ala Val Met Ile Val Met Val
                 20                  25                  30 ccg tcg ctc atc aag cag cag gtc ctt aag aac gtg cgc atc gac ccc       262
Pro Ser Leu Ile Lys Gln Gln Val Leu Lys Asn Val Arg Ile Asp Pro
             35                  40                  45 agt agc ctg tcc ttc aac atg tgg aag gag atc cct atc ccc ttc tat       310
Ser Ser Leu Ser Phe Asn Met Trp Lys Glu Ile Pro Ile Pro Phe Tyr
         50                  55                  60 ctc tcc gtc tac ttc ttt gac gtc atg aac ccc agc gag atc ctg aag       358
Leu Ser Val Tyr Phe Phe Asp Val Met Asn Pro Ser Glu Ile Leu Lys
 65                  70                  75                  80 ggc gag aag ccg cag gtg cgg gag cgc ggg ccc tac gtg tac agg gag       406
Gly Glu Lys Pro Gln Val Arg Glu Arg Gly Pro Tyr Val Tyr Arg Glu
                 85                  90                  95 ttc agg cac aaa agc aac atc acc ttc aac aac aac gac acc gtg tcc       454
Phe Arg His Lys Ser Asn Ile Thr Phe Asn Asn Asn Asp Thr Val Ser
                100                 105                 110 ttc ctc gag tac cgc acc ttc cag ttc cag ccc tcc aag tcc cac ggc       502
Phe Leu Glu Tyr Arg Thr Phe Gln Phe Gln Pro Ser Lys Ser His Gly
            115                 120                 125 tcg gag agc gac tac atc gtc atg ccc aac atc ctg gtc ttg ggt gcg       550
Ser Glu Ser Asp Tyr Ile Val Met Pro Asn Ile Leu Val Leu Gly Ala
        130                 135                 140 gcg gtg atg atg gag aat aag ccc atg acc ctg aag ctc atc atg acc       598
Ala Val Met Met Glu Asn Lys Pro Met Thr Leu Lys Leu Ile Met Thr
145                 150                 155                 160 ttg gca ttc acc acc ctc ggc gaa cgt gcc ttc atg aac cgc act gtg       646
Leu Ala Phe Thr Thr Leu Gly Glu Arg Ala Phe Met Asn Arg Thr Val
                165                 170                 175 ggt gag atc atg tgg ggc tac aag gac ccc ctt gtg aat ctc atc aac       694
Gly Glu Ile Met Trp Gly Tyr Lys Asp Pro Leu Val Asn Leu Ile Asn
                180                 185                 190 aag tac ttt cca ggc atg ttc ccc ttc aag gac aag ttc gga tta ttt       742
Lys Tyr Phe Pro Gly Met Phe Pro Phe Lys Asp Lys Phe Gly Leu Phe
            195                 200                 205 gct gag ctc aac aac tcc gac tct ggg ctc ttc acg gtg ttc acg ggg       790
Ala Glu Leu Asn Asn Ser Asp Ser Gly Leu Phe Thr Val Phe Thr Gly
        210                 215                 220 gtc cag aac atc agc agg atc cac ctc gtg gac aag tgg aac ggg ctg       838
Val Gln Asn Ile Ser Arg Ile His Leu Val Asp Lys Trp Asn Gly Leu
225                 230                 235                 240
```

```
agc aag gtt gac ttc tgg cat tcc gat cag tgc aac atg atc aat gga       886
Ser Lys Val Asp Phe Trp His Ser Asp Gln Cys Asn Met Ile Asn Gly
            245                 250                 255 act tct ggg caa atg tgg ccg ccc ttc atg act cct gag tcc tcg ctg       934
Thr Ser Gly Gln Met Trp Pro Pro Phe Met Thr Pro Glu Ser Ser Leu
            260                 265                 270 gag ttc tac agc ccg gag gcc tgc cga tcc atg aag cta atg tac aag       982
Glu Phe Tyr Ser Pro Glu Ala Cys Arg Ser Met Lys Leu Met Tyr Lys
            275                 280                 285 gag tca ggg gtg ttt gaa ggc atc ccc acc tat cgc ttc gtg gct ccc      1030
Glu Ser Gly Val Phe Glu Gly Ile Pro Thr Tyr Arg Phe Val Ala Pro
            290                 295                 300 aaa acc ctg ttt gcc aac ggg tcc atc tac cca ccc aac gaa ggc ttc      1078
Lys Thr Leu Phe Ala Asn Gly Ser Ile Tyr Pro Pro Asn Glu Gly Phe
305                 310                 315                 320 tgc ccg tgc ctg gag tct gga att cag aac gtc agc acc tgc agg ttc      1126
Cys Pro Cys Leu Glu Ser Gly Ile Gln Asn Val Ser Thr Cys Arg Phe
            325                 330                 335 agt gcc ccc ttg ttt ctc tcc cat cct cac ttc ctc aac gcc gac ccg      1174
Ser Ala Pro Leu Phe Leu Ser His Pro His Phe Leu Asn Ala Asp Pro
            340                 345                 350 gtt ctg gca gaa gcg gtg act ggc ctg cac cct aac cag gag gca cac      1222
Val Leu Ala Glu Ala Val Thr Gly Leu His Pro Asn Gln Glu Ala His
            355                 360                 365 tcc ttg ttc ctg gac atc cac ccg gtc acg gga atc ccc atg aac tgc      1270
Ser Leu Phe Leu Asp Ile His Pro Val Thr Gly Ile Pro Met Asn Cys
            370                 375                 380 tct gtg aaa ctg cag ctg agc ctc tac atg aaa tct gtc gca ggc att      1318
Ser Val Lys Leu Gln Leu Ser Leu Tyr Met Lys Ser Val Ala Gly Ile
385                 390                 395                 400 gga caa act ggg aag att gag cct gtg gtc ctg ccg ctg ctc tgg ttt      1366
Gly Gln Thr Gly Lys Ile Glu Pro Val Val Leu Pro Leu Leu Trp Phe
            405                 410                 415 gca gag agc ggg gcc atg gag ggg gag act ctt cac aca ttc tac act      1414
Ala Glu Ser Gly Ala Met Glu Gly Glu Thr Leu His Thr Phe Tyr Thr
            420                 425                 430 cag ctg gtg ttg atg ccc aag gtg atg cac tat gcc cag tac gtc ctc      1462
Gln Leu Val Leu Met Pro Lys Val Met His Tyr Ala Gln Tyr Val Leu
            435                 440                 445 ctg gcg ctg ggc tgc gtc ctg ctg gtc cct gtc atc tgc caa atc         1510
Leu Ala Leu Gly Cys Val Leu Leu Val Pro Val Ile Cys Gln Ile
450                 455                 460 cgg agc caa gag aaa tgc tat tta ttt tgg agt agt agt aaa aag ggc      1558
Arg Ser Gln Glu Lys Cys Tyr Leu Phe Trp Ser Ser Ser Lys Lys Gly
465                 470                 475                 480 tca aag gat aag gag gcc att cag gcc tat tct gaa tcc ctg atg aca      1606
Ser Lys Asp Lys Glu Ala Ile Gln Ala Tyr Ser Glu Ser Leu Met Thr
            485                 490                 495 tca gct ccc aag ggc tct gtg ctg cag gaa gca aaa ctg tagggtcctg      1655
Ser Ala Pro Lys Gly Ser Val Leu Gln Glu Ala Lys Leu
            500                 505 aggacaccgt gagccagcca ggcctggccg ctgggcctga ccggccccccc agcccctaca  1715 ccccgcttct cccggactct cccagcagac agcccccccag ccccacagcc tgagcctccc  1775
agctgccatg tgcctgttgc acacctgcac acacgccctg gcacacatac acacatgcgt  1835
gcaggcttgt gcagacactc agggatggag ctgctgctga agggacttgt agggagaggc  1895
tcgtcaacaa gcactgttct ggaaccttct ctccacgtgg cccacaggcc tgaccacagg  1955
ggctgtgggt cctgcgtccc cttcctcggg tgagcctggc ctgtcccgtt cagccgttgg  2015
```

-continued

```
gcccaggctt cctcccctcc aaggtgaaac actgcagtcc cggtgtggtg gctccccatg      2075
caggacgggc caggctggga gtgccgcctt cctgtgccaa attcagtggg gactcagtgc      2135
ccaggccctg gccacgagct ttggccttgg tctacctgcc aggccaggca aagcgccttt      2195
acacaggcct cggaaaacaa tggagtgagc acaagatgcc ctgtgcagct gcccgagggt      2255
ctccgcccac cccggccgga ctttgatccc cccgaagtct tcacaggcac tgcatcgggt      2315
tgtctggcgc ccttttcctc cagcctaaac tgacatcatc ctatggactg agccggccac      2375
tytytggccg aagtggccgc aggctgtgcc cccgagctgc ccccacccccc tcacagggtc      2435 cctcagatta taggtgccca ggctgaggtg aagaggcctg ggggccctgc cttccgggcg      2495
ctcctggacc ctggggcaaa cctgtgaccc ttttctactg gaatagaaat gagttttatc      2555
atctttgaaa aataattcac tcttgaagta ataaacgttt aaaaaaatgg gaaaaaaaaa      2615
aaaaaaaaaa aaaaa                                                        2630
```

<210> SEQ ID NO 2
<211> LENGTH: 509
<212> TYPE: PRT
<213> ORGANISM: Human

<400> SEQUENCE: 2

```
Met Gly Cys Ser Ala Lys Ala Arg Trp Ala Ala Gly Ala Leu Gly Val
 1               5                   10                  15

Ala Gly Leu Leu Cys Ala Val Leu Gly Ala Val Met Ile Val Met Val
                20                  25                  30

Pro Ser Leu Ile Lys Gln Gln Val Leu Lys Asn Val Arg Ile Asp Pro
            35                  40                  45

Ser Ser Leu Ser Phe Asn Met Trp Lys Glu Ile Pro Ile Pro Phe Tyr
        50                  55                  60

Leu Ser Val Tyr Phe Phe Asp Val Met Asn Pro Ser Glu Ile Leu Lys
    65                  70                  75                  80

Gly Glu Lys Pro Gln Val Arg Glu Arg Gly Pro Tyr Val Tyr Arg Glu
                85                  90                  95

Phe Arg His Lys Ser Asn Ile Thr Phe Asn Asn Asn Asp Thr Val Ser
               100                 105                 110

Phe Leu Glu Tyr Arg Thr Phe Gln Phe Gln Pro Ser Lys Ser His Gly
           115                 120                 125

Ser Glu Ser Asp Tyr Ile Val Met Pro Asn Ile Leu Val Leu Gly Ala
       130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
            180                 185                 190

Lys Tyr Phe Pro Gly Met Phe Pro Phe Lys Asp Lys Phe Gly Leu Phe
        195                 200                 205

Ala Glu Leu Asn Asn Ser Asp Ser Gly Leu Phe Thr Val Phe Thr Gly
    210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255
```

```
Thr Ser Gly Gln Met Trp Pro Pro Phe Met Thr Pro Glu Ser Ser Leu
        260                 265                 270

Glu Phe Tyr Ser Pro Glu Ala Cys Arg Ser Met Lys Leu Met Tyr Lys
        275                 280                 285

Glu Ser Gly Val Phe Glu Gly Ile Pro Thr Tyr Arg Phe Val Ala Pro
        290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Ser Ala Pro Leu Phe Leu Ser His Pro His Phe Leu Asn Ala Asp Pro
                340                 345                 350

Val Leu Ala Glu Ala Val Thr Gly Leu His Pro Asn Gln Glu Ala His
                355                 360                 365

Ser Leu Phe Leu Asp Ile His Pro Val Thr Gly Ile Pro Met Asn Cys
370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Val Leu Pro Leu Leu Trp Phe
                405                 410                 415

Ala Glu Ser Gly Ala Met Glu Gly Glu Thr Leu His Thr Phe Tyr Thr
                420                 425                 430

Gln Leu Val Leu Met Pro Lys Val Met His Tyr Ala Gln Tyr Val Leu
                435                 440                 445

Leu Ala Leu Gly Cys Val Leu Leu Val Pro Val Ile Cys Gln Ile
450                 455                 460

Arg Ser Gln Glu Lys Cys Tyr Leu Phe Trp Ser Ser Lys Lys Gly
465                 470                 475                 480

Ser Lys Asp Lys Glu Ala Ile Gln Ala Tyr Ser Glu Ser Leu Met Thr
                485                 490                 495

Ser Ala Pro Lys Gly Ser Val Leu Gln Glu Ala Lys Leu
                500                 505

<210> SEQ ID NO 3
<211> LENGTH: 1825
<212> TYPE: DNA
<213> ORGANISM: Human
<220> FEATURE:
<221> NAME/KEY: CDS
<222> LOCATION: (156)..(1682)

<400> SEQUENCE: 3
gccacctgca gggctactgc tgctccggcc actgcctgag actcaccttg ctggaacgtg      60
agcctcggct tctgtcatct ctgtggcctc tgtcgcttct gtcgctgtcc cccttcagtc     120
cctgagcccc gcgagcccgg ccgcacacg cggac atg ggc ggc agc gcc agg         173
                                    Met Gly Gly Ser Ala Arg
                                      1               5 gcg cgc tgg gtg gcg gtg ggg ctg ggc gtc gtg ggg ctg ctg tgc gct      221
Ala Arg Trp Val Ala Val Gly Leu Gly Val Val Gly Leu Leu Cys Ala
            10                  15                  20 gtg ctc ggt gtg gtt atg atc ctc gtg atg ccc tcg ctc atc aaa cag      269
Val Leu Gly Val Val Met Ile Leu Val Met Pro Ser Leu Ile Lys Gln
        25                  30                  35 cag gta ctg aag aat gtc cgc ata gac ccc agc agc ctg tcc ttt gca      317
Gln Val Leu Lys Asn Val Arg Ile Asp Pro Ser Ser Leu Ser Phe Ala
    40                  45                  50
```

| | | |
|---|---|---|
| atg tgg aag gag atc cct gta ccc ttc tac ttg tcc gtc tac ttc ttc<br>Met Trp Lys Glu Ile Pro Val Pro Phe Tyr Leu Ser Val Tyr Phe Phe<br>55                        60                    65               70 | 365 |
| gag gtg gtc aat ccc agc gag atc cta aag ggt gag aag cca gta gtg<br>Glu Val Val Asn Pro Ser Glu Ile Leu Lys Gly Glu Lys Pro Val Val<br>                  75                    80                    85 | 413 |
| cgg gag cgt gga ccc tat gtc tac agg gaa ttc aga cat aag gcc aac<br>Arg Glu Arg Gly Pro Tyr Val Tyr Arg Glu Phe Arg His Lys Ala Asn<br>               90                    95                  100 | 461 |
| atc acc ttc aat gac aat gat act gtg tcc ttt gtg gag cac cgc agc<br>Ile Thr Phe Asn Asp Asn Asp Thr Val Ser Phe Val Glu His Arg Ser<br>            105                    110                 115 | 509 |
| ctc cat ttc cag ccg gac agg tcc cac ggc tct gag agt gac tac att<br>Leu His Phe Gln Pro Asp Arg Ser His Gly Ser Glu Ser Asp Tyr Ile<br>120                      125                  130 | 557 |
| ata ctg cct aac att ctg gtc ttg ggg ggc gca gta atg atg gag agc<br>Ile Leu Pro Asn Ile Leu Val Leu Gly Gly Ala Val Met Met Glu Ser<br>135                      140                  145               150 | 605 |
| aag tct gca ggc ctg aag ctg atg atg acc ttg ggg ctg gcc acc ttg<br>Lys Ser Ala Gly Leu Lys Leu Met Met Thr Leu Gly Leu Ala Thr Leu<br>                  155                   160                 165 | 653 |
| ggc cag cgt gcc ttt atg aac cga aca gtt ggt gag atc ctg tgg ggc<br>Gly Gln Arg Ala Phe Met Asn Arg Thr Val Gly Glu Ile Leu Trp Gly<br>                170                    175               180 | 701 |
| tat gag gat ccc ttc gtg aat ttt atc aac aaa tac tta cca gac atg<br>Tyr Glu Asp Pro Phe Val Asn Phe Ile Asn Lys Tyr Leu Pro Asp Met<br>185                      190                  195 | 749 |
| ttc ccc atc aag ggc aag ttc ggc ctg ttt gtt gag atg aac aac tca<br>Phe Pro Ile Lys Gly Lys Phe Gly Leu Phe Val Glu Met Asn Asn Ser<br>200                      205                  210 | 797 |
| gac tct ggg ctc ttc act gtg ttc acg ggc gtc cag aac ttc agc aag<br>Asp Ser Gly Leu Phe Thr Val Phe Thr Gly Val Gln Asn Phe Ser Lys<br>215                      220                  225               230 | 845 |
| atc cac ctg gtg gac aga tgg aat ggg ctc agc aag gtc aac tac tgg<br>Ile His Leu Val Asp Arg Trp Asn Gly Leu Ser Lys Val Asn Tyr Trp<br>                235                    240               245 | 893 |
| cat tca gag cag tgc aac atg atc aat ggc act tcc ggg cag atg tgg<br>His Ser Glu Gln Cys Asn Met Ile Asn Gly Thr Ser Gly Gln Met Trp<br>                   250                   255               260 | 941 |
| gca cca ttc atg aca ccc cag tcc tcg ctg gaa ttc ttc agt ccg gaa<br>Ala Pro Phe Met Thr Pro Gln Ser Ser Leu Glu Phe Phe Ser Pro Glu<br>265                      270                  275 | 989 |
| gcc tgc agg tct atg aag ctc acc tac cat gat tca ggg gtg ttt gaa<br>Ala Cys Arg Ser Met Lys Leu Thr Tyr His Asp Ser Gly Val Phe Glu<br>280                      285                  290 | 1037 |
| ggc atc ccc acc tat cgc ttc aca gcc cct aaa act ttg ttt gcc aat<br>Gly Ile Pro Thr Tyr Arg Phe Thr Ala Pro Lys Thr Leu Phe Ala Asn<br>295                      300                  305               310 | 1085 |
| ggg tct gtt tac cca ccc aat gaa ggt ttc tgc ccg tgc ctt gaa tcc<br>Gly Ser Val Tyr Pro Pro Asn Glu Gly Phe Cys Pro Cys Leu Glu Ser<br>                315                    320               325 | 1133 |
| ggc att caa aat gtc agc act tgc agg ttt ggt gca ccc ctg ttt ctg<br>Gly Ile Gln Asn Val Ser Thr Cys Arg Phe Gly Ala Pro Leu Phe Leu<br>                330                    335               340 | 1181 |
| tca cac cct cac ttc tac aat gca gac cct gtg cta tca gaa gcc gtt<br>Ser His Pro His Phe Tyr Asn Ala Asp Pro Val Leu Ser Glu Ala Val<br>                345                    350               355 | 1229 |
| ctg ggt ctg aac cct gac cca agg gag cat tct ttg ttc ctt gac atc<br>Leu Gly Leu Asn Pro Asp Pro Arg Glu His Ser Leu Phe Leu Asp Ile<br>360                      365                  370 | 1277 |

-continued

```
cat ccg gtc act ggg atc ccc atg aac tgt tct gtg aag ttg cag ata    1325
His Pro Val Thr Gly Ile Pro Met Asn Cys Ser Val Lys Leu Gln Ile
375                 380                 385                 390 agc ctc tac atc aaa gct gtc aag ggc att ggg caa aca ggg aag atc    1373
Ser Leu Tyr Ile Lys Ala Val Lys Gly Ile Gly Gln Thr Gly Lys Ile
                395                 400                 405 gag ccc gtg gtc ctc cca ttg ctg tgg ttt gag cag agc ggt gcc atg    1421
Glu Pro Val Val Leu Pro Leu Leu Trp Phe Glu Gln Ser Gly Ala Met
            410                 415                 420 ggc ggc gag ccc ctg aac acg ttc tac acg cag ctg gtg ctg atg ccc    1469
Gly Gly Glu Pro Leu Asn Thr Phe Tyr Thr Gln Leu Val Leu Met Pro
        425                 430                 435 cag gta ctt cag tat gtg cag tat gtg ctg ctg ggg ctg ggc ggc ctc    1517
Gln Val Leu Gln Tyr Val Gln Tyr Val Leu Leu Gly Leu Gly Gly Leu
440                 445                 450 ctg ctg ctg gtg ccc gtc atc tac cag ttg cgc agc cag gag aaa tgc    1565
Leu Leu Leu Val Pro Val Ile Tyr Gln Leu Arg Ser Gln Glu Lys Cys
455                 460                 465                 470 ttt tta ttt tgg agt ggt agt aaa aag ggc tcg cag gat aag gag gcc    1613
Phe Leu Phe Trp Ser Gly Ser Lys Lys Gly Ser Gln Asp Lys Glu Ala
                475                 480                 485 att cag gcc tac tct gag tct ctg atg tca cca gct gcc aag ggc acg    1661
Ile Gln Ala Tyr Ser Glu Ser Leu Met Ser Pro Ala Ala Lys Gly Thr
            490                 495                 500 gtg ctg caa gaa gcc aag ctg tagggtccca aagacaccac gagccccccc      1712
Val Leu Gln Glu Ala Lys Leu
        505 aacctgatag cttggtcaga ccagccatcc agcccctaca ccccgcttct tgaggactct  1772 ctcagcggac agtccgccag tgccatggcc tgagcccag atgtcacacc tgt          1825

<210> SEQ ID NO 4
<211> LENGTH: 509
<212> TYPE: PRT
<213> ORGANISM: Human

<400> SEQUENCE: 4

Met Gly Gly Ser Ala Arg Ala Arg Trp Val Ala Val Gly Leu Gly Val
 1               5                  10                  15

Val Gly Leu Leu Cys Ala Val Leu Gly Val Val Met Ile Leu Val Met
                20                  25                  30

Pro Ser Leu Ile Lys Gln Gln Val Leu Lys Asn Val Arg Ile Asp Pro
            35                  40                  45

Ser Ser Leu Ser Phe Ala Met Trp Lys Glu Ile Pro Val Pro Phe Tyr
        50                  55                  60

Leu Ser Val Tyr Phe Phe Glu Val Val Asn Pro Ser Glu Ile Leu Lys
65                  70                  75                  80

Gly Glu Lys Pro Val Val Arg Glu Arg Gly Pro Tyr Val Tyr Arg Glu
                85                  90                  95

Phe Arg His Lys Ala Asn Ile Thr Phe Asn Asp Asn Asp Thr Val Ser
            100                 105                 110

Phe Val Glu His Arg Ser Leu His Phe Gln Pro Asp Arg Ser His Gly
        115                 120                 125

Ser Glu Ser Asp Tyr Ile Ile Leu Pro Asn Ile Leu Val Leu Gly Gly
    130                 135                 140

Ala Val Met Met Glu Ser Lys Ser Ala Gly Leu Lys Leu Met Met Thr
145                 150                 155                 160
```

```
Leu Gly Leu Ala Thr Leu Gly Gln Arg Ala Phe Met Asn Arg Thr Val
            165                 170                 175
Gly Glu Ile Leu Trp Gly Tyr Glu Asp Pro Phe Val Asn Phe Ile Asn
        180                 185                 190
Lys Tyr Leu Pro Asp Met Phe Pro Ile Lys Gly Lys Phe Gly Leu Phe
    195                 200                 205
Val Glu Met Asn Asn Ser Asp Ser Gly Leu Phe Thr Val Phe Thr Gly
210                 215                 220
Val Gln Asn Phe Ser Lys Ile His Leu Val Asp Arg Trp Asn Gly Leu
225                 230                 235                 240
Ser Lys Val Asn Tyr Trp His Ser Glu Gln Cys Asn Met Ile Asn Gly
                245                 250                 255
Thr Ser Gly Gln Met Trp Ala Pro Phe Met Thr Pro Gln Ser Ser Leu
            260                 265                 270
Glu Phe Phe Ser Pro Glu Ala Cys Arg Ser Met Lys Leu Thr Tyr His
        275                 280                 285
Asp Ser Gly Val Phe Glu Gly Ile Pro Thr Tyr Arg Phe Thr Ala Pro
    290                 295                 300
Lys Thr Leu Phe Ala Asn Gly Ser Val Tyr Pro Pro Asn Glu Gly Phe
305                 310                 315                 320
Cys Pro Cys Leu Glu Ser Gly Ile Gln Asn Val Ser Thr Cys Arg Phe
                325                 330                 335
Gly Ala Pro Leu Phe Leu Ser Pro His Phe Tyr Asn Ala Asp Pro
            340                 345                 350
Val Leu Ser Glu Ala Val Leu Gly Leu Asn Pro Asp Pro Arg Glu His
        355                 360                 365
Ser Leu Phe Leu Asp Ile His Pro Val Thr Gly Ile Pro Met Asn Cys
    370                 375                 380
Ser Val Lys Leu Gln Ile Ser Leu Tyr Ile Lys Ala Val Lys Gly Ile
385                 390                 395                 400
Gly Gln Thr Gly Lys Ile Glu Pro Val Val Leu Pro Leu Leu Trp Phe
                405                 410                 415
Glu Gln Ser Gly Ala Met Gly Gly Glu Pro Leu Asn Thr Phe Tyr Thr
            420                 425                 430
Gln Leu Val Leu Met Pro Gln Val Leu Gln Tyr Val Gln Tyr Val Leu
        435                 440                 445
Leu Gly Leu Gly Gly Leu Leu Leu Val Pro Val Ile Tyr Gln Leu
    450                 455                 460
Arg Ser Gln Glu Lys Cys Phe Leu Phe Trp Ser Gly Ser Lys Lys Gly
465                 470                 475                 480
Ser Gln Asp Lys Glu Ala Ile Gln Ala Tyr Ser Glu Ser Leu Met Ser
                485                 490                 495
Pro Ala Ala Lys Gly Thr Val Leu Gln Glu Ala Lys Leu
            500                 505
```

<210> SEQ ID NO 5
<211> LENGTH: 1002
<212> TYPE: DNA
<213> ORGANISM: Human

<400> SEQUENCE: 5

```
actgcggaga tgagggtcta gaaggtggtg gcggggcatg tggaccgttg taagggctct    60
ggggttcctg ggtgggctgg cgaagtccta ctcacagtga ccaaccatga tgatggtccc   120
gatagaggag gagagggagg aggagggaaa aggaagggtg aggggctcag aggggagagc   180
```

-continued

```
tgggaggagg ggagacatag gtgggggaag gggtaggaga aaggggaagg gagcaagagg      240
gtgaggggca ccaggcccca tagacgtttt ggctcagcgg ccacgaggct tcatcagctc      300
ccgccccaaa acggaagcga ggccgtgggg gcagcggcag catggcgggg cttgtcttgg      360
cggccatggc cccgcccct gcccgtccga tcagcgcccc gccccgtccc cgccccgacc       420
ccgcccgggg cccgctcagg ccccgcccct gccgccggaa tcctgaagcc caaggctgcc     480
cgggggcggt ccggcggcgc cggcgatggg gcataaaacc actggccacc tgccgggctg     540
ctcctgcgtg cgctgccgtc ccggatccac cgtgcctctg cggcctgcgt gccccgagtc    600
cccgcctgtg tcgtctctgt cgccgtcccc gtctcctgcc aggcgcggag ccctgcgagc    660
cgcgggtggg ccccaggcgc gcagacatgg gctgctccgc caaagcgcgc tgggctgccg   720
ggcgctgggg cgtcgcgggg ctactgtgcg ctgtgctggg cgctgtcatg atcgtgatgg   780
tgccgtcgct catcaagcag caggtcctta aggtgggtga gggagacccc aggggtccg    840 cgcacggacc cgggctgttg ggcgctgggc gccgggagga cccgcgcgtt gcggtgggtg   900
ggcgaccgca gcggaatcgg cgcccgggcc tggcgccgca gaacacgagg gaggccaggc    960
gcttcgggag gggctgctgc ccgcctcccc accaccctca cc                      1002
```

<210> SEQ ID NO 6
<211> LENGTH: 479
<212> TYPE: DNA
<213> ORGANISM: Human

<400> SEQUENCE: 6

```
agcctcatgt gcgaagggct ttcccaccac ctcctatccc aagctcccgc cgaggagccc      60
cttccctggc cgggctcggg cagctgttcc ggagccttgt ggtggggcgt ggggccctca    120
tcactctcct cacaagcgta cttgtcccctt cccctgcaga acgtgcgcat cgaccccagt   180
agcctgtcct tcaacatgtg gaaggagatc cctatcccct tctatctctc cgtctacttc    240
tttgacgtca tgaaccccag cgagatcctg aagggcgaga gccgcaggt gcgggagcgc    300 gggccctacg tgtacaggtg aggctgtgtc cacgtgatgg tggacgggcc ggctgacgct    360
gggcatggga cgggtctcaa gtggacggga tggggaggct gctgactgac ccccaaacat    420
tgttccggaa gcacgcaact catagtcggg gtaagtgcta ctcccaaaaa agtttgcgt    479
```

<210> SEQ ID NO 7
<211> LENGTH: 495
<212> TYPE: DNA
<213> ORGANISM: Human

<400> SEQUENCE: 7

```
catgtcctgc agtgggcagg cagcgggagg gacagacttg gcgaagggc cgagctcagc      60 tttggctgtg gggccggagg tgtgcacaga cgtccaggggc ccctggttcc caggcaggca   120
ttgcaggcga gtagaaggga aacgtcccat gcagcggggc ggggcgtctg acccactggc   180 ttccccaca gggagttcag gcacaaaagc aacatcacct tcaacaacaa cgacaccgtg    240
tccttcctcg agtaccgcac cttccagttc cagccctcca gtcccacgg ctcggagagc    300 gactacatcg tcatgcccaa catcctggtc ttggtgaggc tgccctgtgg cccacgcgc    360 ctcgcaccct gacctcgtcc cctgtctctc ctcccgcctg cccttgtgc agagagcagt    420 ccctgaggtg gtcggagcgt ggggactcac gcctggtggg tggctttcgg ccctgtgctg    480
tctccaccac cccca                                                       495
```

<210> SEQ ID NO 8
<211> LENGTH: 526
<212> TYPE: DNA
<213> ORGANISM: Human

<400> SEQUENCE: 8

| | | | | | |
|---|---|---|---|---|---|
| ggtggttctg | gtgtcccaga | tgccccacgt | ggccactcca | ggggcctcct | gcaccccagc | 60 |
| atttcccttc | atgggctctt | tgctgtgagg | cccagctggg | gccaagggag | gatgggccag | 120 |
| ccacgtccag | cctctgacac | tagtgtccct | tcgccttgca | gggtgcggcg | gtgatgatgg | 180 |
| agaataagcc | catgaccctg | aagctcatca | tgaccttggc | attcaccacc | ctcggcgaac | 240 |
| gtgccttcat | gaaccgcact | gtgggtgaga | tcatgtgggg | ctacaaggac | cccttgtgaa | 300 |
| tctcatcaac | aagtactttc | caggcatgtt | ccccttcaag | gacaagttcg | gattatttgc | 360 |
| tgaggtacgt | gtggcctggt | gagaagccaa | agattcaggc | ctgtgtcctg | tcttcccctc | 420 |
| acacagcctg | gacactggtc | accagcttgc | tttgtagctg | gctgggatc | tagtggctgt | 480 |
| gggttgtaag | tgactgagaa | cctgactcaa | accggcttga | gtgaaa | | 526 |

<210> SEQ ID NO 9
<211> LENGTH: 416
<212> TYPE: DNA
<213> ORGANISM: Human

<400> SEQUENCE: 9

| | | | | | |
|---|---|---|---|---|---|
| cctctcggtc | cccagacact | gggcatttgg | cagtgaacca | gatgctgggg | gccctgtcct | 60 |
| tctggtggag | ggggaggagg | gctcagccca | gaatgttcag | accaggccgg | ctcaatggca | 120 |
| ggcctaagcc | ttacgatgct | gttccctgct | gtgtctgtag | ctcaacaact | ccgactctgg | 180 |
| gctcttcacg | gtgttcacgg | gggtccagaa | catcagcagg | atccacctcg | tggacaagtg | 240 |
| gaacgggctg | agcaaggtga | ggggcgagag | gcgaggggccc | ctgtcgccag | ggagagggga | 300 |
| gggtgggccc | ggccatggct | gctcgggagt | ggcagggacc | agagagctcc | ttcttccttt | 360 |
| gtcgtgaaga | gggtgctggg | aggatgaaca | ctcttgaagt | tggaggaggg | atttta | 416 |

<210> SEQ ID NO 10
<211> LENGTH: 436
<212> TYPE: DNA
<213> ORGANISM: Human

<400> SEQUENCE: 10

| | | | | | |
|---|---|---|---|---|---|
| tctctgtgtg | tctacatagc | ctgccctctt | cccaccgtgc | cagtattggg | aattgagtgg | 60 |
| ccgtgcgtgc | accagggtga | gttaggtgtg | cagcacctga | gagggcttat | taaggggcct | 120 |
| tggccctact | gagggggtcta | gtctggatgc | ttccccccag | gttgacttct | ggcattccga | 180 |
| tcagtgcaac | atgatcaatg | gaacttctgg | gcaaatgtgg | ccgcccttca | tgactcctga | 240 |
| gtcctcgctg | gagttctaca | gcccggaggc | ctgccggtaa | tcactgggac | tcggggcctc | 300 |
| ctgggttttcc | tgggtagctc | atggccaaat | tctgtggtgt | tggctgtgca | cttgaaagc | 360 |
| attttgactc | atcgtggatt | tgactcagta | gcccttggca | ccagcttgaa | ttctctttgg | 420 |
| tcacaccacc | aaaagc | | | | | 436 |

<210> SEQ ID NO 11
<211> LENGTH: 481
<212> TYPE: DNA
<213> ORGANISM: Human

<400> SEQUENCE: 11

-continued

```
ggaggtcgct gcagctccgc gggtgagaga tgggggcggt ttggacccgg gaggtggtag      60
cgcccgtggg gagaagtggc tggatctggg cagcctttgg cagggcctgg ctctggccgc     120
cgggtctggg tgtcccctct catcctgtct gtccctgca gatccatgaa gctaatgtac      180
aaggagtcag gggtgtttga aggcatcccc acctatcgct tcgtggctcc caaaaccctg     240
tttgccaacg gtccatcta cccacccaac gaaggcttct gcccgtgcct ggagtctgga     300
attcagaacg tcagcagctg caggttcagt acgtgccgtc ccctgttctg ggatngccgg     360
agggtgttag gtntngggca cctnanggtt tatctgccca atgctgtctg cttaatctct     420
ggcctctgta ctcttgataa cccattaagc caaaatatg atgcctctgg gacgatatct     480
g                                                                     481

<210> SEQ ID NO 12
<211> LENGTH: 430
<212> TYPE: DNA
<213> ORGANISM: Human

<400> SEQUENCE: 12
tggggctttt tacagaatgg aggaagggat cctctctgtc gggtattatg gtcatcgcca     60
cgggggtgcc gtgcagacca cagctctgtg cagacttccg gagtggcagg acgtgccaat    120
atactgtcgt tgtatgatgt cccctccctg cccttgttgt aggtgccccc ttgtttctct    180 ccatcctca cttcatcaac gccgaccgg ttctggcaga agcggtgact ggcctgcacc      240
ctaaccagga ggcacactcc ttgttcgtgg acatccaccc ggtgagcccc tgccatcctc    300 tgtgggggt gggtgattcc tggttggagc acacctggct gcctcctctc tccccaggca    360
gagagctgct gtgggctggg gtggtgggaa gcctggcttc tagaatctcg agccaccaaa    420
gttccttact                                                            430

<210> SEQ ID NO 13
<211> LENGTH: 390
<212> TYPE: DNA
<213> ORGANISM: Human

<400> SEQUENCE: 13
ccccagcctg tggcttgttt taggtaagat acaagcaagc tccactgggc agttagctgg     60
gacgcccacc ctcttgactg ggaccaggga aagaaggtt gactgtgtcc ctggagcttg     120
ggggtggcca gtctcctcac tgtgtttgtt gccgcaggtc acgggaatcc ccatgaactg    180
ctctgtgaaa ctgcagctga gcctctacat gaaatctgtc gcaggcattg gtgagtggg     240 gactgggaac tggggctgca ttgctcattg agagattang tgctcagtgc tccagtgttc    300
ccagactccc ctgacatacc ccaggaaaca gggcatgggg aagggagagg gtcctattgg    360
gggtggaatc cagtccctgc tgatcttctc                                      390

<210> SEQ ID NO 14
<211> LENGTH: 370
<212> TYPE: DNA
<213> ORGANISM: Human

<400> SEQUENCE: 14
atggctccta aagtgtttca gctcattgtt tatatttggt ggtgagggtt tagtgtgtgc     60
aaaattatac taaacctgtt tagatgttgt attcaagcag aattagatca gtttgggtg     120 taagactttg ttccaacacc tatgtcttgc ttatttccag acaaactggg aagattgagc    180
```

```
ctgtggtcct gccgctgctc tggtttgcag aggtaagggt gcgttgggca cagcgtcggg      240
ggcttttgtt aatagccaat gtgggcattt gaggcaggag gcggggggag caccttgtag      300
aaagggagag ggctgagcca gggtaaccgg actgttacat ggaccagcgt atcatacact      360
tcaccctgtc                                                             370
```

<210> SEQ ID NO 15
<211> LENGTH: 470
<212> TYPE: DNA
<213> ORGANISM: Human

<400> SEQUENCE: 15

```
cctggaggga ggaggtccct ggcaggctcc aacacatgct ttagccggga agcttgaggt       60
ggggaaaagc tgaggcgggc acagaggaag gtgttgggtg gcatctgcgc tgtagcccgc      120
agcctgcggc cccagctcat gtgtttgtca ttctgtctcc tcagagcggg gccatggagg      180
gggagactct tcacacattc tacactcagc tggtgttgat gcccaaggtg atgcactatg      240
cccagtacgt cctcctggcg ctgggctgcg tcctgctgct ggtccctgtc atctgccaaa      300
tccggagcca agtaggtgct ggccagaggg cagcccgggc tgacagccat tcgcttgcct      360
gctgggggaa aggggcctca gatcggaccc tctggccaac cgcagcctgg agcccacctc      420
cagcagcagt cctgcgtctc tgccggagtg ggagcggtca ctgctggggg                 470
```

<210> SEQ ID NO 16
<211> LENGTH: 450
<212> TYPE: DNA
<213> ORGANISM: Human

<400> SEQUENCE: 16

```
ccccacatct cagccacctg caatcgttga gggttgttgg actctaaact tatgtgcctt       60
tcctgtttcc tctttgcctt tgcaaattg aagaaccgtg taaaaccatt tttatgtggc      120 ttaacgtca actataaatt agcttggtta tcttctagga gaaatgctat ttatttttgga     180 gtagtagtaa aaagggctca aaggataagg aggccattca ggcctattct gaatccctga      240
tgacatcagc tcccaagggc tctgtgctgc aggaagcaaa actgtaggtg gtaccaggt      300 aatgccgtgc gcctccccgc cccctcccat atcaagtaga atgctggcgg cttaaaacat      360
ttggggtcct gctcattcct tcagcctcaa cttcacctgg agtgtctaca gactgaagat      420
gcatatttgt gtattttgct tttggagaaa                                       450
```

<210> SEQ ID NO 17
<211> LENGTH: 544
<212> TYPE: DNA
<213> ORGANISM: Human

<400> SEQUENCE: 17

```
actgcggaga tgagggtcta gaaggtggtg gcggggcatg tggaccgttg taagggctct       60
ggggttcctg ggtgggctgg cgaagtccta ctcacagtga ccaaccatga tgatggtccc      120
gatagaggag gagagggagg aggagggaaa aggaagggtg aggggctcag aggggagagc      180
tgggaggagg ggagacatag gtgggggaag gggtaggaga aagggaagg gagcaagagg       240 gtgaggggca ccaggcccca tagacgtttt ggctcagcgg ccacgaggct tcatcagctc      300 ccgcccaaa acggaagcga ggccgtgggg gcagcggcag catggcgggg cttgtcttgg       360
cggccatggc cccgccccct gccgtccga tcagcgcccc gccccgtccc cgccccgacc       420 ccgcccggg cccgctcagg ccccgcccct gccgccggaa tcctgaagcc caaggctgcc       480
```

```
cggggcggt ccggcggcgc cggcgatggg gcataaaacc actggccacc tgccgggctg      540
ctcc                                                                  544

<210> SEQ ID NO 18
<211> LENGTH: 190
<212> TYPE: DNA
<213> ORGANISM: Human

<400> SEQUENCE: 18
gtgggtgagg gagaccccag ggggtccgcg cacggacccg ggctgttggg cgctgggcgc       60
cgggaggacc cgcgcgttgc ggtgggtggg cgaccgcagc ggaatcggcg cccgggcctg      120
gcgccgcaga acacgaggga ggccaggcgc ttcgggaggg gctgctgccc gcctccccac      180
caccctcacc                                                            190

<210> SEQ ID NO 19
<211> LENGTH: 159
<212> TYPE: DNA
<213> ORGANISM: Human

<400> SEQUENCE: 19
agcctcatgt gcgaagggct ttcccaccac ctcctatccc aagctcccgc cgaggagccc       60
cttccctggc cgggctcggg cagctgttcc ggagccttgt ggtgggcgt ggggccctca      120 tcactctcct cacaagcgta cttgtccctt cccctgcag                            159

<210> SEQ ID NO 20
<211> LENGTH: 162
<212> TYPE: DNA
<213> ORGANISM: Human

<400> SEQUENCE: 20
gtgaggctgt gtccacgtga tggtggacgg gccggctgac gctgggcatg ggacgggtct       60
caagtggacg ggatggggag gctgctgact gaccccaaa cattgttccg gaagcacgca      120
actcatagtc ggggtaagtg ctactcccaa aaaagtttgc gt                         162

<210> SEQ ID NO 21
<211> LENGTH: 191
<212> TYPE: DNA
<213> ORGANISM: Human

<400> SEQUENCE: 21
catgtcctgc agtgggcagg cagcgggagg gacagacttg gcgaaggggc cgagctcagc       60
tttggctgtg gggccggagg tgtgcacaga cgtccagggc ccctggttcc caggcaggca      120
ttgcaggcga gtagaaggga aacgtcccat gcagcggggc ggggcgtctg acccactggc      180
ttcccccaca g                                                          191

<210> SEQ ID NO 22
<211> LENGTH: 162
<212> TYPE: DNA
<213> ORGANISM: Human

<400> SEQUENCE: 22
gtgaggctgc cctgtggccc acgccgcctc gcaccctgac ctcgtccct gtctctcctc       60 ccgcctgccc cttgtgcaga gagcagtccc tgaggtggtc ggagcgtggg gactcacgcc      120
tggtgggtgg ctttcggccc tgtgctgtct ccaccacccc ca                        162
```

<210> SEQ ID NO 23
<211> LENGTH: 161
<212> TYPE: DNA
<213> ORGANISM: Human

<400> SEQUENCE: 23

```
ggtggttctg gtgtcccaga tgccccacgt ggccactcca ggggcctcct gcaccccagc      60
atttcccttc atgggctctt tgctgtgagg cccagctggg gccaagggag gatgggccag     120
ccacgtccag cctctgacac tagtgtccct tcgccttgca g                         161
```

<210> SEQ ID NO 24
<211> LENGTH: 162
<212> TYPE: DNA
<213> ORGANISM: Human

<400> SEQUENCE: 24

```
gtacgtgtgg cctggtgaga agccaaagat tcaggcctgt gtcctgtctt cccctcacac      60
agcctggaca ctggtcacca gcttgctttg tagctggctg gggatctagt ggctgtgggt     120
tgtaagtgac tgagaacctg actcaaaccg gcttgagtga aa                        162
```

<210> SEQ ID NO 25
<211> LENGTH: 160
<212> TYPE: DNA
<213> ORGANISM: Human

<400> SEQUENCE: 25

```
cctctcggtc cccagacact gggcatttgg cagtgaacca gatgctgggg gccctgtcct      60
tctggtggag gggaggagg gctcagccca gaatgttcag accaggccgg ctcaatggca     120
ggcctaagcc ttacgatgct gttccctgct gtgtctgtag                          160
```

<210> SEQ ID NO 26
<211> LENGTH: 160
<212> TYPE: DNA
<213> ORGANISM: Human

<400> SEQUENCE: 26

```
gtgaggggcg agaggcgagg gccctgtcg ccagggagag gggagggtgg gcccggccat      60
ggctgctcgg gagtggcagg gaccagagag ctccttcttc ctttgtcgtg aagagggtgc    120
tgggaggatg aacactcttg aagttggagg agggatttta                          160
```

<210> SEQ ID NO 27
<211> LENGTH: 160
<212> TYPE: DNA
<213> ORGANISM: Human

<400> SEQUENCE: 27

```
tctctgtgtg tctacatagc ctgccctctt cccaccgtgc cagtattggg aattgagtgg      60
ccgtgcgtgc accagggtga gttaggtgtg cagcacctga gagggcttat taagggcct     120
tggccctact gagggtcta gtctggatgc ttccccccag                           160
```

<210> SEQ ID NO 28
<211> LENGTH: 160
<212> TYPE: DNA
<213> ORGANISM: Human

<400> SEQUENCE: 28

```
gtaatcactg ggactcgggg cctcctgggt ttcctgggta gctcatggcc aaattctgtg      60
```

```
gtgttggctg tgcacttgga aagcattttg actcatcgtg gatttgactc agtagccctt    120
ggcaccagct tgaattctct ttggtcacac caccaaaagc                          160
```

<210> SEQ ID NO 29
<211> LENGTH: 161
<212> TYPE: DNA
<213> ORGANISM: Human

<400> SEQUENCE: 29

```
ggaggtcgct gcagctccgc gggtgagaga tggggcggt ttggacccgg gaggtggtag     60
cgcccgtggg gagaagtggc tggatctggg cagcctttgg cagggcctgg ctctggccgc   120
cgggtctggg tgtcccctct catcctgtct gtccctgca g                        161
```

<210> SEQ ID NO 30
<211> LENGTH: 153
<212> TYPE: DNA
<213> ORGANISM: Human

<400> SEQUENCE: 30

```
gtacgtgccg tcccctgttc tgggatngcc ggagggtgtt aggtntnggg cacctnangg     60
tttatctgcc caatgctgtc tgcttaatct ctggcctctg tactcttgat aacccattaa   120
gccaaaaata tgatgcctct gggacgatat ctg                                153
```

<210> SEQ ID NO 31
<211> LENGTH: 162
<212> TYPE: DNA
<213> ORGANISM: Human

<400> SEQUENCE: 31

```
tggggctttt tacagaatgg aggaagggat cctctctgtc gggtattatg gtcatcgcca     60
cgggggtgcc gtgcagacca cagctctgtg cagacttccg gagtggcagg acgtgccaat   120
atactgtcgt tgtatgatgt cccctccctg cccttgttgt ag                      162
```

<210> SEQ ID NO 32
<211> LENGTH: 149
<212> TYPE: DNA
<213> ORGANISM: Human

<400> SEQUENCE: 32

```
gtgagcccct gccatcctct gtgggggtg ggtgattcct ggttggagca cacctggctg     60
cctcctctct cccaggcag agagctgctg tgggctgggg tggtgggaag cctggcttct    120
agaatctcga gccaccaaag ttccttact                                     149
```

<210> SEQ ID NO 33
<211> LENGTH: 157
<212> TYPE: DNA
<213> ORGANISM: Human

<400> SEQUENCE: 33

```
ccccagcctg tggcttgttt taggtaagat acaagcaagc tccactgggc agttagctgg     60
gacgcccacc ctcttgactg ggaccaggga aagaaggtt gactgtgtcc ctggagcttg    120
ggggtggcca gtctcctcac tgtgtttgtt gccgcag                            157
```

<210> SEQ ID NO 34
<211> LENGTH: 159
<212> TYPE: DNA

<213> ORGANISM: Human

<400> SEQUENCE: 34

| | | | | | |
|---|---|---|---|---|---|
| gtgagtgggg | actgggaact | ggggctgcat | tgctcattga | gagattangt | gctcagtgct | 60 |
| ccagtgttcc | cagactcccc | tgacataccc | caggaaacag | ggcatgggga | agggagaggg | 120 |
| tcctattggg | ggtggaatcc | agtccctgct | gatcttctc | | | 159 |

<210> SEQ ID NO 35
<211> LENGTH: 160
<212> TYPE: DNA
<213> ORGANISM: Human

<400> SEQUENCE: 35

| | | | | | |
|---|---|---|---|---|---|
| atggctccta | aagtgtttca | gctcattgtt | tatatttggt | ggtgagggtt | tagtgtgtgc | 60 |
| aaaattatac | taaacctgtt | tagatgttgt | attcaagcag | aattagatca | agtttgggtg | 120 |
| taagactttg | ttccaacacc | tatgtcttgc | ttatttccag | | | 160 |

<210> SEQ ID NO 36
<211> LENGTH: 158
<212> TYPE: DNA
<213> ORGANISM: Human

<400> SEQUENCE: 36

| | | | | | |
|---|---|---|---|---|---|
| gtaagggtgc | gttgggcaca | gcgtcggggg | cttttgttaa | tagccaatgt | gggcatttga | 60 |
| ggcaggaggc | gggggagca | ccttgtagaa | agggagaggg | ctgagccagg | gtaaccggac | 120 |
| tgttacatgg | accagcgtat | catacacttc | accctgtc | | | 158 |

<210> SEQ ID NO 37
<211> LENGTH: 164
<212> TYPE: DNA
<213> ORGANISM: Human

<400> SEQUENCE: 37

| | | | | | |
|---|---|---|---|---|---|
| cctggaggga | ggaggtccct | ggcaggctcc | aacacatgct | ttagccggga | agcttgaggt | 60 |
| ggggaaaagc | tgaggcgggc | acagaggaag | gtgttgggtg | gcatctgcgc | tgtagcccgc | 120 |
| agcctgcggc | cccagctcat | gtgtttgtca | ttctgtctcc | tcag | | 164 |

<210> SEQ ID NO 38
<211> LENGTH: 159
<212> TYPE: DNA
<213> ORGANISM: Human

<400> SEQUENCE: 38

| | | | | | |
|---|---|---|---|---|---|
| gtaggtgctg | gccagagggc | agcccgggct | gacagccatt | cgcttgcctg | ctggggggaaa | 60 |
| ggggcctcag | atcggaccct | ctggccaacc | gcagcctgga | gcccacctcc | agcagcagtc | 120 |
| ctgcgtctct | gccggagtgg | gagcggtcac | tgctggggg | | | 159 |

<210> SEQ ID NO 39
<211> LENGTH: 158
<212> TYPE: DNA
<213> ORGANISM: Human

<400> SEQUENCE: 39

| | | | | | |
|---|---|---|---|---|---|
| ccccacatct | cagccacctg | caatcgttga | gggttgttgg | actctaaact | tatgtgcctt | 60 |
| tcctgtttcc | tctttgcctt | ttgcaaattg | aagaaccgtg | taaaaccatt | tttatgtggc | 120 |
| ttcaacgtca | actataaatt | agcttggtta | tcttctag | | | 158 |

<210> SEQ ID NO 40
<211> LENGTH: 163
<212> TYPE: DNA
<213> ORGANISM: Human

<400> SEQUENCE: 40
gtgggtacca ggtaatgccg tgcgcctccc cgcccctcc catatcaagt agaatgctgg        60
cggcttaaaa catttggggt cctgctcatt ccttcagcct caacttcacc tggagtgtct       120
acagactgaa gatgcatatt tgtgtatttt gcttttggag aaa                         163

<210> SEQ ID NO 41
<211> LENGTH: 23
<212> TYPE: DNA
<213> ORGANISM: Human

<400> SEQUENCE: 41
cccctgccgc cggaatcctg aag                                                23

<210> SEQ ID NO 42
<211> LENGTH: 24
<212> TYPE: DNA
<213> ORGANISM: Human

<400> SEQUENCE: 42
cgctttggcg gagcagccca tgtc                                               24

<210> SEQ ID NO 43
<211> LENGTH: 24
<212> TYPE: DNA
<213> ORGANISM: Human

<400> SEQUENCE: 43
tggggccctc atcactctcc tcac                                               24

<210> SEQ ID NO 44
<211> LENGTH: 23
<212> TYPE: DNA
<213> ORGANISM: Human

<400> SEQUENCE: 44
gcagcctccc catcccgtcc act                                                23

<210> SEQ ID NO 45
<211> LENGTH: 18
<212> TYPE: DNA
<213> ORGANISM: Human

<400> SEQUENCE: 45
attgcaggcg agtagaag                                                      18

<210> SEQ ID NO 46
<211> LENGTH: 18
<212> TYPE: DNA
<213> ORGANISM: Human

<400> SEQUENCE: 46
caggcgggag gagagaca                                                      18

<210> SEQ ID NO 47
<211> LENGTH: 20
<212> TYPE: DNA

```
<213> ORGANISM: Human

<400> SEQUENCE: 47
tgggctcttt gctgtgaggc                                              20

<210> SEQ ID NO 48
<211> LENGTH: 20
<212> TYPE: DNA
<213> ORGANISM: Human

<400> SEQUENCE: 48
ccaggctgtg tgagggggaag                                             20

<210> SEQ ID NO 49
<211> LENGTH: 20
<212> TYPE: DNA
<213> ORGANISM: Human

<400> SEQUENCE: 49
gcccagaatg ttcagaccag                                              20

<210> SEQ ID NO 50
<211> LENGTH: 20
<212> TYPE: DNA
<213> ORGANISM: Human

<400> SEQUENCE: 50
gcaccctctt cacgacaaag                                              20

<210> SEQ ID NO 51
<211> LENGTH: 19
<212> TYPE: DNA
<213> ORGANISM: Human

<400> SEQUENCE: 51
cacctgagag ggcttatta                                               19

<210> SEQ ID NO 52
<211> LENGTH: 19
<212> TYPE: DNA
<213> ORGANISM: Human

<400> SEQUENCE: 52
caaaatgctt tccaagtgc                                               19

<210> SEQ ID NO 53
<211> LENGTH: 20
<212> TYPE: DNA
<213> ORGANISM: Human

<400> SEQUENCE: 53
gccgccgggt ctgggtgtcc                                              20

<210> SEQ ID NO 54
<211> LENGTH: 23
<212> TYPE: DNA
<213> ORGANISM: Human

<400> SEQUENCE: 54
cagaggccag agattaagca gac                                          23

<210> SEQ ID NO 55
<211> LENGTH: 20
```

<212> TYPE: DNA
<213> ORGANISM: Human

<400> SEQUENCE: 55
ttgtatgatg tccctccct                                           20

<210> SEQ ID NO 56
<211> LENGTH: 20
<212> TYPE: DNA
<213> ORGANISM: Human

<400> SEQUENCE: 56
ttcccaccac cccagcccac                                          20

<210> SEQ ID NO 57
<211> LENGTH: 20
<212> TYPE: DNA
<213> ORGANISM: Human

<400> SEQUENCE: 57
ggttgactgt gtccctggag                                          20

<210> SEQ ID NO 58
<211> LENGTH: 21
<212> TYPE: DNA
<213> ORGANISM: Human

<400> SEQUENCE: 58
gggaacactg gagcactgag c                                        21

<210> SEQ ID NO 59
<211> LENGTH: 20
<212> TYPE: DNA
<213> ORGANISM: Human

<400> SEQUENCE: 59
ggtggtgagg gtttagtgtg                                          20

<210> SEQ ID NO 60
<211> LENGTH: 20
<212> TYPE: DNA
<213> ORGANISM: Human

<400> SEQUENCE: 60 ctcccccgc ctcctgcctc                                           20

<210> SEQ ID NO 61
<211> LENGTH: 20
<212> TYPE: DNA
<213> ORGANISM: Human

<400> SEQUENCE: 61
aaggtgttgg gtggcatctg                                          20

<210> SEQ ID NO 62
<211> LENGTH: 20
<212> TYPE: DNA
<213> ORGANISM: Human

<400> SEQUENCE: 62
ggctccaggc tgcggttggc                                          20

<210> SEQ ID NO 63

-continued

```
<211> LENGTH: 19
<212> TYPE: DNA
<213> ORGANISM: Human

<400> SEQUENCE: 63
ttgaagaacc gtgtaaaac                                                      19

<210> SEQ ID NO 64
<211> LENGTH: 18
<212> TYPE: DNA
<213> ORGANISM: Human

<400> SEQUENCE: 64
ttgaggctga aggaatga                                                       18

<210> SEQ ID NO 65
<211> LENGTH: 430
<212> TYPE: DNA
<213> ORGANISM: Human

<400> SEQUENCE: 65
tggggctttt tacagaatgg aggaagggat cctctctgtc gggtattatg gtcatcgcca         60
cgggggtgcc gtgcagacca cagctctgtg cagacttccg gagtggcagg acgtgccaat        120
atactgtcgt tgtatgatgt cccctccctg cccttgttgt aggtgccccc ttgtttctct        180
cccatcctca cttcatcaac gctgacccgg ttctggcaga agcggtgact ggcctgcacc        240
ctaaccagga ggcacactcc ttgttcgtgg acatccaccc ggtgagcccc tgccatcctc        300 tgtgggggt gggtgattcc tggttggagc acacctggct gcctcctctc tccccaggca         360
gagagctgct gtgggctggg gtggtgggaa gcctggcttc tagaatctcg agccaccaaa        420
gttccttact                                                              430

<210> SEQ ID NO 66
<211> LENGTH: 160
<212> TYPE: DNA
<213> ORGANISM: Human

<400> SEQUENCE: 66
gtgaggggcg agaggcgagg gccctgtcg ccagggagag ggagggtgg gcctggccat          60 ggctgctcgg gagtggcagg gaccagagag ctccttcttc ctttgtcgtg aagagggtgc       120
tgggaggatg aacactcttg aagttggagg agggatttta                             160

<210> SEQ ID NO 67
<211> LENGTH: 20
<212> TYPE: DNA
<213> ORGANISM: Human

<400> SEQUENCE: 67
aaccgggtca gcgttgagga                                                    20

<210> SEQ ID NO 68
<211> LENGTH: 31
<212> TYPE: DNA
<213> ORGANISM: Human

<400> SEQUENCE: 68
tgccagaacc gggtcagcgt tgaggaagtg a                                       31

<210> SEQ ID NO 69
<211> LENGTH: 20
```

<212> TYPE: DNA
<213> ORGANISM: Human

<400> SEQUENCE: 69
tcctcaacgc tgacccggtt                                            20

<210> SEQ ID NO 70
<211> LENGTH: 31
<212> TYPE: DNA
<213> ORGANISM: Human

<400> SEQUENCE: 70
tcacttcctc aacgctgacc cggttctggc a                               31

<210> SEQ ID NO 71
<211> LENGTH: 20
<212> TYPE: DNA
<213> ORGANISM: Human

<400> SEQUENCE: 71
aaccgggtcg gcgttgatga                                            20

<210> SEQ ID NO 72
<211> LENGTH: 31
<212> TYPE: DNA
<213> ORGANISM: Human

<400> SEQUENCE: 72
tgccagaacc gggtcggcgt tgatgaagtg a                               31

<210> SEQ ID NO 73
<211> LENGTH: 20
<212> TYPE: DNA
<213> ORGANISM: Human

<400> SEQUENCE: 73
tcatcaacgc cgacccggtt                                            20

<210> SEQ ID NO 74
<211> LENGTH: 31
<212> TYPE: DNA
<213> ORGANISM: Human

<400> SEQUENCE: 74
tcacttcatc aacgccgacc cggttctggc a                               31

<210> SEQ ID NO 75
<211> LENGTH: 21
<212> TYPE: DNA
<213> ORGANISM: Human

<400> SEQUENCE: 75
agccatggcc gggcccaccc t                                          21

<210> SEQ ID NO 76
<211> LENGTH: 31
<212> TYPE: DNA
<213> ORGANISM: Human

<400> SEQUENCE: 76
cgagcagcca tggccgggcc caccctcccc t                               31

<210> SEQ ID NO 77

```
<211> LENGTH: 21
<212> TYPE: DNA
<213> ORGANISM: Human

<400> SEQUENCE: 77
agggtgggcc cggccatggc t                                          21

<210> SEQ ID NO 78
<211> LENGTH: 31
<212> TYPE: DNA
<213> ORGANISM: Human

<400> SEQUENCE: 78
aggggagggt gggcccggcc atggctgctc g                               31

<210> SEQ ID NO 79
<211> LENGTH: 21
<212> TYPE: DNA
<213> ORGANISM: Human

<400> SEQUENCE: 79
agccatggcc aggcccaccc t                                          21

<210> SEQ ID NO 80
<211> LENGTH: 31
<212> TYPE: DNA
<213> ORGANISM: Human

<400> SEQUENCE: 80
cgagcagcca tggccaggcc caccctcccc t                               31

<210> SEQ ID NO 81
<211> LENGTH: 21
<212> TYPE: DNA
<213> ORGANISM: Human

<400> SEQUENCE: 81
agggtgggcc tggccatggc t                                          21

<210> SEQ ID NO 82
<211> LENGTH: 31
<212> TYPE: DNA
<213> ORGANISM: Human

<400> SEQUENCE: 82
aggggagggt gggcctggcc atggctgctc g                               31

<210> SEQ ID NO 83
<211> LENGTH: 22
<212> TYPE: DNA
<213> ORGANISM: Human

<400> SEQUENCE: 83
tcctgggtgg gctggcgaag tc                                         22

<210> SEQ ID NO 84
<211> LENGTH: 24
<212> TYPE: DNA
<213> ORGANISM: Human

<400> SEQUENCE: 84
gttttggggc gggagctgat gaag                                       24
```

```
<210> SEQ ID NO 85
<211> LENGTH: 18
<212> TYPE: DNA
<213> ORGANISM: Human

<400> SEQUENCE: 85
tgtaaaacga cggccagt                                                        18

<210> SEQ ID NO 86
<211> LENGTH: 18
<212> TYPE: DNA
<213> ORGANISM: Human

<400> SEQUENCE: 86
caggaaacag ctatgacc                                                        18

<210> SEQ ID NO 87
<211> LENGTH: 62
<212> TYPE: DNA
<213> ORGANISM: Human

<400> SEQUENCE: 87
ctgagcaagg tgagggggcga gaggcgaggg ccctgtcgc cagggagggg aggtgggcc           60 yg                                                                         62

<210> SEQ ID NO 88
<211> LENGTH: 51
<212> TYPE: DNA
<213> ORGANISM: Human

<400> SEQUENCE: 88
cstgcggccc cagctcatgt gtttgtcatt ctgtctcctc agagcggggc c                   51

<210> SEQ ID NO 89
<211> LENGTH: 24
<212> TYPE: DNA
<213> ORGANISM: Human

<400> SEQUENCE: 89
ccggcgatgg ggcataaaac cact                                                 24

<210> SEQ ID NO 90
<211> LENGTH: 23
<212> TYPE: DNA
<213> ORGANISM: Human

<400> SEQUENCE: 90
cgcccagcac agcgcacagt agc                                                  23

<210> SEQ ID NO 91
<211> LENGTH: 20
<212> TYPE: DNA
<213> ORGANISM: Human

<400> SEQUENCE: 91
gcccagaatg ttcagaccag                                                      20

<210> SEQ ID NO 92
<211> LENGTH: 20
<212> TYPE: DNA
<213> ORGANISM: Human

<400> SEQUENCE: 92
```

```
gcaccctctt cacgacaaag                                                      20

<210> SEQ ID NO 93
<211> LENGTH: 34
<212> TYPE: DNA
<213> ORGANISM: Human

<400> SEQUENCE: 93
ccttgtttct ctcccatcct cacttcctca aggc                                      34

<210> SEQ ID NO 94
<211> LENGTH: 22
<212> TYPE: DNA
<213> ORGANISM: Human

<400> SEQUENCE: 94
caccacccca gcccacagca gc                                                   22

<210> SEQ ID NO 95
<211> LENGTH: 1002
<212> TYPE: DNA
<213> ORGANISM: Human

<400> SEQUENCE: 95
actgcggaga tgagggtcta gaaggtggtg gcggggcatg tggaccgttg taagggctct          60
ggggttcctg ggtgggctgg cgaagtccta ctcacagtga ccaaccatga tgatggtccc         120
gatagaggag gagaggggagg aggagggaaa aggaaggtg aggggctcag aggggagagc         180
tgggaggagg ggagacatag gtgggggaag gggtaggaga aaggggaagg gagcaagagg         240
gtgaggggca ccaggcccca tagacgtttt ggctcagcgg ccacgaggct tcatcagctc         300
ccgccccaaa acggaagcga ggccgtgggg gcagcggcag catggcgggg cttgtcttgg         360
cggccatggc cccgcccccct gccgtccga tcagcgcccc gccccgtccc cgccccgacc         420
ccgccccggg cccgctcagg ccccgcccct gccgccggaa tcctgaagcc caaggctgcc         480
cgggggcggt ccggcggcgc cggcgatggg gcataaaacc actggccacc tgccgggctg         540
ctcctgcgtg cgctgccgtc ccggatccac cgtgcctctg cggcctgcgt gccccgagtc         600
cccgcctgtg tcgtctctgt cgccgtcccc gtctcctgcc aggcgcggag ccctgcgagc         660
cgcgggtggg ccccaggcgc gcagacatga gctgctccgc caaagcgcgc tgggctgccg         720
gggcgctggg cgtcgcgggg ctactgtgcg ctgtgctggg cgctgtcatg atcgtgatgg         780
tgccgtcgct catcaagcag caggtcctta aggtgggtga gggagacccc aggggggtccg         840 cgcacggacc cgggctgttg ggcgctgggc gccgggagga cccgcgcgtt gcggtgggtg         900
ggcgaccgca gcggaatcgg cgcccgggcc tggcgccgca gaacacgagg gaggccaggc         960
gcttcgggag gggctgctgc ccgcctcccc accaccctca cc                          1002

<210> SEQ ID NO 96
<211> LENGTH: 495
<212> TYPE: DNA
<213> ORGANISM: Human

<400> SEQUENCE: 96
catgtcctgc agtgggcagg cagcgggagg gacagacttg gcgaaggggc cgagctcagc          60
tttggctgtg gggccggagg tgtgcacaga cgtccagggc ccctggttcc caggcaggca        120
ttgcaggcga gtagaaggga aacgtcccat gcagcggggc ggggcgtctg acccactggc        180
ttcccccaca gggagttcag gcacaaaagc aacatcacct tcaacaacaa cgacaccgtg        240
```

```
tccttcctcg agtaccgcac cttccagttc cagccctcca agtcccacgg ctcggagagc      300
gactacatca tcatgcccaa catcctggtc ttggtgaggc tgccctgtgg cccacgccgc      360
ctcgcaccct gacctcgtcc cctgtctctc ctcccgcctg cccttgtgc agagagcagt      420 ccctgaggtg gtcggagcgt ggggactcac gcctggtggg tggctttcgg ccctgtgctg      480
tctccaccac cccca                                                      495
```

<210> SEQ ID NO 97
<211> LENGTH: 470
<212> TYPE: DNA
<213> ORGANISM: Human

<400> SEQUENCE: 97

```
cctggaggga ggaggtccct ggcaggctcc aacacatgct ttagccggga agcttgaggt       60
ggggaaaagc tgaggcgggc acagaggaag gtgttgggtg gcatctgcgc tgtagcccgc      120
agcgtgcggc cccagctcat gtgtttgtca ttctgtctcc tcagagcggg gccatggagg      180
gggagactct tcacacattc tacactcagc tggtgttgat gcccaaggtg atgcactatg      240
cccagtacgt cctcctggcg ctgggctgcg tcctgctgct ggtccctgtc atctgccaaa      300
tccggagcca gtaggtgct ggccagaggg cagcccgggc tgacagccat tcgcttgcct       360
gctgggggaa aggggcctca gatcggaccc tctggccaac cgcagcctgg agcccacctc      420
cagcagcagt cctgcgtctc tgccggagtg ggagcggtca ctgctggggg                 470
```

<210> SEQ ID NO 98
<211> LENGTH: 21
<212> TYPE: DNA
<213> ORGANISM: Human

<400> SEQUENCE: 98

```
gcggagcagc tcatgtctgc g                                                21
```

<210> SEQ ID NO 99
<211> LENGTH: 31
<212> TYPE: DNA
<213> ORGANISM: Human

<400> SEQUENCE: 99

```
ctttcgcgga gcagctcatg tctgcgcgcc t                                     31
```

<210> SEQ ID NO 100
<211> LENGTH: 21
<212> TYPE: DNA
<213> ORGANISM: Human

<400> SEQUENCE: 100

```
cgcagacatg agctgctccg c                                                21
```

<210> SEQ ID NO 101
<211> LENGTH: 31
<212> TYPE: DNA
<213> ORGANISM: Human

<400> SEQUENCE: 101

```
aggcgcgcag acatgagctg ctccgccaaa g                                     31
```

<210> SEQ ID NO 102
<211> LENGTH: 21
<212> TYPE: DNA

-continued

<213> ORGANISM: Human

<400> SEQUENCE: 102
gcggagcagc gcatgtctgc g                                       21

<210> SEQ ID NO 103
<211> LENGTH: 31
<212> TYPE: DNA
<213> ORGANISM: Human

<400> SEQUENCE: 103
ctttcgcgga gcagcgcatg tctgcgcgcc t                            31

<210> SEQ ID NO 104
<211> LENGTH: 21
<212> TYPE: DNA
<213> ORGANISM: Human

<400> SEQUENCE: 104
cgcagacatg cgctgctccg c                                       21

<210> SEQ ID NO 105
<211> LENGTH: 31
<212> TYPE: DNA
<213> ORGANISM: Human

<400> SEQUENCE: 105
aggcgcgcag acatgcgctg ctccgccaaa g                            31

<210> SEQ ID NO 106
<211> LENGTH: 21
<212> TYPE: DNA
<213> ORGANISM: Human

<400> SEQUENCE: 106
ttgggcatga tgatgtagac g                                       21

<210> SEQ ID NO 107
<211> LENGTH: 31
<212> TYPE: DNA
<213> ORGANISM: Human

<400> SEQUENCE: 107
ggatgttggg catgatgatg tagacgctct c                            31

<210> SEQ ID NO 108
<211> LENGTH: 21
<212> TYPE: DNA
<213> ORGANISM: Human

<400> SEQUENCE: 108
cgactacatc atcatgccca a                                       21

<210> SEQ ID NO 109
<211> LENGTH: 31
<212> TYPE: DNA
<213> ORGANISM: Human

<400> SEQUENCE: 109
gagagcgact acatcatcat gcccaacatc c                            31

<210> SEQ ID NO 110
<211> LENGTH: 21

```
<212> TYPE: DNA
<213> ORGANISM: Human

<400> SEQUENCE: 110
ttgggcatga ggatgtagac g                                      21

<210> SEQ ID NO 111
<211> LENGTH: 31
<212> TYPE: DNA
<213> ORGANISM: Human

<400> SEQUENCE: 111
ggatgttggg catgaggatg tagacgctct c                           31

<210> SEQ ID NO 112
<211> LENGTH: 21
<212> TYPE: DNA
<213> ORGANISM: Human

<400> SEQUENCE: 112
cgactacatc ctcatgccca a                                      21

<210> SEQ ID NO 113
<211> LENGTH: 32
<212> TYPE: DNA
<213> ORGANISM: Human

<400> SEQUENCE: 113
gagagcgact acatccatca tgcccaacat cc                          32

<210> SEQ ID NO 114
<211> LENGTH: 21
<212> TYPE: DNA
<213> ORGANISM: Human

<400> SEQUENCE: 114
tggggccgca cgctgcgggc t                                      21

<210> SEQ ID NO 115
<211> LENGTH: 31
<212> TYPE: DNA
<213> ORGANISM: Human

<400> SEQUENCE: 115
tgagctgggg ccgcacgctg cgggctacag c                           31

<210> SEQ ID NO 116
<211> LENGTH: 21
<212> TYPE: DNA
<213> ORGANISM: Human

<400> SEQUENCE: 116
agcccgcagc gtgcggcccc a                                      21

<210> SEQ ID NO 117
<211> LENGTH: 31
<212> TYPE: DNA
<213> ORGANISM: Human

<400> SEQUENCE: 117
gctgtagccc gcagcgtgcg gccccagctc a                           31

<210> SEQ ID NO 118
```

-continued

```
<211> LENGTH: 21
<212> TYPE: DNA
<213> ORGANISM: Human

<400> SEQUENCE: 118
tggggccgca ggctgcgggc t                                        21

<210> SEQ ID NO 119
<211> LENGTH: 31
<212> TYPE: DNA
<213> ORGANISM: Human

<400> SEQUENCE: 119
tgagctgggg ccgcaggctg cgggctacag c                             31

<210> SEQ ID NO 120
<211> LENGTH: 21
<212> TYPE: DNA
<213> ORGANISM: Human

<400> SEQUENCE: 120
agcccgcagc ctgcggcccc a                                        21

<210> SEQ ID NO 121
<211> LENGTH: 31
<212> TYPE: DNA
<213> ORGANISM: Human

<400> SEQUENCE: 121
gctgtagccc gcagcctgcg gccccagctc a                             31
```